US006307016B1

(12) United States Patent
Lehrer et al.

(10) Patent No.: US 6,307,016 B1
(45) Date of Patent: Oct. 23, 2001

(54) PAREVINS AND TACHYTEGRINS

(75) Inventors: Robert I. Lehrer, Santa Monica; Sylvia S. L. Harwig, Woodland Hills; Conway C. Chang, San Francisco; Chee L. Gu, Saratoga, all of CA (US)

(73) Assignee: IntraBiotics Pharmaceuticals, Inc., Mountain View, CA (US)

( * ) Notice: Subject to any disclaimer, the term of this patent is extended or adjusted under 35 U.S.C. 154(b) by 0 days.

(21) Appl. No.: 09/128,344

(22) Filed: Aug. 3, 1998

Related U.S. Application Data

(63) Continuation-in-part of application No. 08/674,622, filed on Jul. 3, 1996, now abandoned.
(60) Provisional application No. 60/000,898, filed on Jul. 6, 1995.

(51) Int. Cl.[7] .................................................... A61K 38/10
(52) U.S. Cl. ............................ 530/326; 530/317; 514/12; 514/13
(58) Field of Search .................................. 514/12, 13, 14; 530/319, 328

(56) References Cited

U.S. PATENT DOCUMENTS

| | | |
|---|---|---|
| 5,434,074 | 7/1995 | Gibson et al. . |
| 5,464,823 | 11/1995 | Lehrer et al. . |
| 5,693,486 | 12/1997 | Lehrer et al. . |
| 5,708,154 | 1/1998 | Smith et al. . |
| 5,804,558 | 9/1998 | Lehrer et al. . |
| 5,994,306 * | 11/1999 | Chang et al. ............................ 514/13 |
| 6,043,220 | 3/2000 | Chang et al. ............................ 514/12 |

FOREIGN PATENT DOCUMENTS

| | | |
|---|---|---|
| 0 545 730 | 6/1993 | (EP) . |
| WO 95/03325 | 2/1995 | (WO) . |
| WO 9604373 | 2/1996 | (WO) . |
| WO 96/37508 | 11/1996 | (WO) . |
| WO 97/02287 | 1/1997 | (WO) . |
| WO 97/18826 | 5/1997 | (WO) . |
| WO 97/18827 | 5/1997 | (WO) . |
| WO 98/03192 | 1/1998 | (WO) . |

OTHER PUBLICATIONS

Harwig et al., 1995, "Determination of Disulphide Bridges in PG–2, an Anti–microbial Peptide from Porcine Leukocytes", *Journal of Peptide Science*, 3:207–215.

Hu et al., 1991, "Isolation and Characterization of Corticostatic Peptides from Guinea Pig Bone Marrow," *Biochem. Biophys. Res. Commun.* 180:558–565.

Kokryakov et al., 1993, "Protegrins: leukocyte antimicrobial peptides that combine features of corticostatic defensins and tachyplesins", *Febs*, 327(2):231–236.

Masuda et al., 1992, "A novel anti–HIV synthetic peptide, T–22 ([Tyr5, 12,Lys7]–polyphemusin ll)," *Biochem. Biophys. Res. Commun.* 189(2):845–850.

Matsuzaki et al., 1991, "Interactions of an antimicrobial peptide, tachyplesin l, with lipid membranes", *Biochimica et Biophysica Acta.*, 1070:259–264.

Matsuzaki et al., 1993, "Role of Disulfide Linkages in Tachyplesin–Lipid Interactions", *Biochemistry*, 32(43):11704–11710.

Mirgorodskaya et al., 1993, "Primary Structure of three cationic peptides from porcine neutrophils", *Febs*, 330(3):339–342.

Muta et al., 1990, "Tachyplesins isolated from hemocytes of Southeast Asian horseshoe crabs (*Carcinoscorpius rotundicauda* and *Tachypleus gigas*): identification of a new tachyplesin, tachyplesin lll, and a processing intermediate of its precursor," *J. Biochem (Tokyo)* 108(2):261–266.

Otaka et al., 1994, "Molecular parameters for the anti–human immunodeficiency virus activity of T22 ([Tyr5, 12,Lys7]–polyphemusin ll)," *Biol. Pharm. Bull.* 17(12):1669–1672.

Park et al., 1992, "Conformation of Tachyplesin 1 from *Tachypleus tridentatus* When interacting with Lipid Matrices", *Biochemistry*, 31(48):12241–12247.

Sonis, Ch. XL–14 "Oral Complications", *Complications of Cancer and Their Treatments*, pp. 2381–2388

Sonis, Section 6, "Oral Complications of Cancer Therapy", *Adverse Effects of Treatment—Oral Complications of Cancer Chemotherapy*, pp. 2385–2394.

Soto et al., 1995, "Mapping of the linear antigenic determinants from the *Leishmania infantum* histone H2A recognized by sera from dogs with leishmaniasis", *Immunology Letters*, 48:209–214.

Storici and Zanetti, 1993, "A Novel cDNA Sequence Encoding a Pig Leukocyte Antimicrobial Peptide with a Cathelin–Like Pro–Sequence", *Biochemical and Biophysical Research Communications*, 196(3):1363–1368.

Tamamura et al., 1993, "Antimicrobial Activity and Conformation of Tachyplesin 1 and Its Analogs", *Chemical and Pharmaceutical Bulletin*, 41(5):978–980.

(List continued on next page.)

Primary Examiner—Michael Borin
(74) *Attorney, Agent, or Firm*—Pennie & Edmonds LLP

(57) ABSTRACT

The present invention provides a new class of broad-spectrum antimicrobial peptides effective against a wide variety of microbes, including bacteria, viruses, retroviruses, fungi, yeast and protozoa.

22 Claims, 6 Drawing Sheets

OTHER PUBLICATIONS

Tamamura et al., 1993, "A comparative study of the solution structures of tachyplesin 1 and a novel anti–HIV synthetic peptide, T22 ([Tyr$^{5,12}$,Lys$^7$]–polyphemusin ll), determined by nuclear magnetic resonance", *Biochimica et Biophysica Acta.*, 1163:209–216.

Zhao et al., 1994, "Identification of a new member of the protegrin family by cDNA cloning", *Febs Letters*, 346:285–288.

Zhao et al., 1995, "The structure of porcine protegrin genes", *Febs Letters*, 368:197–202.

Zhao et al., 1995, "Structures of genes for two cathelin–associated antimicrobial peptides: prophenin–2 and PR–39", *Febs Letters*, 376:130–134.

Tamamura et al., 1995, "Synthesis of Protegrin–Related Peptides and Their Antibacterial and Anti–human Immunodeficiency Virus Activity," *Chemical and Pharmaceutical Bulletin* 43:853–858.

* cited by examiner

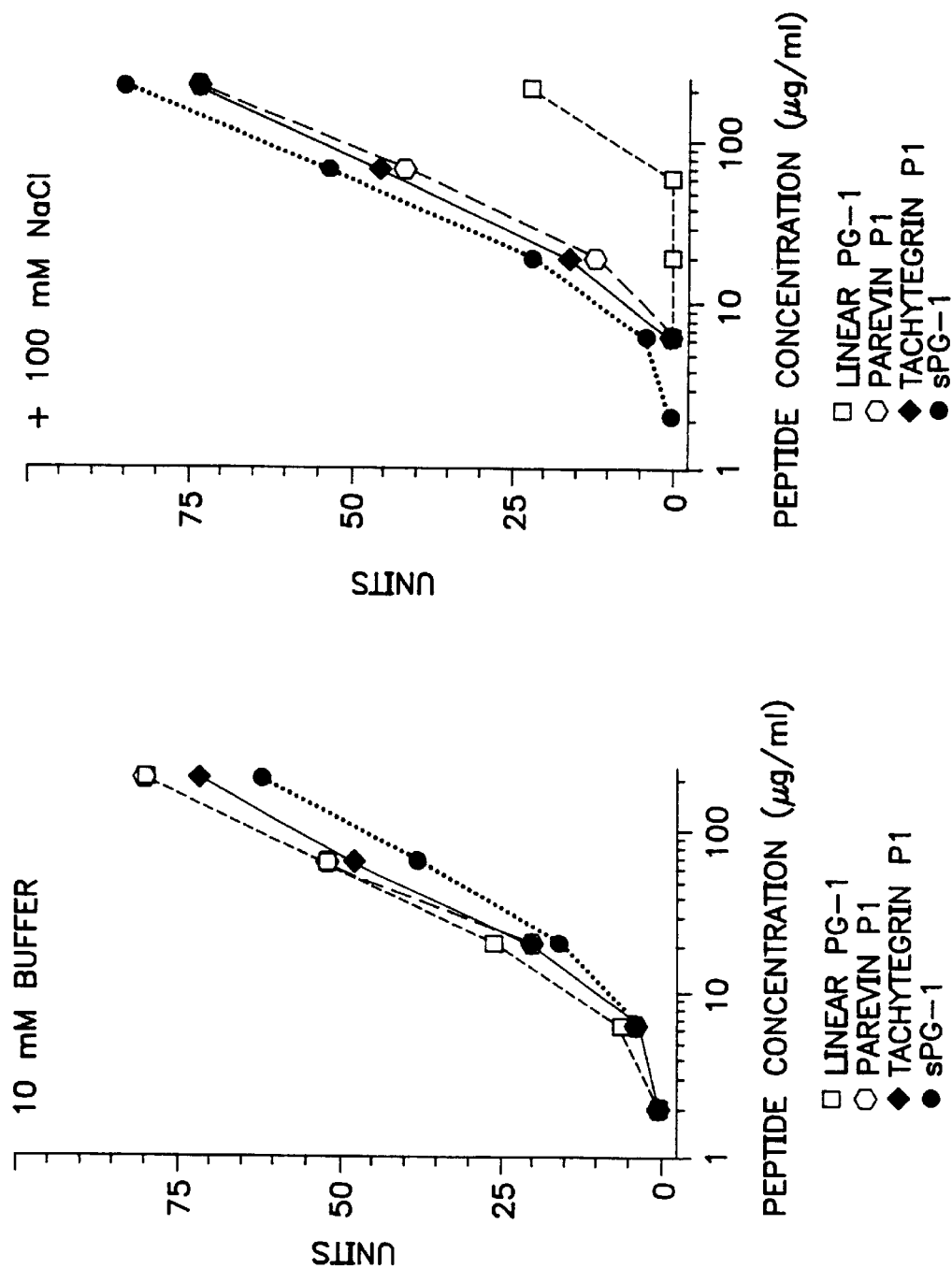

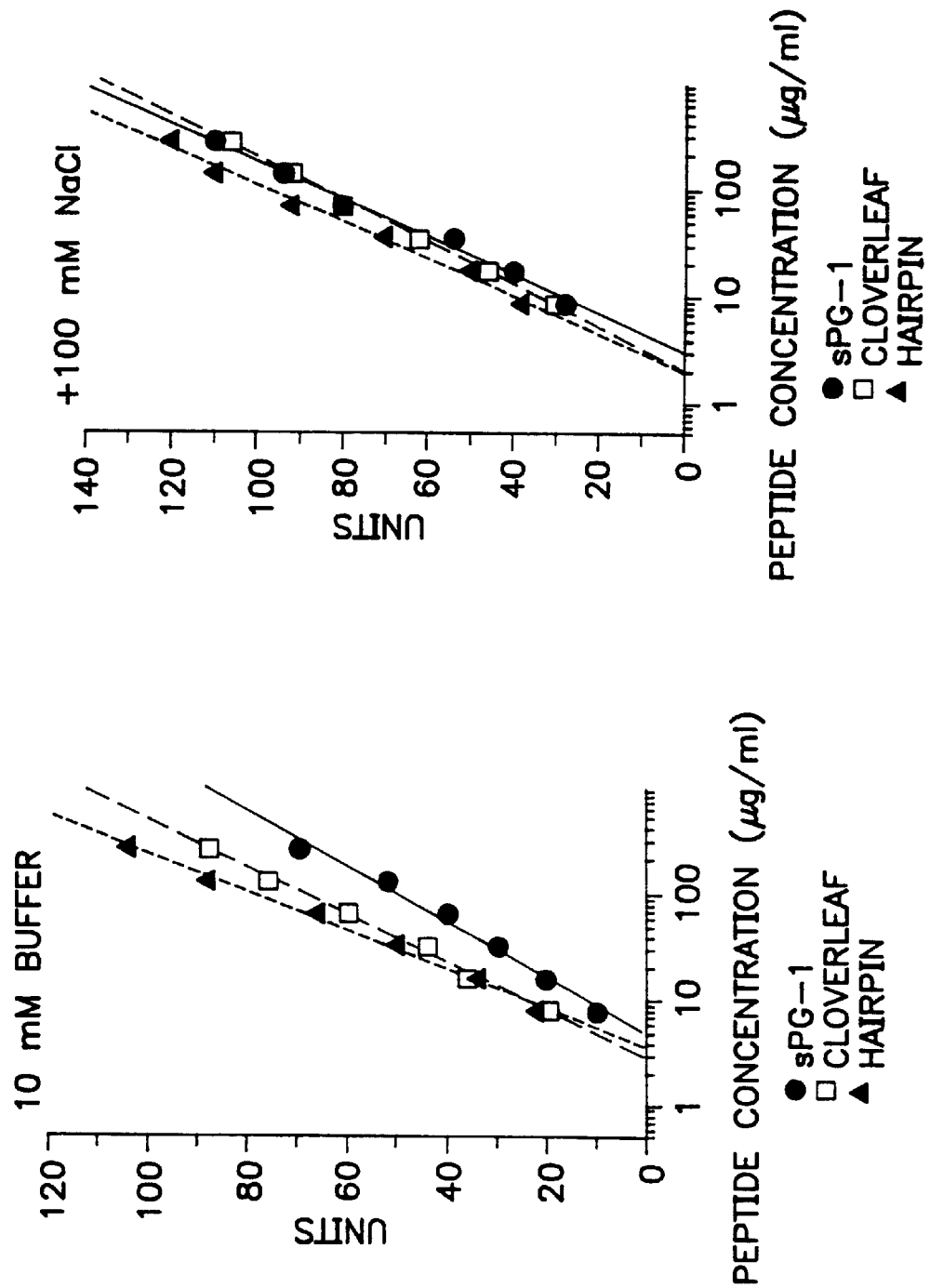

PAREVINS AND TACHYTEGRINS

CROSS-REFERENCE TO RELATED APPLICATIONS

This application is a continuation-in-part of application Ser. No. 08/674,622, filed Jul. 3, 1996 now abandoned, which is a continuation-in-part of provisional application Ser. No. 60/000,898, filed Jul. 6, 1995. The contents of these applications are hereby incorporated herein by references in their entireties.

This invention was made with funding from NIH Grant No. A122839. The U.S. Government has certain rights in this invention.

TECHNICAL FIELD

The invention relates to the field of antibiotic peptides. In particular, the invention concerns short peptides with unique patterns of cysteine type residues and conformations that have a wide range of antimicrobial activities.

BACKGROUND

One of the defense mechanisms against infection by both animals and plants is the production of peptides that have antimicrobial and antiviral activity. Various classes of these peptides have been isolated from tissues of both plants and animals. PCT application WO 95/03325 published Feb. 2, 1995 contains a review of the literature on this subject. Such peptides include tachyplesins, which are 17–18 amino acid peptides containing four invariant cysteines, the defensins, β-defensins, and insect defensins, which are somewhat longer peptides characterized by six invariant cysteines, and antifungal and antibacterial peptides and proteins which have been found in plants.

The applications in the series of which WO 95/03325 is a part provide a new class of antimicrobial and antiviral peptides, designated "protegrins", representative members of which have been isolated from porcine leukocytes. These peptides are useful as antibacterial antiviral and antifungal agents in both plants and animals.

The isolation of some of the protegrin peptides was reported in a paper by Kokryakov, V. N. et al. *FEBS* (1993) 337:231–236 (July issue). A later publication described the presence of a new protegrin, whose sequence and that of its precursor were deduced from its isolated cDNA clone. Zhao, C et al, *FEBS Letters* (1994) 346:285–288. An additional paper disclosing cationic peptides from porcine neutrophils was published by Mirgorodskaya, O. A. et al. *FEBS* (1993) 330:339–342. Storici, P. et al. *Biochem Biophys Res Comm* (1993) 196:1363–1367, report the recovery of a DNA sequence which encodes a pig leukocyte antimicrobial peptide with a cathelin-like prosequence. The peptide is reported to be one of the protegrins. Additional publications related to protegrins are Harwig, S. S. L., et al. *J Peptide Sci* (1995) in press; Zhao, C., et al. *FEBS Lett* (1995) 376:130–134; Zhao, C. et al. *FEBS Lett* (1995) 368:197–202. See also, U.S. Pat. No. 5,464,823, U.S. Pat. No. 5,696,486, WO 95/03325, WO 96/37508 and WO 98/03192.

The protegrins have also been found to bind to endotoxins—i.e., the lipopolysaccharide (LPS) compositions derived from gram-negative bacteria which are believed responsible for gram-negative sepsis. The protegrins are also effective in inhibiting the growth of organisms that are associated with sexually transmitted diseases such as *Chlamydia trachomatis* and *Neisseria gonorrhoeae*.

The invention described below relates to peptide type compounds that are related to the protegrins described above, but reflect displacements of the protegrin cysteines at positions 6 and 15. The availability of these compounds, the preferred forms of which are designated parevins and tachytegrins, expands the repertoire of antimicrobial peptides and permits more exquisite matching of indications to antimicrobial formulations. Although at least one of $C_4$, $C_5$, $C_{16}$ or $C_{17}$ in the formula set forth below must be cysteine, the common name terminology of these components reflects particularly preferred situations wherein both of $C_4$ and $C_{17}$ are cysteine type residues (the tachytegrins) or where both $C_5$ and $C_{16}$ are cysteine type residues (the parevins).

DISCLOSURE OF THE INVENTION

The invention provides compounds which retain generally the antimicrobial activity of the protegrins discussed above, but differ in conformation due to the dislocation of the cysteine residues at positions 6 and/or 15 of these protegrins. Surprisingly, these modified compounds exhibit activity spectra which are analogous to those of the protegrins, but offer the opportunity to fine-tune the biological activity of antibiotics and antivirals. All of these peptides can be produced synthetically and those that contain only gene-encoded amino acids can also be produced recombinantly. These compounds are useful as preservatives or in pharmaceutical compositions in treating or preventing infection in animals. Alternatively, the peptides can be formulated into compositions which can be applied to plants to protect them against viral or microbial infection. In still another approach, the DNA encoding the peptides can be expressed in situ, in animals or preferably in plants, to combat infections. The peptides are also useful as standards in antimicrobial assays and in binding endotoxins.

Accordingly, in one aspect, the invention is directed to a purified and isolated or recombinantly or synthetically produced compound which contains the amino acid sequence

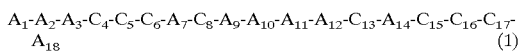

$$A_1\text{-}A_2\text{-}A_3\text{-}C_4\text{-}C_5\text{-}C_6\text{-}A_7\text{-}C_8\text{-}A_9\text{-}A_{10}\text{-}A_{11}\text{-}A_{12}\text{-}C_{13}\text{-}A_{14}\text{-}C_{15}\text{-}C_{16}\text{-}C_{17}\text{-}A_{18} \quad (1)$$

said compound containing 11–24 amino acid residues. The sequence shown as (1) can be extended at the N and/or C terminus with non-interfering amino acids or sequence.

The compounds also include the N-terminal acylated and/or C-terminal amidated or esterified forms and may be either in the, optionally—SH stabilized, linear or in a disulfide-bridged form.

In the amino acid sequence shown, each of $A_1$–$A_3$ is independently present or not present, and if present each is independently a basic, hydrophobic, polar/large, or small amino acid;

each of $C_4$, $C_5$, $C_6$, $C_{15}$, $C_{16}$ and $C_{17}$ is independently cysteine, homocysteine or penicillamine or a basic, hydrophobic, polar/large, or small amino acid, and $C_4$ and/or $C_{17}$ may be present or not present; $C_6$ and/or $C_{15}$ may also be acidic;

each of $C_8$ and $C_{13}$ is independently cysteine, homocysteine or penicillamine;

each of $A_7$ and $A_{14}$ is independently a hydrophobic or a small amino acid;

$A_9$–$A_{12}$ must be capable of effecting a or β-turn when contained in the compound and at least one of $A_9$–$A_{12}$ must be a basic amino acid;

$A_{18}$ is present or not present, and if present, is a basic, hydrophobic, polar/large or small amino acid.

The compounds of the invention may, in the alternative, contain a modified form of formula (1) wherein one or both of $C_8$ and $C_{13}$ is independently replaced by a basic, hydrophobic, polar/large, acidic, or small amino acid.

In all of the compounds of the invention at least about 15% and no more than about 50% of the amino acids must be basic amino acids, and the compounds must have a net charge of +1 at physiological pH;

with the proviso that at least one of $C_4$, $C_5$, $C_{16}$ and $C_{17}$ must be cysteine, homocysteine or penicillamine; and only one of $C_4$, $C_5$, and $C_6$, and only one of $C_{15}$, $C_{16}$ and $C_{17}$ can be cysteine, homocysteine or penicillamine.

A particular advantage of some of the peptides of the invention, especially those which contain fewer amino acids, lies in their reduced size. As a result of this, they are less costly to produce, generally are expected to provide better distribution in tissue, and are less immunogenic. As they provide alternative structures, they are likely to have different pharmacokinetic and toxicological profiles.

In still other aspects, the invention is directed to recombinant materials useful for the production of the peptides of the invention as well as plants or animals modified to contain expression systems for the production of these peptides. The invention is also directed to pharmaceutical compositions and compositions for application to plants containing the peptides of the invention as active ingredients or compositions which contain expression systems for production of the peptides or for in situ expression of the nucleotide sequence encoding these peptides. The invention is also directed to methods to prepare the invention peptides synthetically, to antibodies specific for these peptides, and to the use of the peptides as preservatives.

In other aspects, the invention is directed to the use of the compounds of the invention as standards in antimicrobial assays. The compounds many also be used as antimicrobials in solutions useful in eye care, such as contact lens solutions, and in topical or other pharmaceutical compositions for treatment of sexually transmitted diseases (STDs). The invention is also directed to use of the invention compounds as preservatives for foods or other perishables. As the invention peptides can inactivate endotoxin, the invention is also directed to a method to inactivate endotoxins using the compounds of the invention and to treat gram-negative sepsis by taking advantage of this property.

BRIEF DESCRIPTION OF THE DRAWINGS

FIGS. 3A and 3B shows antifungal activity of two of the parevins against *Candida albicans;*

FIGS. 5A and 5B shows antibacterial activity of a tachytegrin against *B. subtilis.

MODES OF CARRYING OUT THE INVENTION

Figure 1B:
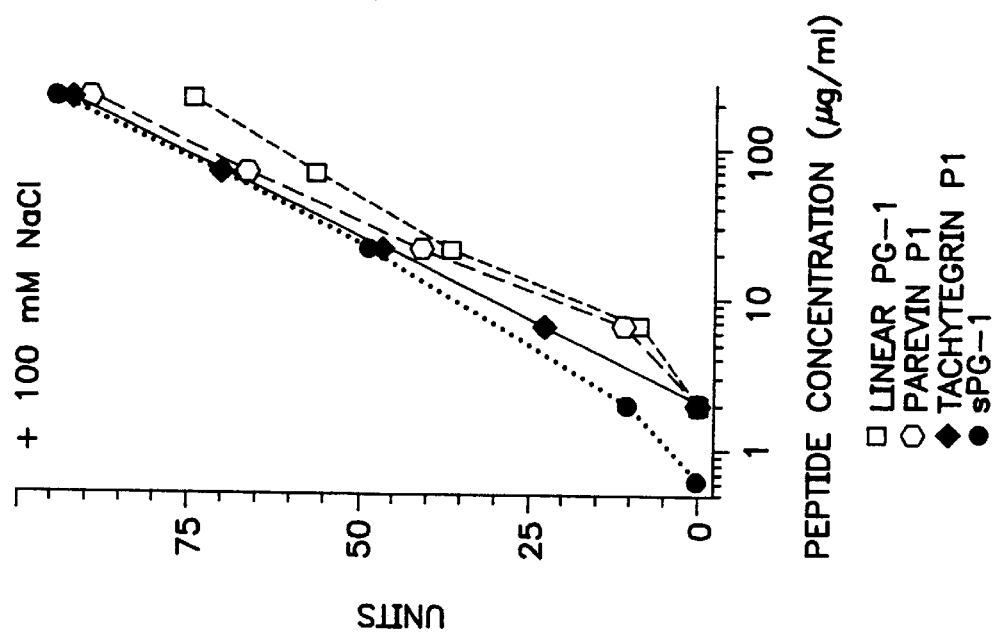
FIGS. 1A and 1B show antibacterial activity of two of the parevins against *E. coli* ML-35p.

The peptides of the invention are characterized by the amino acid sequence:

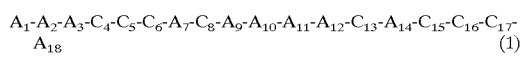

$$A_1\text{-}A_2\text{-}A_3\text{-}C_4\text{-}C_5\text{-}C_6\text{-}A_7\text{-}C_8\text{-}A_9\text{-}A_{10}\text{-}A_{11}\text{-}A_{12}\text{-}C_{13}\text{-}A_{14}\text{-}C_{15}\text{-}C_{16}\text{-}C_{17}\text{-}A_{18} \quad (1)$$

and its defined modified forms. Any of these peptides which may coincidentally occur in nature must be in purified and isolated form or prepared recombinantly or synthetically.

The designation $A_n$ in each case represents an amino acid at the specified position in the peptide. As defined, $A_1$–$A_3$, $C_4$, $C_{17}$ and/or $A_{18}$ may or may not be present. However, the peptides of the invention contain 11–24 amino acids. Thus, the sequence shown as (1) can be extended at the N and/or C terminus with non-interfering amino acids or sequence. The positions of the cysteine, homocysteine or penicillamine residues, shown as C in formula (1), are invariant in one embodiment of the peptides of the invention; however, in the modified forms of the peptides containing the sequence of formula (1), also included within the scope of the invention, one or more of these cysteines may be replaced by a small, basic acidic or hydrophobic amino acid. However, at least one of $C_4$, $C_5$, $C_{16}$ and $C_{17}$ must be cysteine, homocysteine penicillamine.

All of the peptides of the invention, however, have a net positive charge of at least +1 at physiological pH; approximately 15%–50% of the amino acid residues included in the sequence should be basic. For embodiments having as few as 11 amino acids, there may be only one basic amino acid residue; however, at least two basic residues, even in this short-chain residue, are preferred. If the peptide contains as many as 15 amino acid residues, two basic residues are required. It is preferred that at least 20% of the amino acids in the sequence be basic, more preferably 30%, but not more than 50%.

The active peptides also preferably contain a β-turn bracketed by two strands that form a β-sheet. While not intending to be bound by any theory, applicants believe that antimicrobial activity of the compounds containing the sequence of formula (1) is associated with such a β-turn bracketed by two strands that form a β-sheet structure. The amino acids $A_9$—$A_{12}$ must be capable of effecting a β-turn, which can be encouraged by the cystine bond between $C_8$ and $C_{13}$ as well as by hydrogen bonding between $A_9$ and $A_{12}$. The presence of proline at $A_{10}$ and/or $A_{11}$ does not interfere with the β-turn stabilized by the presence of a hydrophobic amino acid at positions $A_9$ or $A_{12}$.

As used herein, "β-turn" refers to a recognized sub-class of reverse-turns. Typically, a "β-turn" is a four amino acid residue peptide segment that reverses the direction of a polypeptide chain so as to allow a single polypeptide chain to adopt an anti-parallel β-sheet secondary structure. Generally, the two internal amino acid residues of the β-turn are not involved in the hydrogen-bonding of the β-sheet; the two amino acid residues on either side of the internal residues are included in the hydrogen-bonding of the J-sheet. The term "β-turn" expressly includes all types of peptide β-turns commonly known in the art including, but not limited to, type-I, type-II, type-III, type-I', type-II', and type-III'β-turns (see, Rose et al., 1985, *Adv. Protein Chem.* 37:1–109; Wilmer-White et al., 1987, *Trends Biochem. Sci.* 12:189–192; Wilmot et al., 1988, *J. Mol. Biol.* 206:759–777; Tramontano et al., 1989, *Proteins; Struct. Funct. Genet.* 6:382–394).

The presence of the four invariant cysteines of the protegrins or of the $C_8$ and $C_{13}$ cysteines, homocysteine or penicillamine of the compounds of the present invention is helpful in effecting the β-turn conformation; however, by properly choosing the substitutions, one or both of the cysteine, homocysteine or penicillamine residues at $C_8$ or $C_{13}$ can be replaced without substantially disturbing the three-dimensional shape of the molecule.

The β sheets are believed to be effected by the sequences surrounding $C_8$ and $C_{13}$, and are inclusive of these residues. Thus, in the unmodified forms of the compound, $A_7$ and $A_{14}$ are preferably hydrophobic amino acids. The cysteine residues may also, then, be replaced by other residues which do not affect the maintenance of the β sheet formation; these substitutions would include acidic, basic, hydrophobic polar or small amino acids.

The amino terminus of the peptide may be in the free amino form or may be acylated by a group of the formula RCO—, wherein R represents a hydrocarbyl group of 1–6C. The hydrocarbyl group is saturated or unsaturated and is typically, for example, methyl, ethyl, i-propyl, t-butyl, n-pentyl, cyclohexyl, cyclohexene-2-yl, hexene-3-yl, hexyne-4-yl, and the like.

The C-terminus of the peptides of the invention may be in the form of the underivatized carboxyl group, either as the free acid or an acceptable salt, such as the potassium, sodium, calcium, magnesium, or other salt of an inorganic ion or of an organic ion such as caffeine. In some embodiments, it is difficult to make salts since the remainder of the molecule bears a positive charge which may repel the relevant cation. The carboxyl terminus may also be derivatized by formation of an ester with an alcohol of the formula ROH, or may be amidated by an amine of the formula $NH_3$, or $RNH_2$, or $R_2NH$, wherein each R is independently hydrocarbyl of 1–6C as defined above. Amidated forms of the peptides wherein the C-terminus has the formula $CONH_2$ are preferred.

As the peptides of the invention contain substantial numbers of basic amino acids, the peptides of the invention may be supplied in the form of the acid addition salts. Typical acid addition salts include those of inorganic ions such as chloride, bromide, iodide, fluoride or the like, sulfate, nitrate, or phosphate, or may be salts of organic anions such as acetate, formate, benzoate and the like. The acceptability of each of such salts is dependent on the intended use, as is commonly understood.

The peptides of the invention that contain at least two cysteines, homocysteine or penicillamine may be in straight-chain or cyclic form. The straight-chain forms are convertible to the cyclic forms, and vice versa. Methods for forming disulfide bonds to create the cyclic peptides are well known in the art, as are methods to reduce disulfides to form the linear compounds. The linear compounds can be stabilized by addition of a suitable alkylating agent such as iodoacetamide.

The cyclic forms are the result of the formation of disulfide linkages among all or some of the four cysteine, homocysteine or penicillamine residues that may be present. Cyclic forms of the invention include all possible permutations of disulfide bond formation; if the—SH containing amino acids are numbered in order of their occurrence starting at the N-terminus as $C_4$, $C_5$, $C_6$, $C_8$, $C_{13}$, $C_{16}$, $C_{17}$ or $C_{18}$, these permutations include, when two disulfides are present:

a) $C_4$–$C_{17}$ and $C_8$–$C_{13}$;
b) $C_4$–$C_{16}$ and $C_8$–$C_{13}$;
c) $C_4$–$C_{15}$ and $C_8$–$C_{13}$;
d) $C_5$–$C_{17}$ and $C_8$–$C_{13}$;
e) $C_5$–$C_{16}$ and $C_8$–$C_{13}$;
f) $C_5$–$C_{15}$ and $C_8$–$C_{13}$;
g) $C_6$–$C_{17}$ and $C_8$–$C_{13}$;
h) $C_6$–$C_{16}$ and $C_8$–$C_{13}$;
i) $C_4$–$C_8$ and $C_{13}$–$C_{17}$;
j) $C_4$–$C_8$ and $C_{13}$–$C_{16}$;
k) $C_5$–$C_8$ and $C_{13}$–$C_{17}$; and
l) $C_5$–$C_8$ and $C_{13}$–$C_{16}$;

When one disulfide is present, these permutations include:

$C_4$–$C_{17}$;
$C_4$–$C_{16}$;
$C_4$–$C_{15}$;
$C_5$–$C_{17}$;
$C_5$–$C_{16}$;
$C_5$–$C_{15}$;
$C_6$–$C_{17}$;
$C_6$–$C_{16}$;
$C_8$–$C_{13}$;
$C_4$–$C_8$;
$C_5$–$C_8$;
$C_{13}$–$C_{17}$; and
$C_{13}$–$C_{16}$.

In the modified forms of the peptides, where 1 or 2 cysteines, homocysteine or penicillamine are replaced, similar permutations are available as in when 2–3 cysteines, homocysteine or penicillamine are present.

The linearalized forms of the native cyclic peptides have valuable activities, even when chemically stabilized to preserve the sulfhydryl form of cysteine, homocysteine or penicillamine for example, by reaction with iodoacetamide. The compounds of the invention also include linearalized forms which are stabilized with suitable reagents. As defined herein, "SH-stabilized" forms of the peptides of the invention contain sulfhydryl groups reacted with standard reagents to prevent reformation into disulfide linkages.

An alternative approach to providing linear forms of the invention compounds comprises use of the modified form of the peptides where residues at $C_8$ and/or $C_{13}$ are replaced by amino acids which do not form cystine linkages, in combination with stabilization of any cysteine, homocysteine or penicillamine residues at $C_4$, $C_5$, or $C_6$ and/or $C_{15}$, $C_{16}$, $C_{17}$.

Forms of the invention compounds which have only one disulfide bond are conveniently obtained by replacing the cysteine, homocysteine or penicillamine residues at $C_8$ and/or $C_3$, preferably both, with amino acids which do not form disulfide linkages.

The amino acids denoted by $A_n$ may be those encoded by the gene or analogs thereof, and may also be the D-isomers thereof. One preferred embodiment of the peptides of the invention is that form wherein all of the residues are in the D-configuration thus conferring resistance to protease activity while retaining antimicrobial or antiviral properties. The resulting peptides are enantiomers of the native L-amino acid-containing forms.

In one class of peptides described herein, either one or both of the residues found at $C_5$ and/or $C_{16}$ is a basic amino acid and/or at least one of $A_1$–$A_3$ and $C_4$ is hydrophobic and/or at least one, and preferably all four of these amino acids are deleted. By suitable manipulation of these and other features, the range of conditions under which the class of peptides of the present invention are effective can be varied. Furthermore, the spectrum of microbes against which they are effective can also be modified. This is further described hereinbelow.

The amino acid notations used herein are conventional and are as follows:

| Amino Acid | One-Letter Symbol | Three-Letter Symbol |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

The amino acids not encoded genetically are abbreviated as indicated in the discussion below.

In the specific peptides shown in the present application, the L-form of any amino acid residue having an optical isomer is intended unless the D-form is expressly indicated by a dagger superscript (`).

The compounds of the invention are peptides which are partially defined in terms of amino acid residues of designated classes. Amino acid residues can be generally subclassified into major subclasses as follows:

Acidic: The residue has a negative charge due to loss of H ion at physiological pH and the residue is attracted by aqueous solution so as to seek the surface positions in the conformation of a peptide in which it is contained when the peptide is in aqueous medium at physiological pH.

Basic: The residue has a positive charge due to association with H ion at physiological pH and the residue is attracted by aqueous solution so as to seek the surface positions in the conformation of a peptide in which it is contained when the peptide is in aqueous medium at physiological pH.

Hydrophobic: The residues are not charged at physiological pH and the residue is repelled by aqueous solution so as to seek the inner positions in the conformation of a peptide in which it is contained when the peptide is in aqueous medium.

Polar/large: The residues are not charged at physiological pH, but the residue is not sufficiently repelled by aqueous solutions so that it would seek inner positions in the conformation of a peptide in which it is contained when the peptide is in aqueous medium.

This description also characterizes certain neutral amino acids as "small" since their side chains are not sufficiently large, even if polar groups are lacking, to confer hydrophobicity. "Small" amino acids are those with four carbons or less when at least one polar group is on the side chain and three carbons or less when not.

It is understood, of course, that in a statistical collection of individual residue molecules some molecules will be charged, and some not, and there will be an attraction for or repulsion from an aqueous medium to a greater or lesser extent. To fit the definition of "charged," a significant percentage (at least approximately 25%) of the individual molecules are charged at physiological pH. The degree of attraction or repulsion required for classification as polar or nonpolar is arbitrary and, therefore, amino acids specifically contemplated by the invention have been classified as one or the other. Most amino acids not specifically named can be classified on the basis of known behavior.

Amino acid residues can be further subclassified as cyclic or noncyclic, and aromatic or nonaromatic, self-explanatory classifications with respect to the side-chain substituent groups of the residues, and as small or large. The residue is considered small if it contains a total of four carbon atoms or less, inclusive of the carboxyl carbon, provided an additional polar substituent is present; three or less if not. Small residues are, of course, always nonaromatic. For the naturally occurring protein amino acids, subclassification according to the foregoing scheme is as follows.

| | |
|---|---|
| Acidic | Aspartic acid and Glutamic acid |
| Basic | Noncyclic: Arginine, Lysine |
| | Cyclic: Histidine |
| Small | Glycine, Serine, Alanine, Threonine |
| Polar/large | Asparagine, Glutamine |
| Hydrophobic | Tyrosine, Valine, Isoleucine, Leucine, Methionine, Phenylalanine, Tryptophan |

The gene-encoded secondary amino acid proline is a special case due to its known effects on the secondary conformation of peptide chains, and is not, therefore, included in a group. Cysteine and other —SH containing amino acid residues are also not included in these classifications since their capacity to form disulfide bonds to provide secondary structure is critical in the compounds of the present invention.

Certain commonly encountered amino acids, which are not encoded by the genetic code, include, for example, β-Alanine (β-Ala), or other omega-amino acids, such as 3-aminopropionic, 2,3-diaminopropionic (2,3-diaP), 4-aminobutyric and so forth, I-aminisobutyric acid (Aib), sarcosine (Sar) or N-methyl glycine (MeGly), ornithine (Orn), citrulline (Cit), t-butylalanine (t-BuA), t-butylglycine (t-BuG), N-methylisoleucine (N-MeIle), phenylglycine (Phg), and cyclohexylalanine (Cha), norleucine (Nle), 2-naphthylalanine (2-Nal); 1,2,3,4-tetrahydroisoquinoline-3-carboxylic acid (Tic); β-2-thienylalanine (Thi); methionine sulfoxide (MSO); and homoarginine (Har). These also fall conveniently into particular categories.

Based on the above definitions,

Sar or MeGly, β-Ala, and Aib are small;

t-BuA, t-BuG, N-MeIle, Nle, Mvl, Cha, Phg, Nal, Thi and Tic are hydrophobic;

Orn, 2,3-diaP and Har are basic;

Cit, Acetyl Lys, and MSO are polar/large.

The various omega-amino acids are classified according to size as small (β-Ala and 3-aminopropionic) or as large and hydrophobic (all others).

Other amino acid substitutions of those encoded in the gene can also be included in peptide compounds within the scope of the invention and can be classified within this general scheme according to their structure.

In all of the peptides of the invention, one or more amide linkages (—CO—NH—) may optionally be replaced with another linkage which is an isostere such as —CH$_2$NH—, —CH$_2$S—, —CH$_2$CH$_2$, —CH=CH— (cis and trans), —COCH$_2$—, —CH(OH)CH$_2$— and —CH$_2$SO—. This replacement can be made by methods known in the art. The following references describe preparation of peptide analogs which include these alternative-linking moieties: Spatola, A.

F., Vega Data (March 1983), Vol. 1, Issue 3, "Peptide Backbone Modifications" (general review); Spatola, A. F., in *Chemistry and Biochemistry of Amino Acids Peptides and Proteins,* B. Weinstein, eds., Marcel Dekker, New York, p. 267 (1983) (general review); Morley, J. S., *Trends Pharm Sci* (1980) pp. 463–468 (general review); Hudson, D., et al., *Int J Pept Prot Res* (1979) 14:177–185 (—CH$_2$NH—, —CH$_2$CH$_2$—); Spatola, A. F., et al., *Life Sci* (1986) 38:1243–1249 (—CH$_2$—S); Hann, M. M., *J Chem Soc Perkin Trans I* (1982) 307–314 (—CH—CH—, cis and trans); Almquist, R. G., et al., *J Med Chem* (1980) 23:1392–1398 (—COCH$_2$—); Jennings-White, C., et al., *Tetrahedron Lett* (1982) 23:2533 (—COCH$_2$—); Szelke, M., et al., European Application EP 45665 (1982) CA:97:39405 (1982) (—CH(OH)CH$_2$—); Holladay, M. W., et al., *Tetrahedron Lett* (1983) 24:4401–4404 (—C(OH)CH$_2$—); and Hruby, V. J., *Life Sci* (1982) UB:189–199 (—CH2—S—).

In addition to analogs which contain isosteres in place of peptide linkages, the peptides or proteins of the invention include peptide mimetics in general, such as those described by Olson, G. L. et al. *J Med Chem* (1993) 36:3039–3049 and retro-inverso type peptides as described by Chorev, M. et al. *Science* (1979) 204:1210–1212; and Pallai, P. V. et al., *Int J Pept Protein Res* (1983) 21:84–92.

One class of preferred embodiments of the compounds invention includes the "unmodified" forms where positions 8 and 13 are independently cysteine, homocysteine or penicillamine residues, especially in the disulfide bonded form.

In addition, or alternatively, each of $A_7$ and $A_{14}$ is a hydrophobic acid, preferably Ile, Val, Leu, NLe, Trp, Tyr or Phe or is a small amino acid, Ala, Gly, Ser or Thr.

In another set of preferred embodiments, all of $A_1$–$A_3$ are not present or at least one, and preferably two of $A_1$14 $A_3$ is a hydrophobic amino acid, preferably Ile, Val, Leu, NLe, Trp, Tyr or Phe.

In another set of preferred embodiments, $C_4$ and/or $C_{17}$ is not present or, if present, is a cysteine, homocysteine or penicillamine or a hydrophobic amino acid, preferably Ile, Val, Leu, NLe, Trp, Tyr or Phe, or a small amino acid, preferably S, A, G or T.

In another set of preferred embodiments, $C_5$ and/or $C_{16}$ is a cysteine, homocysteine or penicillamine or a hydrophobic amino acid, preferably Ile, Val, Leu, NLe, Trp, Tyr or Phe, or a small amino acid, preferably S, A, G or T.

In another set of preferred embodiments, $A_9$–$A_{12}$ contain at least one hydrophobic amino acid residue, preferably Phe, Tyr or Trp.

Other preferred embodiments include those wherein each of $A_1$ and $A_9$ is independently selected from the group consisting of R, K and Har; more preferably, both $A_1$ and $A_9$ are R; however, each of Al may be absent.

In another class of preferred embodiments, each of $A_2$ and $A_3$ is independently selected from the group consisting of G, A, S and T; more preferably, $A_2$ and $A_3$ are G; however, $A_2$ and/or $A_3$ may be absent.

In another set of preferred embodiments, one of $A_9$ and $A_{12}$ is R, K, Har, Orn or H preferably R and the other is I, V, L, NLe, W, Y or F, preferably R, F or W, or is S, G, A or T.

In another set of preferred embodiments, each of $A_{10}$ and $A_{11}$ is independently proline or a small, basic or hydrophobic amino acid, preferably R, G, W or P.

$A_{18}$ is preferably absent, but when present, is preferably R, K or Har, most preferably R.

Also preferably when all four amino acids $A_1$–$A_3$ and $C_4$ are present, $A_1$ is basic, $C_4$ is C or basic, and $A_2$ and $A_3$ are small amino acids, or at least one of $A_1$–$A_3$ and $C_4$ is hydrophobic. Preferred embodiments of $A_1$–$A_3$ include R-G-G, K-G-S, K-S-G, and the like.

As described above, the compounds of Formula (1) are either in cyclic or noncyclic (linearalized) form or may be modified wherein 1 or 2 of the cysteines, homocysteine or penicillamine at $C_8$ and $C_{13}$ are replaced by a small, hydrophobic, or a basic amino acid residue. Such modification is preferred when compounds containing only one disulfide bond are prepared. If the linearalized forms of the compound of Formula (1) are prepared, or if linearalized forms of those modified peptides which contain at least two cysteines are prepared, it is preferred that the sulfhydryl groups be stabilized by addition of a suitable reagent. Preferred embodiments for the hydrophobic amino acid to replace cysteine, homocysteine or penicillamine residues at $C_8$ and/or $C_{13}$ are I, V, L and Nle, preferably I, V or L. Preferred small amino acids to replace the cysteine, homocysteine or penicillamine residues include G, A, S and T, more preferably G. Preferred basic amino acids are R and K.

Where the compounds of the invention have two disulfide bridges, particularly preferred are the pairs of bridges:

a) $C_5$–$C_{16}$ and $C_8$–$C_{13}$;

b) $C_5$–$C_{17}$ and $C_8$–$C_{13}$;

c) $C_5$–$C_8$ and $C_{13}$–$C_{16}$;

d) $C_4$–$C_{16}$ and $C_8$–$C_{13}$; and e) $C_4$–$C_{17}$ and $C_8$–$C_{13}$.

Especially preferred are the bridges:

$C_5$–$C_{16}$ and $C_8$–$C_{13}$; and $C_4$ –$C_{17}$ and $C_8$–$C_{13}$.

Where the compound has only one disulfide bridge, particularly preferred are:

$C_4$–$C_{17}$ or $C_5$–$C_{16}$

Particularly preferred compounds of the invention, including the N-terminal acylated and C-terminal amidated forms thereof are the parevins, wherein $C_5$ and $C_{16}$ are both cysteine, homocysteine or penicillamine and the tachytegrins wherein both $C_4$ and $C_{17}$ are cysteine, homocysteine or penicillamine. Also preferred are the disulfide forms of these compounds, cis-parevins wherein the two disulfide bridges are $C_5$–$C_8$ and $C_{13}$–$C_{16}$; the trans-parevins wherein the disulfide bridges are $C_5$–$C_{16}$ and $C_8$–$C_{13}$; and the trans-tachytegrins wherein the disulfide bridges are $C_4$–$C_{17}$ and $C_8$–$C_{13}$. Particularly preferred are the following parevins and tachytegrins:

Parevin 1 trans_____ and cis . . .

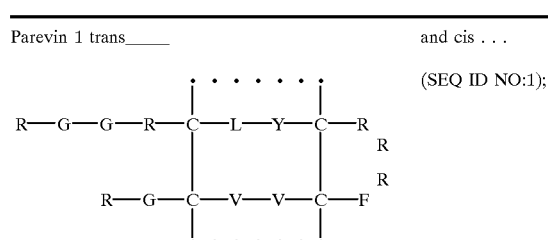

(SEQ ID NO:1);

Parevin 2 trans_____ and cis . . .

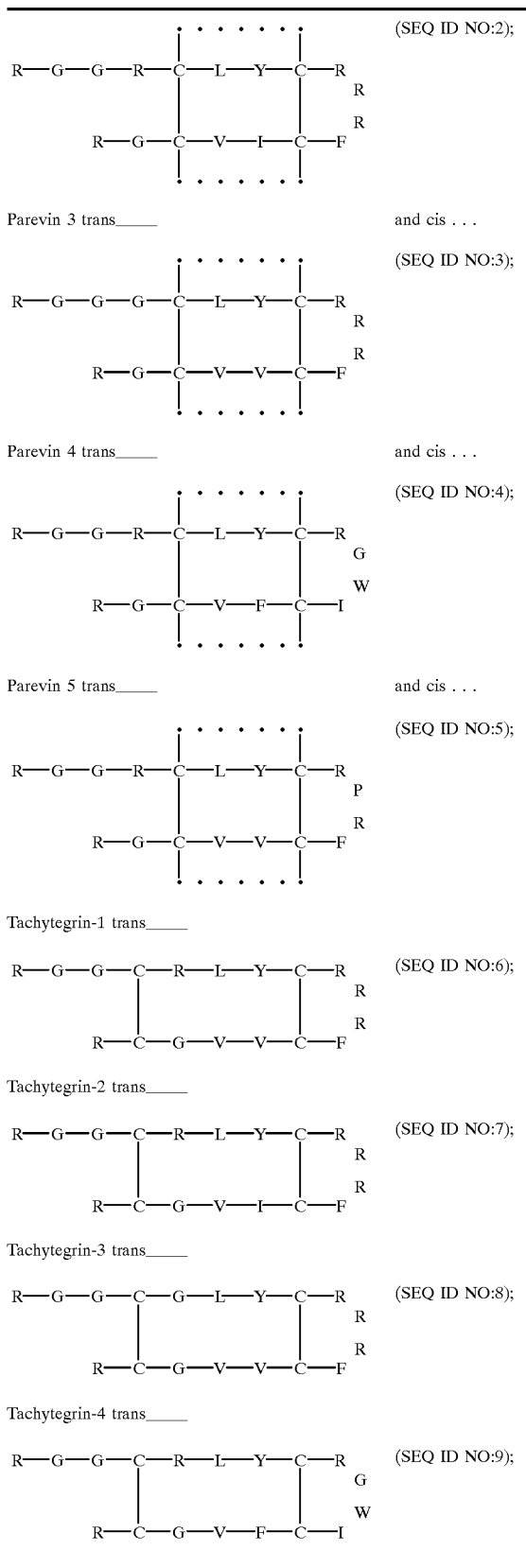
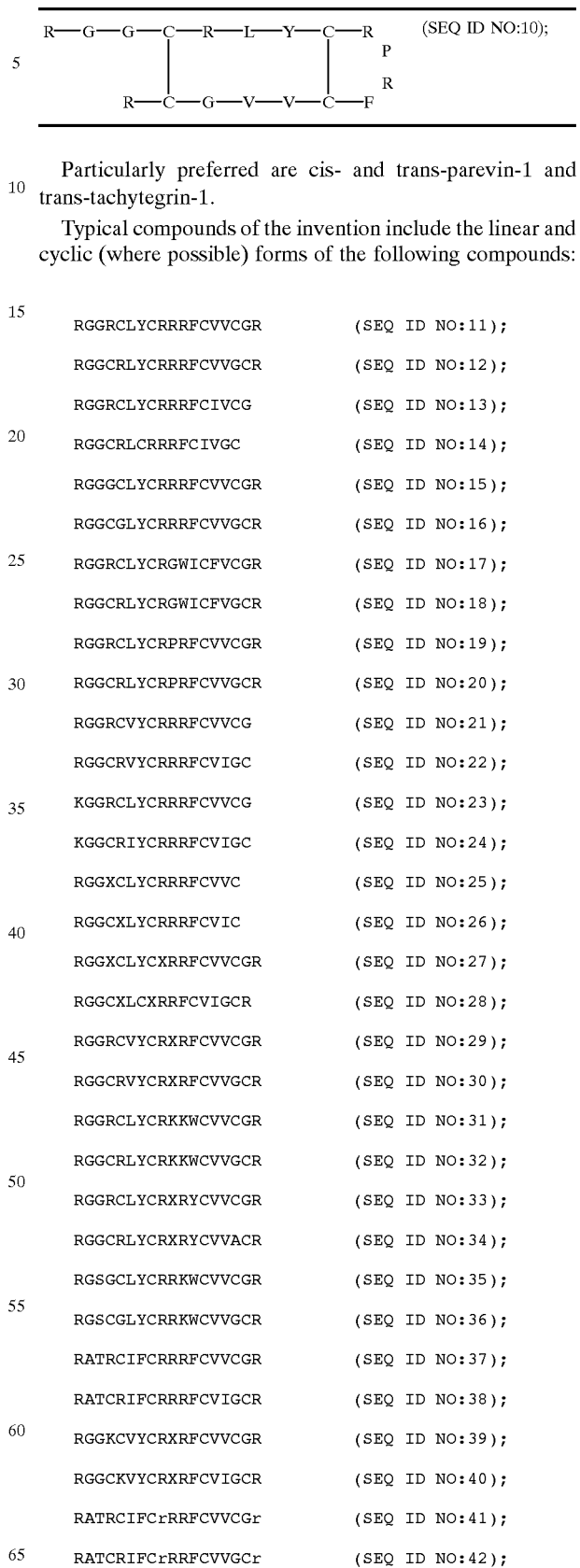

-continued (SEQ ID NO:2);

Parevin 3 trans_____ and cis . . .

(SEQ ID NO:3);

Parevin 4 trans_____ and cis . . .

(SEQ ID NO:4);

Parevin 5 trans_____ and cis . . .

(SEQ ID NO:5);

Tachytegrin-1 trans_____

(SEQ ID NO:6);

Tachytegrin-2 trans_____

(SEQ ID NO:7);

Tachytegrin-3 trans_____

(SEQ ID NO:8);

Tachytegrin-4 trans_____

(SEQ ID NO:9);

Tachytegrin-5 trans_____

-continued (SEQ ID NO:10);

Particularly preferred are cis- and trans-parevin-1 and trans-tachytegrin-1.
Typical compounds of the invention include the linear and cyclic (where possible) forms of the following compounds:
| | |
|---|---|
| RGGRCLYCRRRFCVVCGR | (SEQ ID NO:11); |
| RGGCRLYCRRRFCVVGCR | (SEQ ID NO:12); |
| RGGRCLYCRRRFCIVCG | (SEQ ID NO:13); |
| RGGCRLCRRRFCIVGC | (SEQ ID NO:14); |
| RGGGCLYCRRRFCVVCGR | (SEQ ID NO:15); |
| RGGCGLYCRRRFCVVGCR | (SEQ ID NO:16); |
| RGGRCLYCRGWICFVCGR | (SEQ ID NO:17); |
| RGGCRLYCRGWICFVGCR | (SEQ ID NO:18); |
| RGGRCLYCRPRFCVVCGR | (SEQ ID NO:19); |
| RGGCRLYCRPRFCVVGCR | (SEQ ID NO:20); |
| RGGRCVYCRRRFCVVCG | (SEQ ID NO:21); |
| RGGCRVYCRRRFCVIGC | (SEQ ID NO:22); |
| KGGRCLYCRRRFCVVCG | (SEQ ID NO:23); |
| KGGCRIYCRRRFCVIGC | (SEQ ID NO:24); |
| RGGXCLYCRRRFCVVC | (SEQ ID NO:25); |
| RGGCXLYCRRRFCVIC | (SEQ ID NO:26); |
| RGGXCLYCXRRFCVVCGR | (SEQ ID NO:27); |
| RGGCXLCXRRFCVIGCR | (SEQ ID NO:28); |
| RGGRCVYCRXRFCVVCGR | (SEQ ID NO:29); |
| RGGCRVYCRXRFCVVGCR | (SEQ ID NO:30); |
| RGGRCLYCRKKWCVVCGR | (SEQ ID NO:31); |
| RGGCRLYCRKKWCVVGCR | (SEQ ID NO:32); |
| RGGRCLYCRXRYCVVCGR | (SEQ ID NO:33); |
| RGGCRLYCRXRYCVVACR | (SEQ ID NO:34); |
| RGSGCLYCRRKWCVVCGR | (SEQ ID NO:35); |
| RGSCGLYCRRKWCVVGCR | (SEQ ID NO:36); |
| RATRCIFCRRRFCVVCGR | (SEQ ID NO:37); |
| RATCRIFCRRRFCVIGCR | (SEQ ID NO:38); |
| RGGKCVYCRXRFCVVCGR | (SEQ ID NO:39); |
| RGGCKVYCRXRFCVIGCR | (SEQ ID NO:40); |
| RATRCIFCrRRFCVVCGr | (SEQ ID NO:41); |
| RATCRIFCrRRFCVVGCr | (SEQ ID NO:42); |

-continued

```
RGGKCVYCRxRFCVVCGR          (SEQ ID NO:43);
RGGCKVYCRxRFCVVGCR          (SEQ ID NO:44);
rggrclycrrrfcvvcgr          (SEQ ID NO:45);
rggcrlycrrrfcvvgcr          (SEQ ID NO:46);
rggrclycrrrfcivcg           (SEQ ID NO:47);
rggcrlycrrrfcivgc           (SEQ ID NO:48);
rgggclycrrrfcvvcgr          (SEQ ID NO:49);
rggcglycrrrfcvvgcr          (SEQ ID NO:50);
rggrclycrgwicfvcgr          (SEQ ID NO:51);
rggcrlycrgwicfvgcr          (SEQ ID NO:52);
RGGCLRYCRPRFCVRVCR          (SEQ ID NO:53);
RGGCRLYCRRRFCVVGCR          (SEQ ID NO:54);
RGVCLRYCRGRFCVRLCR          (SEQ ID NO:55);
RGRVCLYCRGRFCVRLCFR         (SEQ ID NO:56);
RWRVCLRYCRGRFCVRLCLR        (SEQ ID NO:57);
RGWRVCLKYCRGRFCVKLCLR       (SEQ ID NO:58);
RGGRVCLRYCRGKFCVRLCLR       (SEQ ID NO:59);
RGGCLYARRRFAVVCGR           (SEQ ID NO:60);
RGGRCLYARRRFSIVC            (SEQ ID NO:61);
RGGGCLYSRRRFAVVCGR          (SEQ ID NO:62);
RGGRCLYARRRFGVVC            (SEQ ID NO:63);
KGGRCLYVRRRFIVVC            (SEQ ID NO:64);
RGGXCLYARRRFVGCV            (SEQ ID NO:65);
RGGXCLYAXRRFSVVCGR          (SEQ ID NO:66);
RGGCXLYAXRRFSVVGCR          (SEQ ID NO:67);
RGGRCVYVRXRFLVCVGR          (SEQ ID NO:68);
RGGRCLSRKKWAVSCGR           (SEQ ID NO:69);
RGGRCLYSRXRYSVICGR          (SEQ ID NO:70);
RGSGCIYCRRKWGVVGCR          (SEQ ID NO:71);
RATRCIFSRRRFSVVCGR          (SEQ ID NO:72);
RGGKCVYGRXRFSVVCGR          (SEQ ID NO:73);
RATRCIFGrRRFGVVCGr          (SEQ ID NO:74);
RGGKCVYLRxRFLVVCGR          (SEQ ID NO:75);
RGGRCVFLRPRIGVVCGR          (SEQ ID NO:76);
RGGCLRYAVPRFAVRVCR          (SEQ ID NO:77);
RGGCLRTKPKFTVRVCR           (SEQ ID NO:78);
RGGCLRYAVGRFAVRVCR          (SEQ ID NO:79);
RGGCLRYARZRFAVRVCR          (SEQ ID NO:80);
RGFCLRYTVPRFTVRFCVR         (SEQ ID NO:81);
RGFCLRYKVGRFKVRFCVR         (SEQ ID NO:82);
RGFCLRYZVGRFZVRFCVR         (SEQ ID NO:83);
RGGCLRYARZRFAVRVCR          (SEQ ID NO:84);
RGGCLRYAVGRFAVRVCR          (SEQ ID NO:85);
RGGRCLYCRRRFCVVGCR          (SEQ ID NO:86);
RGGCRLYCRRRFCVVCGR          (SEQ ID NO:87);
RGGRCLYCRRFCVCVGR           (SEQ ID NO:88);
RGGCRLYCRRRFCVCVGR          (SEQ ID NO:89);
RGGRLCYCRRRFCVVCGR          (SEQ ID NO:90);
RGGRLCYCRRRFCVVGCR          (SEQ ID NO:91);
RGGCRLYCRRRFCVVGC           (SEQ ID NO:92);
RGGCLYCRRRFCVVGC            (SEQ ID NO:93);
RGGCRLYCRRRFCVVCG           (SEQ ID NO:94);
RGGRCLYCRRRFCVCVG           (SEQ ID NO:95);
RGGCRLYCRRRFCVCVG           (SEQ ID NO:96);
RGGRLCYCRRRFCVVCG           (SEQ ID NO:97);
RGGRLCYCRRRFCVVGC           (SEQ ID NO:98);
RGGGCLYCRRRFCVVGCR          (SEQ ID NO:99);
RGGGCLYCRRRFCVCVGR          (SEQ ID NO:100);
RGGCGLYCRRRFCVCVGR          (SEQ ID NO:101);
RGGGLCYCRRRFCVVCGR          (SEQ ID NO:102);
RGGGLCYCRRRFCVVGCR          (SEQ ID NO:103);
``` and N-terminal acylated and C-terminal amidated or esterified forms thereof, where uppercase letters represent L-amino acids, lower case letters represent D-amino acids, X is Har, x is D-Har and Z is MeGly.

Particularly preferred are the cyclic forms (where possible) and C-terminal amidated forms of the above compounds, especially the cyclic forms (where possible) and C-terminal amidated forms of:

```
RGGCLRYCRPRFCVRVCR          (SEQ ID NO:53);
RGGCRLYCRRRFCVVGCR          (SEQ ID NO:54);
RGVCLRYCRGRFCVRLCR          (SEQ ID NO:55);
RGRVCLRCRGRFCVRLCFR         (SEQ ID NO:56);
RWRVCLRYCRGRFCVRLCLR        (SEQ ID NO:57);
RGWRVCLKKYCRGRFCVKLCLR      (SEQ ID NO:58);
RGGRVCLRYCRGKFCVRLCLR       (SEQ ID NO:59);
RGGCLRYAVPRFAVRVCR          (SEQ ID NO:77);
RGGCLRYTKPKFTVRVCR          (SEQ ID NO:78);
RGGCLRYAVGRFAVRVCR          (SEQ ID NO:79);
RGGCLRYARZRFAVRVCR          (SEQ ID NO:80);
RGRCLRYTVPRFTVRFCVR         (SEQ ID NO:81);
RGFCLRYKVGRFKVRFCVR         (SEQ ID NO:82);
```

-continued

```
RGFCLRYZVGRFZVRFCVR         (SEQ ID NO:83);

RGGCLRYARZRFAVRVCR          (SEQ ID NO:84); and

RGGCLRYAVGRFAVRVCR          (SEQ ID NO:85),
``` where upper and lower case letters and X and Z are as previously defined.

Preparation of the Invention Compounds

The invention compounds are essentially peptide backbones which may be modified at the N- or C-terminus and also may contain one or two cystine disulfide linkages. The peptides may first be synthesized in noncyclized form. These peptides may then be converted to the cyclic peptides if desired by standard methods of cystine bond formation. As applied to the compounds herein, "cyclic forms" refers to those forms which contain cyclic portions by virtue of the formation of disulfide linkages between cysteine residues in the peptide. If the straight-chain forms are preferred, it is preferable to stabilize the sulfhydryl groups for any peptides of the invention which contain two or more cysteine residues.

Standard methods for synthesis of peptides can be used. Most commonly used currently are solid phase synthesis techniques; indeed, automated equipment for systematically constructing peptide chains can be purchased. Solution phase synthesis can also be used but is considerably less convenient. When synthesized using these standard techniques, amino acids not encoded by the gene and D-enantiomers can be employed in the synthesis. Thus, one very practical way to obtain the compounds of the invention is to employ these standard chemical synthesis techniques.

In addition to providing the peptide backbone, the N-and/or C-terminus can be derivatized, again using conventional chemical techniques. The compounds of the invention may optionally contain an acyl group, preferably an acetyl group at the amino terminus. Methods for acetylating or, more generally, acylating, the free amino group at the N-terminus are generally known in the art; in addition, the N-terminal amino acid may be supplied in the synthesis in acylated form.

At the carboxy terminus, the carboxyl group may, of course, be present in the form of a salt; in the case of pharmaceutical compositions this will be a pharmaceutically acceptable salt. Suitable salts include those formed with inorganic ions such as $NH_4^+$, $Na^+$, $K^+$, $Mg^{++}$, $Ca^{++}$, and the like as well as salts formed with organic cations such as those of caffeine and other highly substituted amines. However, when the compound of formula 1 contains a multiplicity of basic residues, salt formation may be difficult or impossible. The carboxy terminus may also be esterified using alcohols of the formula ROH wherein R is hydrocarbyl (1–6C) as defined above. Similarly, the carboxy terminus may be amidated so as to have the formula —$CONH_2$, —CONHR, or —$CONR_2$, wherein each R is independently hydrocarbyl (1–6C) as herein defined. Techniques for esterification and amidation as well as neutralizing in the presence of base to form salts are all standard organic chemical techniques.

If the peptides of the invention are prepared under physiological conditions, the side-chain amino groups of the basic amino acids will be in the form of the relevant acid addition salts.

Formation of disulfide linkages, if desired, is conducted in the presence of mild oxidizing agents. Chemical oxidizing agents may be used, or the compounds may simply be exposed to the oxygen of the air to effect these linkages. Various methods are known in the art. Processes useful for disulfide bond formation have been described by Tam, J. P. et al., *Synthesis* (1979) 955–957; Stewart, J. M. et al., "Solid Phase Peptide Synthesis" 2d Ed. Pierce Chemical Company Rockford, Ill. (1984); Ahmed A. K. et al., *J Biol Chem* (1975) 250:8477–8482 and Pennington M. W. et al., *Peptides* 1990, E. Giralt et al., ESCOM Leiden, The Netherlands (1991) 164–166. An additional alternative is described by Kamber, B. et al., *Helv Chim Acta* (1980) 63:899–915. A method conducted on solid supports is described by Albericio *Int J Pept Protein Res* (1985) 26:92–97.

A particularly preferred method is solution oxidation using molecular oxygen. This method has been used by the inventors herein to refold the compounds of the invention.

If the peptide backbone is comprised entirely of gene-encoded amino acids, or if some portion of it is so composed, the peptide or the relevant portion may also be synthesized using recombinant DNA techniques. The DNA encoding the peptides of the invention may itself be synthesized using commercially available equipment; codon choice can be integrated into the synthesis depending on the nature of the host.

Synthesized and recombinantly produced forms of the compounds may require subsequent derivatization to modify the N- and/or C-terminus and, depending on the isolation procedure, to effect the formation of cystine bonds as described hereinabove. Depending on the host organism used for recombinant production, some or all of these conversions may already have been effected.

For recombinant production, the DNA encoding the peptides of the invention is included in an expression system which places these coding sequences under control of a suitable promoter and other control sequences compatible with an intended host cell. Types of host cells available span almost the entire range of the plant and animal kingdoms. Thus, the compounds of the invention could be produced in bacteria or yeast (to the extent that they can be produced in a nontoxic or refractile form or utilize resistant strains) as well as in animal cells, insect cells and plant cells. Indeed, modified plant cells can be used to regenerate plants containing the relevant expression systems so that the resulting transgenic plant is capable of self protection vis-à-vis these infective agents.

The compounds of the invention can be produced in a form that will result in their secretion from the host cell by fusing to the DNA encoding the peptide, a DNA encoding a suitable signal peptide, or may be produced intracellularly. They may also be produced as fusion proteins with additional amino acid sequence which may or may not need to be subsequently removed prior to the use of these compounds as antimicrobials or antivirals.

Thus, the compounds of the invention can be produced in a variety of modalities including chemical synthesis, recombinant production, isolation from natural sources, or some combination of these techniques.

Any members of the invention class which coincidentally occur naturally must be supplied in purified and isolated form. By "purified and isolated" is meant free from the environment in which the peptide normally occurs (in the case of such naturally occurring peptides) and in a form where it can be used practically. Thus, "purified and isolated" form means that the peptide is substantially pure, i.e., more than 90% pure, preferably more than 95% pure and more preferably more than 99% pure or is in a completely different context such as that of a pharmaceutical preparation.

Antibodies

Antibodies to the peptides of the invention may also be produced using standard immunological techniques for production of polyclonal antisera and, if desired, immortalizing the antibody-producing cells of the immunized host for sources of monoclonal antibody production. Techniques for producing antibodies to any substance of interest are well known. It may be necessary to enhance the immunogenicity of the substance, particularly as here, where the material is only a short peptide, by coupling the hapten to a carrier. Suitable carriers for this purpose include substances which do not themselves produce an immune response in the mammal to be administered the hapten-carrier conjugate. Common carriers used include keyhole limpet hemocyanin (KLH), diphtheria toxoid, serum albumin, and the viral coat protein of rotavirus, VP6. Coupling of the hapten to the carrier is effected by standard techniques such as contacting the carrier with the peptide in the presence of a dehydrating agent such as dicyclohexylcarbodiimide or through the use of linkers such as those available through Pierce Chemical Company, Chicago, Ill.

The peptides of the invention in immunogenic form are then injected into a suitable mammalian host and antibody titers in the serum are monitored. It should be noted, however, that some forms of the peptides require modification before they are able to raise antibodies, due to their resistance to antigen processing. For example, peptides containing two cystine bridges may be nonimmunogenic when administered without coupling to a larger carrier and may be poor immunogens even in the presence of potent adjuvants and when coupled in certain formats such as using glutaraldehyde or to KLH. Any lack of immunogenicity may therefore result from resistance to processing to a linear form that can fit in the antigen-presenting pocket of the presenting cell. Immunogenicity of these forms of the peptides can be enhanced by cleaving the disulfide bonds.

Polyclonal antisera may be harvested when titers are sufficiently high. Alternatively, antibody-producing cells of the host such as spleen cells or peripheral blood lymphocytes may be harvested and immortalized. The immortalized cells are then cloned as individual colonies and screened for the production of the desired monoclonal antibodies.

Recombinant techniques are also available for the production of antibodies, and thus, the antibodies of the invention include those that can be made by genetic engineering techniques. For example, single-chain forms, such as $F_v$ forms, chimeric antibodies, and antibodies modified to mimic those of a particular species, such as humans, can be produced using standard methods. Thus, the antibodies of the invention can be prepared by isolating or modifying the genes encoding the desired antibodies and producing these through expression in recombinant host cells, such as CHO cells.

The antibodies of the invention are, of course, useful in immunoassays for determining the amount or presence of the peptides. Such assays are essential in quality controlled production of compositions containing the peptides of the invention. In addition, the antibodies can be used to assess the efficacy of recombinant production of the peptides, as well as screening expression libraries for the presence of peptide encoding genes.

Compositions Containing the Invention Peptides and Methods of Use

The peptides of the invention are effective in inactivating a wide range of microbial and viral targets, including gram-positive and gram-negative bacteria, yeast, protozoa and certain strains of virus. Accordingly, they can be used in disinfectant compositions and as preservatives for materials such as foodstuffs, cosmetics, medicaments, or other materials containing nutrients for organisms. For use in such contexts, the peptides are supplied either as a single peptide, in admixture with several other peptides of the invention, or in admixture with additional antimicrobial agents or both. In general, as these are preservatives in this context, they are usually present in relatively low amounts, of less than 5%, by weight of the total composition, more preferably less than 1%, still more preferably less than 0.1%.

The peptides of the invention are also useful as standards in antimicrobial assays and in assays for determination of capability of test compounds to bind to endotoxins such as lipopolysaccharides.

For use as antimicrobials or antivirals for treatment of animal subjects, the peptides of the invention can be formulated as pharmaceutical or veterinary compositions. Depending on the subject to be treated, the mode of administration, and the type of treatment desired—e.g., prevention, prophylaxis, therapy; the invention peptides are formulated in ways consonant with these parameters. A summary of such techniques is found in Remington's *Pharmaceutical Sciences,* latest edition, Mack Publishing Co., Easton, Pa.

The peptides of the invention can also be used as active ingredients in pharmaceutical compositions useful in treatment of sexually transmitted diseases, including those caused by *Chlamydia trachomatis, Treponema pallidum, Neisseria gonorrhoeae, Trichomonas vaginalis,* Herpes simplex type 2 and HIV. Topical formulations are preferred and include creams, salves, oils, powders, gels and the like. Suitable topical excipient are well known in the art and can be adapted for particular uses by those of ordinary skill.

In general, for use in treatment or prophylaxis of STDs, the peptides of the invention may be used alone or in combination with other antibiotics such as erythromycin, tetracycline, macrolides, for example azithromycin and the cephalosporins. Depending on the mode of administration, the peptides will be formulated into suitable compositions to permit facile delivery to the affected areas. The tachytegrins may be used in forms containing one or two disulfide bridges or may be in linear form. In addition, use of the enantiomeric forms containing all D-amino acids may confer advantages such as resistance to those proteases, such as trypsin and chymotrypsin, to which the peptides containing L-amino acids are less resistant.

The peptides of the invention can be administered singly or as mixtures of several peptides or in combination with other pharmaceutically active components. The formulations may be prepared in a manner suitable for systemic administration or topical or local administration. Systemic formulations include those designed for injection (e.g., intramuscular, intravenous or subcutaneous injection) or may be prepared for transdermal, transmucosal, or oral administration. The formulation will generally include a diluent as well as, in some cases, adjuvants, buffers, preservatives and the like. The tachytegrins can be administered also in liposomal compositions or as microemulsions.

If administration is to be oral, the peptides of the invention must be protected from degradation in the stomach using a suitable enteric coating. This may be avoided to some extent by utilizing amino acids in the D-configuration, thus providing resistance to protease. However, the peptide is still susceptible to hydrolysis due to the acidic conditions of the stomach; thus, some degree of enteric coating may still be required.

The peptides of the invention also retain their activity against microbes in the context of borate solutions that are commonly used in eye care products. Also, it is important that the peptides retain their activity under physiological conditions including relatively high saline and in the presence of serum. In addition, the peptides are dramatically less cytotoxic with respect to the cells of higher organisms as compared with their toxicity to microbes. These properties, make them particularly suitable for in vivo and therapeutic use.

By appropriately choosing the member or members of the peptide class of the invention, it is possible to adapt the antimicrobial activity to maximize its effectiveness with respect to a particular target microbe. As used herein, "microbe" will be used to include not only yeast, bacteria, and other unicellular organisms, but also viruses. The particular peptide used can also be chosen to be advantageous in a particular context, such as low salt or physiological salt, the presence or human serum, or conditions that mimic the conditions found in blood and tissue fluids.

The peptides of the invention may also be applied to plants or to their environment to prevent virus- and microbe-induced diseases in these plants. Suitable compositions for this use will typically contain a diluent as well as a spreading agent or other ancillary agreements beneficial to the plant or to the environment.

Thus, the peptides of the invention may be used in any context wherein an antimicrobial and/or antiviral action is required. This use may be an entirely in vitro use, or the peptides may be administered to organisms.

In addition, the antimicrobial or antiviral activity may be generated in situ by administering an expression system suitable for the production of the peptides of the invention. Such expression systems can be supplied to plant and animal subjects using known techniques. For example, in animals, pox-based expression vectors can be used to generate the peptides in situ. Similarly, plant cells can be transformed with expression vectors and then regenerated into whole plants which are capable of their own production of the peptides.

The peptides of the invention are also capable of inactivating endotoxins derived from gram-negative bacteria—i.e., lipopolysaccharides (LPS) and may be used under any circumstances where inactivation of LPS is desired. One such situation is in the treatment or amelioration of gram-negative sepsis.

Conditions Relevant to Antimicrobial/Antiviral Activity

It has been stated above that as used herein "antimicrobial" activity refers to inhibition with respect both to traditional microorganisms and to viruses, although occasionally, "antimicrobial" and "antiviral" are both specifically indicated.

Media for testing antimicrobial activity are designed to mimic certain specific conditions. The standard buffer medium, medium A, uses an underlay agar with the following composition: 0.3 mg/ml of trypticase soy broth powder, 1% w/v agarose and 10 mM sodium phosphate buffer (final pH 7.4). This will be designated either "medium A" or "standard in vitro conditions" herein.

All of the remaining media contain these same components. However, in addition:

A second medium contains 100 mM NaCl in order to mimic the salt levels in blood and tissue fluids. This will be designated "medium B" or "salt medium" herein.

A third medium is supplemented with 2.5% normal human serum; however, it is of low ionic strength and thus does not mimic body fluids. This medium will be designated "medium C" or "serum-containing medium" herein.

A fourth medium contains 80% RPMI-1640, a standard tissue culture medium which contains the principal ions and amino acids found in blood and tissue fluids. In addition, it contains 2.5% normal human serum. This will be designated "medium D" or "physiological medium" herein.

Particularly preferred is the amidated form of this peptide.

Summary

The peptides of the invention therefore represent a peculiarly useful class of compounds because of the following properties:

1) They have an antimicrobial effect with respect to a broad spectrum of target microbial systems, including viruses, including retroviruses, bacteria, fungi, yeast and protozoa.

2) Their antimicrobial activity is effective under physiological conditions—i.e., physiological saline and in the presence of serum.

3) They are much less toxic to the cells of higher organisms than to microbes.

4) They can be prepared in nonimmunogenic form thus extending the number of species to which they can be administered.

5) They can be prepared in forms which are resistant to certain proteases suggesting they are antimicrobial even in lysosomes.

6) They can be prepared in forms that resist degradation when autoclaved, thus simplifying their reparation as components of pharmaceuticals.

7) They can be modified in amino acid sequence so as to optimize the specificity with respect to target.

8) They can be modified structurally so as to accommodate the conditions under which antimicrobial activity is to be exhibited.

The following examples are intended to illustrate but not to limit the invention.

EXAMPLE 1

Synthesis of the Invention Compounds

The peptides of the invention are synthesized using conventional Fmoc chemistry on solid-phase supports. The crude synthetic peptides are refolded, purified and characterized as follows.

The crude synthetic peptide is reduced by adding an amount of dithiothreitol (DTT) equal in weight to that of the synthetic peptide, which has been dissolved at 10 mg/ml in a solution containing 6M guanidine HCl, 0.5M Tris buffer and 2 mmol EDTA, pH 8.05 and incubated for 2 hours at 52° C. under nitrogen. The mixture is passed through a 0.45 um, filter, acidified with 1/20 v/v glacial acetic acid and subjected to conventional RP HPLC purification with a C18 column.

The HPLC-purified, reduced peptides are partially concentrated by vacuum centrifugation in a Speed Vac and allowed to fold for 24 hours at room temperature and air. The folding is accomplished in O.1M Tris, pH 7.7 at 0.1 mg peptide/ml to minimize formation of interchain cystine disulfides. The folded compounds are concentrated and acidified with 5% acetic acid. The purity of the final products is verified by AU-PAGE, analytical HPLC and FAB-mass spec.

Using this procedure, the compounds trans-parevin-1 (or the "hairpin" isoform), cis-parevin-1 (or "cloverleaf" isoform) and trans-tachytegrin-l were prepared. These compounds are of the formulas

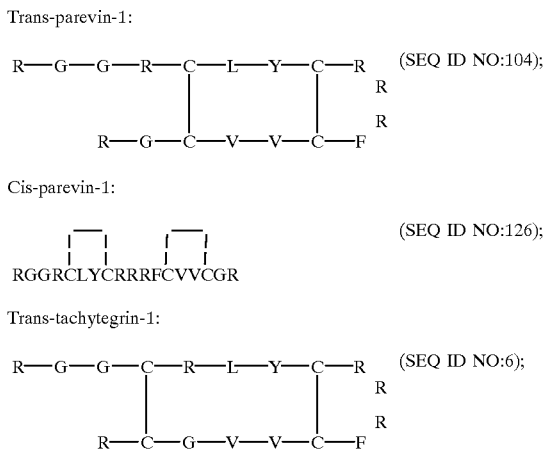

EXAMPLE 2

Antimicrobial Activity

The radial diffusion assay in agarose gels is conducted using radiodiffusion and gel overlay techniques as described by Lehrer, R. I. et al. *J Immunol Meth* (1991) 137:167–173. Briefly, the underlay agars used for all organisms had a final pH of 7.4 and contained 10 mM sodium phosphate buffer, 1% w/v agarose and 0.30 ug/ml trypticase soy broth powder (BBL Cockeysville, Md.). In some cases, the underlay was supplemented with 100 mM NaCl. The units of activity in the radial diffusion assay were measured as described; 10 units correspond to a 1 mm diameter clear zone around the sample well. FIGS. 1–6 show the results against five test organisms in units described as above. A synthetic protegrin (PG-1) containing two cystines (sPG-1) or PG-1 in linear form were used as controls.

Figure 1A:
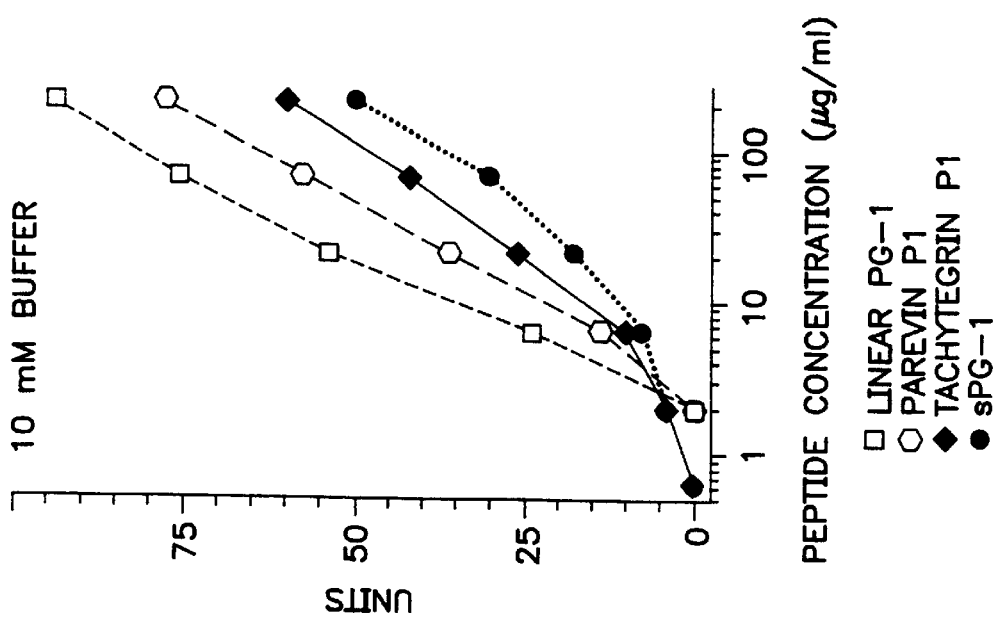

FIG. 1 shows the results for trans-parevin and tachytegrin with respect to *E. coli* both with and without the addition of 100 mM NaCl. Both of these peptides were slightly more effective than sPG-1 although slightly less effective than linear PG-1 in the absence of salt. However, in the presence of 100 mM NaCl, all four peptides were comparably effective.

Figures 2A, 2B:
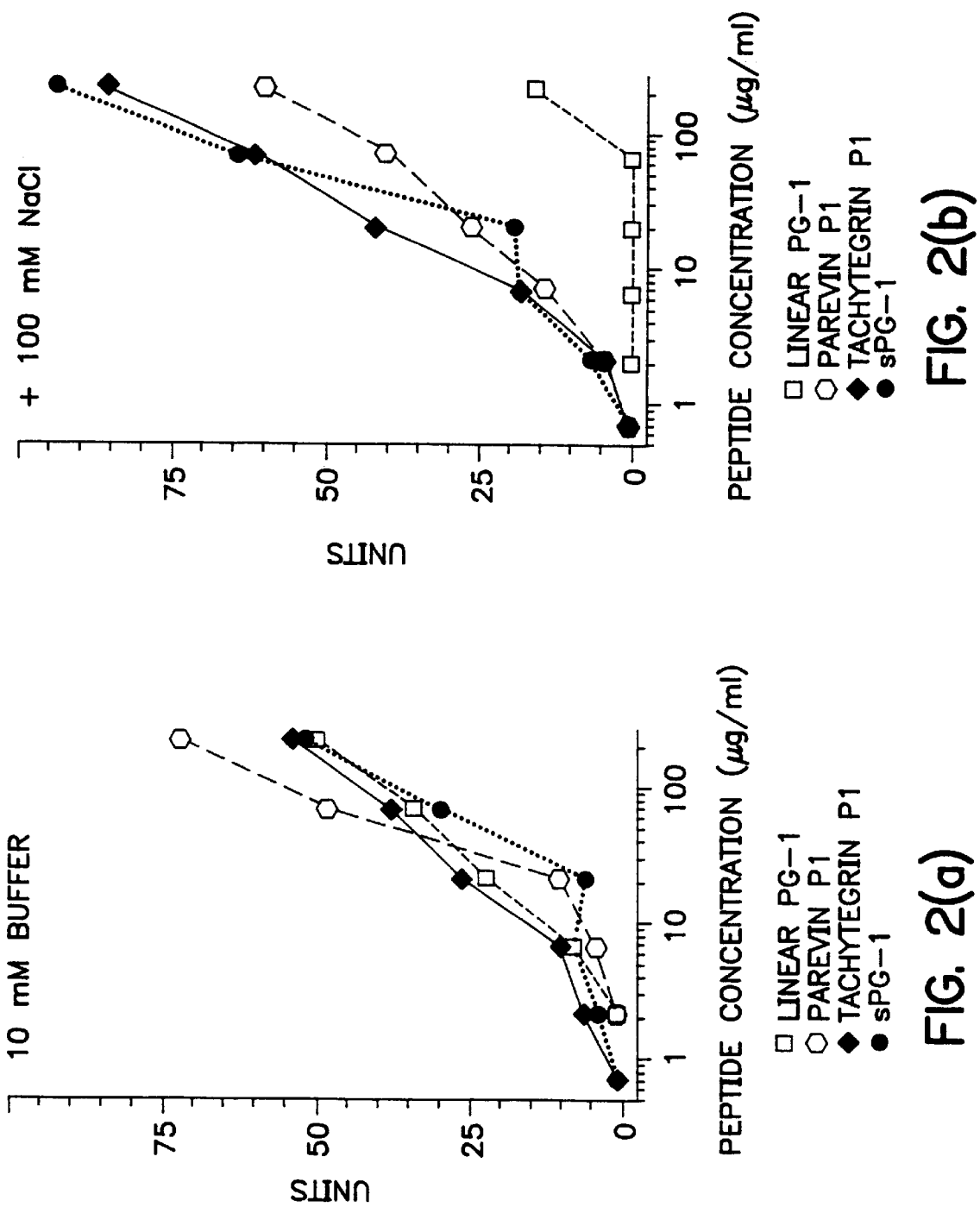
FIGS. 2A and 2B show antibacterial activity of two of the parevins against *Listeria monocytogenes;*

FIG. 2 shows the results of the same determination with respect to *L. monocytogenes*. With respect to this organism, all four peptides were roughly similarly effective in the absence of salt; the presence of 100 mM NaCl, however, greatly reduced the effectiveness of linear PG-1. The remaining three peptides remained effective under these conditions.

FIG. 3 shows the results of the same experiment using *C. albicans* as the target organism. All four peptides were comparably effective in the absence of salt; again, the effectiveness of linear PG-1 was greatly reduced in the presence of 100 mM NaCl, while the remaining three peptides maintained their effectiveness under these conditions.

Figure 4B:
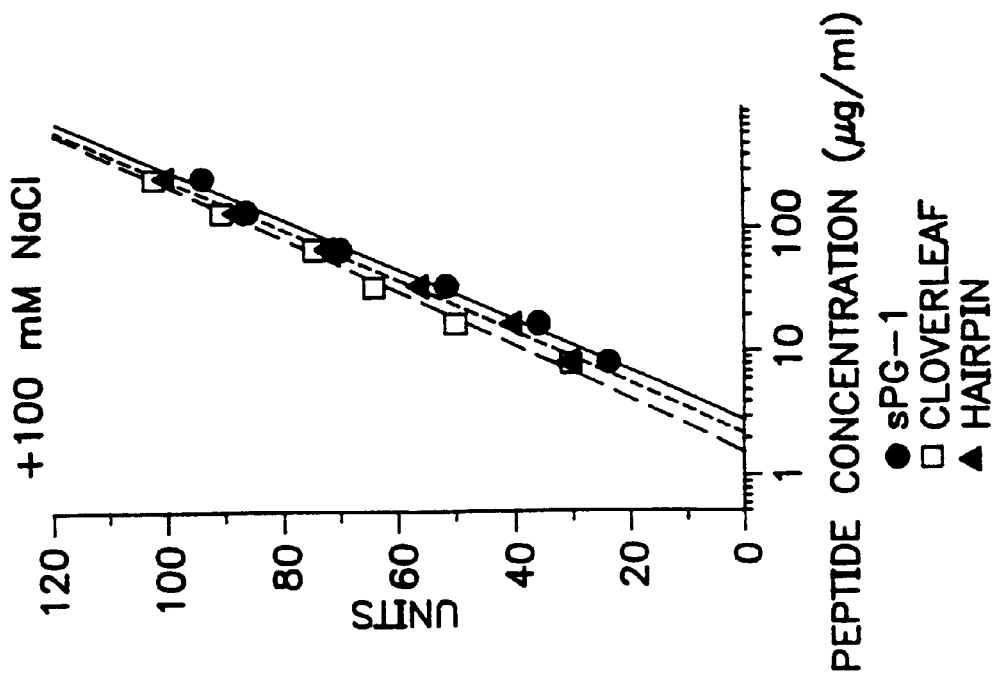
FIGS. 4A and 4B shows antibacterial activity of a tachytegrin against *E. coli* ML-35p.
Figure 4A:
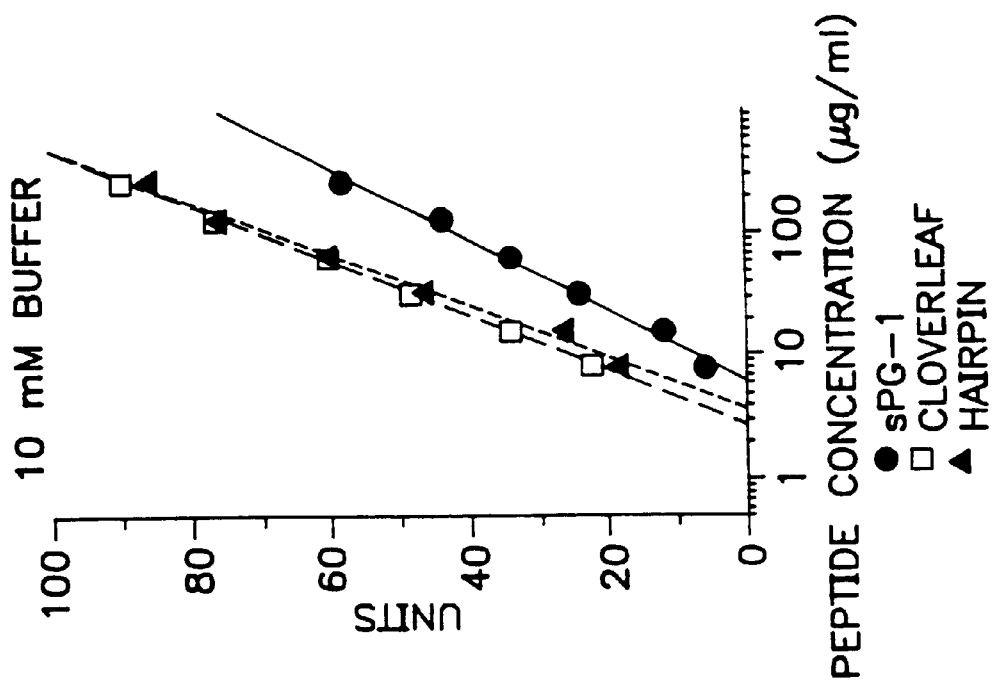
Figure 6B:
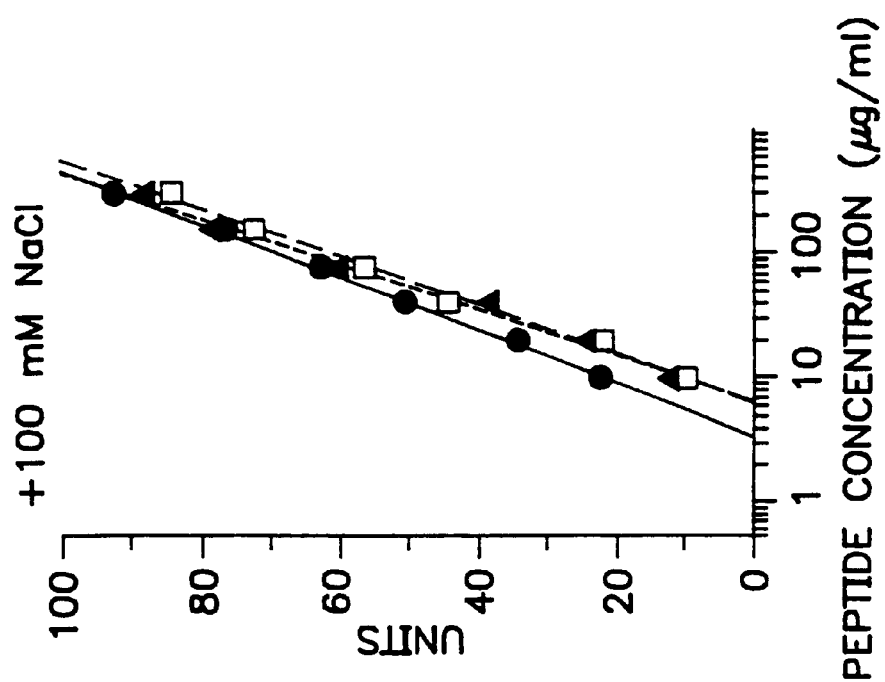
* and FIGS. 6A and 6B shows antibacterial activity of a tachytegrin against *S. typhimurium* 14028s.
Figure 6A:
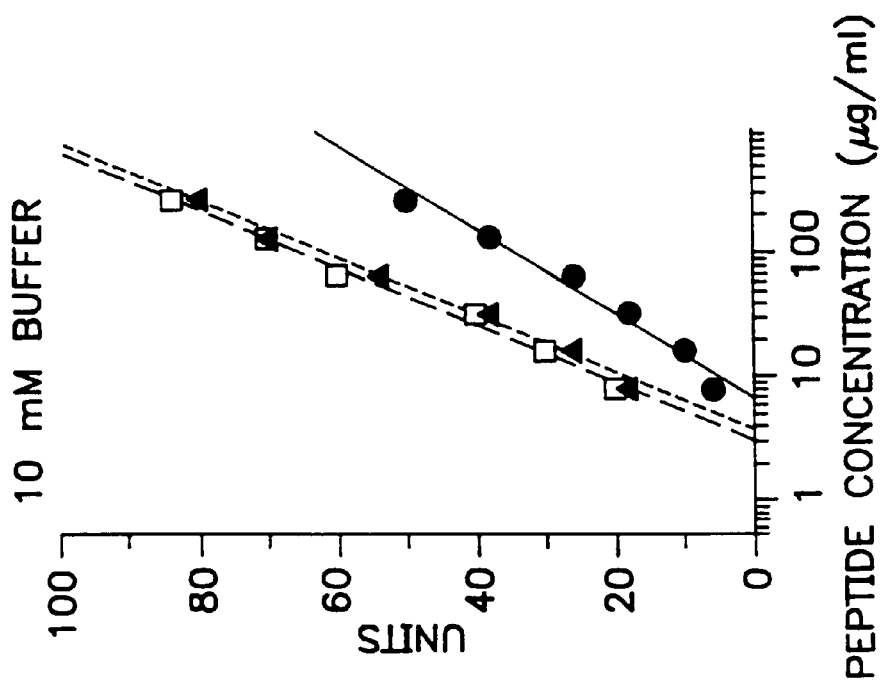

FIGS. 4–6 show the results of similar experiments using, as test peptides, the two isomers of parevin, trans-parevin (hairpin) and cis-parevin (cloverleaf). sPG-1 was used as a control. As shown in FIG. 4, the two parevins were comparably effective in the absence of salt and both were more effective than sPG-1. In the presence of 100 mM NaCl, all three peptides maintained their effectiveness and were comparable.

FIG. 5 shows results of the same experiment conducted with *B. subtilis* as target organism. Again, both forms of parevin were comparably effective and both were slightly more effective than sPG-1; in the presence of 100 mM NaCl, all three peptides remained effective antimicrobials and had about the same activity.

The results obtained with respect to *S. typhimurium* are also similar, as shown in FIG. 6. Again, the two parevins were more effective than sPG-1 in the absence of salt and all three peptides had comparable effectiveness when 100 mM NaCl was added.

EXAMPLE 3

Ability to Bind Endotoxin

The compounds of the invention are tested for their ability to bind the lipid polysaccharide (LPS) of the gram-negative bacterium *E. coli* strain 0.55B5, using the Limulus amebocyte lysate (LAL) test for endotoxins conducted in the presence and absence of the test compounds. The test is conducted using the procedure described in Sigma Technical Bulletin No. 210 as revised in December 1992 and published by Sigma Chemical Company, St. Louis, Mo.

The LAL test is based on the ability of LPS to effect gelation in the commercial reagent E-ToxateÔ which is prepared from the lysate of circulating amebocytes of the Horseshoe Crab *Limulus polyphemus*. As described in the technical bulletin, when exposed to minute quantities of LPS, the lysate increases in opacity as well as viscosity and may gel depending on the concentration of endotoxin. The technical bulletin goes on to speculate that the mechanism appears analogous to the clotting of mammalian blood and involves the steps of activation of a trypsin-like preclotting enzymes by the LPS in the presence of calcium ion, followed by enzymic modifications of a "coagulogen" by proteolysis to produce a clottable protein. These steps are believed tied to the biologically active or "pyrogenic" portion of the molecule. It has been shown previously that detoxified LPS (or endotoxin) gives a negative LAL test.

The test compounds are used at various concentrations from 0.25 ug–10 ug in a final volume of 0.2 ml and the test mixtures contained LPS at a final concentration of 0.05 endotoxin unit/ml and E-Toxate™ at the same concentration. The test compounds are incubated together with the LPS for 15 minutes before the E-Toxate™ is added to a final volume after Toxate™ addition of 0.2 ml. The tubes are then incubated for 30 minutes at 37° C. and examined for the formation of a gel.

In a follow-up experiment, the concentration of LPS is varied from 0.05–0.25 endotoxin units (E.U.).

EXAMPLE 4

Antimicrobial Activity Under Conditions Suitable for Treatment of the Eye

Contact lens solutions are typically formulated with borate buffered physiological saline and may or may not contain EDTA in addition. The compounds of the invention are tested generally in the assay described in Example 2 wherein all underlay gels contain 25 mM borate buffer, pH 7.4, 1% (v/v) trypticase soy broth (0.3 ug/ml TSB powder) and 1% agarose. Additions include either 100 mM NaCl, 1 mM EDTA or a combination thereof. Other test compounds used as controls are the defensin NP-1 and lysozyme, and dose response curves are determined.

EXAMPLE 5

Preparation of Enantio Trans-parevin

Using standard solid phase techniques, a peptide having the amino acid sequence of trans-parevin, but wherein every amino acid is in the D form is prepared. This form is tested against *E. coli, L. monocytogenes, C. albicans* and other microbes in the absence and presence of protease and otherwise as described for the radiodiffusion assay in agarose gels set forth in Example 2.

EXAMPLE 6

Activity Against STD Pathogens

The compounds of the invention are tested for antimicrobial activity against various STD pathogens. These include HIV-1, *Chlamydia trachomatis, Treponema pallidum, Neisseria gonorrhoeae, Trichomonas vaginalis,* Herpes simplex type 2, Herpes simplex type 1, *Hemophilus ducreyi,* and Human papilloma virus. The results are provided in a form wherein "active" means that the peptide is effective at less than 10 ug/ml; moderately active indicates that it is active at 10–25 ug/ml; and slightly active means activity at 25–50 ug/ml. If no effect is obtained at 50–200 ug/ml the compound is considered inactive.

The compounds of the invention are tested for their antimicrobial activity against Chlamydia using the "gold standard" chlamydial culture system for clinical specimens described by Clarke, L. M. in *Clinical Microbiology Procedures Handbook II* (1992), Isenberg, H. T. Ed. Am. Soc. Microbiol. Washington, D.C.; pp. 8.0.1 to 8.24.3.9.

In the assays, C. trachomatis serovar L2 (L2/434Bu) described by Kuo, C. C. et al. in *Nongynococcal Urethritis and Related Infections* (1977), Taylor-Robinson, D. et al. Ed. Am. Soc. Microbiol. Washington, D.C., pp. 322–326 is used. The seed is prepared from a sonicated culture in L929 mouse fibroblast cells, and partially purified by centrifugation. Since host protein is still present in the seed aliquots, each seed batch is titered at the time of preparation with serial ten-fold dilutions to $2\times10^{-9}$. The seed containing $9.2\times10^6$ IFU/ml is thawed quickly at 37° C. and diluted to 10–2 with sucrose/phosphate salts/glycine to produce IFU of about 200 after room temperature preincubation and to dilute background eukaryotic protein.

In the initial assays, the peptides to be tested are prepared as stock solutions in 0.01% glacial acetic acid. 100 ul of the diluted chlamydial seed are aliquoted into 1.5 ml eppendorf tubes and 200 ul of the antibiotic peptide was added per tube. Aliquots of the peptide stock (and controls) are incubated with the seed at room temperature for one hour, two hours and four hours. About 10 minutes before the end of each incubation period, maintenance media are aspirated from the McCoy vials in preparation for standard inoculation and culture. Culture is then performed in the presence and absence of the peptides; in some cases, the peptides are added to final concentration in the culture media in addition to the preculture incubation. The test is evaluated microscopically.

In another series of experiments, various concentrations of tachytegrin (1 ug, 12.5 ug, 25 ug and 50 ug) are used in the two-hour preincubation.

The effect of the presence of serum is also tested. The Chlamydia seed is preincubated for two hours with and without 10% FBS and also with or without test compound at 25 ug.

The experiments are repeated but adding 25 ug of compound after the start of the chlamydial culture, i.e., after centrifugation and final medium mix and one hour into the beginning of the 48-hour culture period. Finally, the compound (at 25 ug) is added to the chlamydial seed and the mix then immediately cultured.

The effect of serum is particularly important since for a topical agent to be effective in combatting Chlamydia infection, it must act in the presence of serum.

In addition, there are several mouse-based models for Chlamydia infection which can be used to assess the efficacy of the tachytegrins. These include those described by Patton, D. L. et al. in *Chlamydial Infections* (1990) Bowie, W. R. et al. Eds. Cambridge Universe providing a source of complement. Ten ul of a suspension of *T. pallidum* containing about $5\times10^7$/Ul organisms is added to each tube and the mixtures with the appropriate peptides are incubated at 34° C. under 95% $N_2$ and 5% $CO_2$. At time zero, just prior to incubation, 4 hours and 16 hours, 25 randomly selected organisms are examined for the presence or absence of motility. The 50% immobilizing end point ($IE_{50}$) is calculated to indicate the concentration needed to immobilize 50% of the spirochetes. Tachyplesin $IE_{50}$s are 5.231 ug and 2.539 ug for 0 and 4 hours, in contrast to HNP and NP preparations which show little immobilizing ability.

For Herpes Simplex Virus, using viral stocks prepared in VERO cells, grown in minimal essential medium (MEM) with 2% fetal calf serum, the effect of various peptides on HSV 1 MacIntyre strain, a pool of ten clinical HSV 1 isolates, HSV-2G, and a pool of ten clinical HSV 2 isolates, all sensitive to 3 uM acyclovir are tested. Two fibroblast cell lines, human W138 and equine CCL57, are used as targets and tests are done by direct viral neutralization and delayed peptide addition.

In the direct neutralization format, the virus is preincubated with the peptides for 90 min before it is added to the tissue culture monolayers. In the delayed peptide addition format, the virus is added and allowed 50 min to adsorb to the target cells, then the monolayers are washed and peptides are added for 90 min. Finally, the monolayer is washed to remove the peptide and the cells are fed with peptide-free MEM and cultured until the untreated infected monolayers exhibit 4+ cytopathic effect (CPE) (about 60 hours).

For *Trichomonas vaginallis,* strain C1 (ATCC 30001) is grown as described by Gorrell, T. E. et al., *Carlsberg Res Comm* (1984) 49:259–268. In experiments performed in RPMI+1% heat-activated fetal calf serum, within a few minutes after exposure to 50 ug/ml PG-1, *T. vaginallis* (heretofore vigorously motile) becomes stationary. Soon thereafter, the organisms become permeable to trypan blue, and, over the ensuing 15–30 minutes, lyse. As expected, such organisms fail to grow when introduced into their customary growth medium (Diamond's medium). Organisms exposed to 25 ug/ml of PG-3 retain their motility.

EXAMPLE 7

Antiretroviral Activity

The invention compounds are tested for antiviral activity against strains of HIV using the method described in Miles, S. A. et al., *Blood* (1991) 78:3200–3208. Briefly, the mononuclear cell fraction is recovered from normal donor leukopacs from the American Red Cross using a Ficoll-hypaque density gradient. The mononuclear cells are resuspended at $1 \times 10^6$ cells per ml in RPMI 1640 medium with 20% fetal bovine serum, 1% penn/strep with fungizone and 0.5% PHA and incubated 24 hours at 37° C. in 5% $CO_2$. The cells are centrifuged, washed and then expanded for 24 hours in growth medium.

Non-laboratory adapted, cloned $HIV_{JR-CSF}$ and $HIV_{JR-FL}$ are electroporated into the human peripheral blood mononuclear cells prepared as described above. Titers are determined and in general, multiplicities of infection (MOI) of about 4,000 infectuous units per cell are used (which corresponds to 25–40 picograms per ml HIV p24 antigen in the supernatant).

In the assay, the HIV stocks prepared as above are diluted to the correct MOI and the PBM are added to 24 well plates at a concentration of $2 \times 10^6$ per ml. One ul total volume is added to each well. The peptide to be tested is added in growth medium to achieve the final desired concentration. Then the appropriate number of MOI are added. To assay viral growth, 200 ul of supernatant is removed on days 3 and 7 and the concentration of p24 antigen is determined using a commercial assay (Coulter Immunology, Hialeah, Florida). Controls include duplicate wells containing cells alone, cells plus peptide at 5 ug/ml cells with virus but not peptide and cells with virus in the presence of AZT at $10{-}5$ $M{-}10^{-8}$ M.

The time of addition of peptide can be varied. Cells pretreated for 2 hours prior to addition of virus, at the time of addition of virus, or 2 hours after infection show antiviral activity for the peptide.

EXAMPLE 8

Preparation and Activity of Tachytegrins

Several illustrative tachytegrins were synthesized as described in Example 1 and tested for activity against *Staphylococcus aureus* (MRSA), Pseudomonas (Psa), VREF, Candida and *E.coli* as described in Example 2. The results shown in Table 1 as minimal inhibitory concentration (MIC) in ug/ml were obtained with the C-terminal amidated forms except for the last two which were tested as the free acids, as indicated by *. In all peptides in Table 1, X is MeGly.

TABLE 1

| SEQUENCE | | MRSA | Psa | VREF | Candida | E. Coli |
| --- | --- | --- | --- | --- | --- | --- |
| RGGCLRYAVPRFAVRVCR | SEQ ID NO:77 | >128 | 0.05 | | | |
| RGGCLRYTKPKFTVRVCR | SEQ ID NO:78 | | | | | |
| RGGCLRYAVGRFAVRVCR | SEQ ID NO:79 | | | | | |
| RGGCLRYARXRFAVRVCR | SEQ ID NO:80 | >32 | 5.7 | | | |
| RGFCLRYTVPRFTVRFCVR | SEQ ID NO:81 | 1.88 | 0.57 | | | 0.99 |
| RGFCLRYKVGRFKVRFVCR | SEQ ID NO:82 | >64 | 2.7 | | | |
| RGFCLRYXVGRFXVRFCVR | SEQ ID NO:83 | | | | | |
| RGGCLRYCRPRFCVRVCR | SEQ ID NO:53 | 9.8 | 0.18 | | 9.68 | 0.2 |
| RGGCRLYCRRRFCVVCGR | SEQ ID NO:54 | 53.3 | 3.3 | 4 | | 4 |
| RGVCLRYCRGRFCVRLCR | SEQ ID NO:55 | 8 | 2 | | | |
| RGRVCLRYCRGRFCVRLCFR | SEQ ID NO:56 | 6.7 | 1 | | | |
| RWRVCLRYCRGRFCVRLCLR | SEQ ID NO:57 | 4 | 4 | | | |
| RGWRVCLKYCRGRFCVKLCR | SEQ ID NO:58 | | | | | |
| RGGRVCLRYCRGKFCVRLCLR | SEQ ID NO:59 | 8 | 0.75 | | | |
| RGGCLRYAVGRFAVRVCR* | SEQ ID NO:77 | >32 | | 5.3 | | |
| RGFCLRYXVGRFXVRFCVR* | SEQ ID NO:83 | >32 | | 12 | | |

What is claimed is:

1. An antimicrobial compound composed of 11–24 amino acid residues comprising the amino acid sequence:

$$A_1-A_2-A_3-C_4-C_5-C_6-A_7-C_8-A_9-A_{10}-A_{11}-A_{12}-C_{13}-A_{14}-C_{15}-C_{16}-C_{17}-A_{18}$$

or a pharmaceutically acceptable salt or an N-terminal acylated or C-terminal amidated or esterified form thereof, wherein:

each of $A_1$–$A_3$ is independently present or not present, and if present each is independently a basic, hydrophobic, polar/large, or small amino acid;

each of $C_4$ and $C_{17}$ is independently present or not present, and if present each is independently selected from the group consisting of a thiol-containing amino acid, a basic amino acid, a hydrophobic amino acid, a polar/large amino acid and a small amino acid;

$C_5$ is selected from the group consisting of a thiol-containing amino acid, a basic amino acid, a hydrophobic amino acid, a polar/large amino acid and a small amino acid;

each of $C_8$ and $C_{13}$ is independently a thiol-containing amino acid;

each of $C_6$ and $C_{15}$ is independently selected from the group consisting of a thiol-containing amino acid, a basic amino acid, a hydrophobic amino acid, a polar/large amino acid, a small amino acid and an acidic amino acid;

$C_{16}$ is selected from the group consisting of a thiol-containing amino acid, a hydrophobic amino acid or a small amino acid;

each of $A_7$ and $A_{14}$ is independently a hydrophobic or a small amino acid;

$A_9$–$A_{12}$ taken together are capable of effecting a β-turn when contained in the compound and at least one of $A_9$–$A_{12}$ is a basic amino acid;

$A_{18}$ is present or not present, and if present, is a basic, hydrophobic, polar/large, or small amino acid;

at least about 15% to about 50% of the amino acid residues composing said compound are basic amino acids; and said compound has a net positive charge of at least +1 at physiological pH;

with the provisos that: (i) when one of $C_4$, $C_5$ or $C_6$ is a thiol-containing amino acid, the other two are other than a thiol-containing amino acid;

(ii) when one of $C_{15}$, $C_{16}$ or $C_{17}$ is a thiol-containing amino acid, the other two are other than a thiol-containing amino acid;

and (iii) the compound has one feature selected from the group consisting of:

(1) $C_4$ and $C_{15}$ are each independently a thiol-containing amino acid;

(2) $C_4$ and $C_{16}$ are each independently a thiol-containing amino acid;

(3) $C_4$ and $C_{17}$ are each independently a thiol-containing amino acid;

(4) $C_5$ and $C_{15}$ are each independently a thiol-containing amino acid;

(5) $C_5$ and $C_{16}$ are each independently a thiol-containing amino acid;

(6) $C_6$ and $C_{16}$ are each independently a thiol-containing amino acid; and (7) $C_6$ and $C_{17}$ are each independently a thiol-containing amino acid.

2. The compound of claim 1 which comprises two disulfide bridges.

3. The compound of claim 2, wherein one of said disulfide bridges links $C_5$–C16 and the other links $C_8$–$C_{13}$.

4. The compound of claim 2, wherein one of said disulfide bridges links $C_5$–$C_8$ and the other links $C_{13}$–$C_{16}$.

5. The compound of claim 2, wherein one of said disulfide bridges links $C_4$–$C_{17}$ and the other links $C_8$–$C_{13}$.

6. The compound of claim 1 in which at least one of $A_1$, $A_2$ or $A_3$ is not present.

7. The compound claim 1 in which $A_1$, $A_2$ and $A_3$ are not present.

8. The compound of claim 1 in which at least one of $A_1$, $A_2$ or $A_3$ is a hydrophobic amino acid.

9. The compound of claim 1 in which each of $C_5$ and $C_{16}$ is independently selected from the group consisting of cysteine, homocysteine, penicillamine, I, V, L, NLe, W, Y, F, A, S, G and T.

10. The compound of claim 1 in which each of $C_4$ and $C_{17}$ is independently selected from the group consisting of cysteine, homocysteine, penicillamine, I, V, L, NLe, W, Y, F, A, S, G and T.

11. The compound of claim 1 in which each of $A_7$ and $A_{14}$ is independently selected from the group consisting of I, V, L, NLe, W, Y, F, A, S, G and T.

12. The compound of claim 1 in which one of $A_9$ or $A_{12}$ is R, K, Har, Orn or H and the other is I, V, L, NLe, W, Y, F, A, S, G or T.

13. The compound of claim 1 in which all amino acids are in the D-configuration.

14. The compound of claim 1 in which $A_7$ and $A_{14}$ are each independently a hydrophobic amino acid.

15. The compound of claim 1 in which $A_9$ or $A_{12}$ is a hydrophobic amino acid or a small amino acid.

16. The compound of claim 1 in which $A_{10}$ and $A_{11}$ are each independently selected from the group consisting of proline, a basic amino acid, a hydrophobic amino acid and a small amino acid.

17. The compound of claim 1 in which $A_9$–$A_{10}$–$A_{11}$–$A_{12}$ is selected from the group consisting of: R-R-R-F, R-G-W-I, R-P-R-F, X-R-R-F, R-X-RF, R-K-K-W, R-X-R-Y, R-R-K-W, r-R-R-F, R-x-R-F, R-G-R-F, C-R-G-R, Y-C-G-R, V-P-R-F, K-P-K-F, V-G-R-F, R-P-R-I and R-Z-R-F, where X is Har, x is D-Har, Z is MeGly and r is D-Arg.

18. The compound of claim 1 which is selected from the group consisting of:

| | |
|---|---|
| RGGRCLYCRRRFCVVCGR | (SEQ ID NO:11); |
| RGGCRLYCRRRFCVVGCR | (SEQ ID NO:12); |
| RGGRCLYCRRRFCIVCG | (SEQ ID NO:13); |
| RGGCRLYCRRRFCIVGC | (SEQ ID NO:14); |
| RGGGCLYCRRRFCVVCGR | (SEQ ID NO:15); |
| RGGCGLYCRRRFCVVGCR | (SEQ ID NO:16); |
| RGGRCLYCRGWICFVCGR | (SEQ ID NO:17); |
| RGGCRLYCRGWICFVGCR | (SEQ ID NO:18); |
| RGGRCLYCRPRFCVVCGR | (SEQ ID NO:19); |
| RGGCRLYCRPRFCVVGCR | (SEQ ID NO:20); |
| RGGRCVYCRRRFCVVCG | (SEQ ID NO:21); |
| RGGCRVYCRRRFCVIGC | (SEQ ID NO:22); |
| KGGRCLYCRRRFCVVCG | (SEQ ID NO:23); |
| KGGCRIYCRRRFCVIGC | (SEQ ID NO:24); |
| RGGXCLYCRRRFCVVC | (SEQ ID NO:25); |
| RGGCXLYCRRRFCVIC | (SEQ ID NO:26); |
| RGGXCLCXRRFCVVCGR | (SEQ ID NO:27); |
| RGGCXLCXRRFCVIGCR | (SEQ ID NO:28); |
| RGGRCVYCRXRFCVVCGR | (SEQ ID NO:29); |
| RGGCRVYCRXRFCVVGCR | (SEQ ID NO:30); |
| RGGRCLYCRKKWCVVCGR | (SEQ ID NO:31); |
| RGGCRLYCRKKWCVVGCR | (SEQ ID NO:32); |
| RGGRCLYCRXRYCVVCGR | (SEQ ID NO:33); |
| RGGCRLYCRXRYCVVACR | (SEQ ID NO:34); |
| RGSGCLYCRRKWCVVCGR | (SEQ ID NO:35); |
| RGSCGLYCRRKWCVVGCR | (SEQ ID NO:36); |
| RATRCIFCRRRFCVVCGR | (SEQ ID NO:37); |
| RATCRIFCRRRFCVIGCR | (SEQ ID NO:38); |
| RGGKCVYCRXFCVVCGR | (SEQ ID NO:39); |
| RGGCKVYCRXRFCVIGCR | (SEQ ID NO:40); |
| RATRIFCrRRFCVVCGr | (SEQ ID NO:41); |
| RATCRIFCrRRFCVVGCr | (SEQ ID NO:42); |
| RGGKCVYCRxRFCVVCGR | (SEQ ID NO:43); |
| RGGCKVYCRxRFCVVGCR | (SEQ ID NO:44); |
| rggrclycrrrfcvvcgr | (SEQ ID NO:45); |
| rggcrlycrrrfcvvgcr | (SEQ ID NO:46); |
| rggrclycrrrfcivcg | (SEQ ID NO:47); |
| rggcrlycrrrfcivgc | (SEQ ID NO:48); |
| rgggclycrrrfcvvcgr | (SEQ ID NO:49); |
| rggcglycrrrfcvvgcr | (SEQ ID NO:50); |
| rggrclycrgwicfvcgr | (SEQ ID NO:51); |
| rggcrlycrgwicfvgcr | (SEQ ID NO:52); |
| RGGCLRYCRPRFCVRVCR | (SEQ ID NO:53); |
| RGGCRLYCRRRFCVVGCR | (SEQ ID NO:54); |
| RGVLRYCRGRFCVRLCR | (SEQ ID NO:55); |
| RGRVCLRYCRGRFCVRLCFR | (SEQ ID NO:56); |
| RWRVCLRYCRGRFCVRLCLR | (SEQ ID NO:57); |
| RGWRVCLKYCRGRFCVKLCLR | (SEQ ID NO:58); |
| RGGRVCLRYCRGKFCVRLCLR | (SEQ ID NO:59); |
| RGGRCLYARRRFAVVCGR | (SEQ ID NO:60); |
| RGGRCLYARRRFSIVC | (SEQ ID NO:61); |
| RGGGCLYSRRRFAVVCGR | (SEQ ID NO:62); |
| RGGRCLYARRRFGVVC | (SEQ ID NO:63); |
| KGGRCLYVRRRFIVVC | (SEQ ID NO:64); |
| RGGXCLYARRRFVGCV | (SEQ ID NO:65); |
| RGGXCLYAXRRFSVVCGR | (SEQ ID NO:66); |
| RGGCXLYAXRRFSVVGCR | (SEQ ID NO:67); |
| RGGRCVYVRXRFLVCVGR | (SEQ ID NO:68); |
| RGGRCLYSRKKWAVSCGR | (SEQ ID NO:69); |
| RGGRCLYSRXRYSVICGR | (SEQ ID NO:70); |

-continued

| | |
|---|---|
| RATRCIFSRRRFSVVCGR | (SEQ ID NO:72); |
| RGGKCVYGRXRFSVVCGR | (SEQ ID NO:73); |
| RATRCIFGrRRFGVVCGr | (SEQ ID NO:74); |
| RGGKCVYLRxRFLVVCGR | (SEQ ID NO:75); |
| RGGRCVFLRPRIGVVCGR | (SEQ ID NO:76); |
| RGGCLRYAVPRFAVRVCR | (SEQ ID NO:77); |
| RGGCLRYTKPKFTRVCR | (SEQ ID NO:78); |
| RGGCLRYAVGRFAVRVCR | (SEQ ID NO:79); |
| RGGCLRYARZRFAVRVCR | (SEQ ID NO:80); |
| RGFCLRYTVPRFTVRFCVR | (SEQ ID NO:81); |
| RGRCLRYKVGRFKRFCVR | (SEQ ID NO:82); |
| RGFCLRYZVGRFZVRFCVR | (SEQ ID NO:83); |
| RGGCLRYARZRFAVRVCR | (SEQ ID NO:84); |
| RGGCLRYAVGRFAVRVCR | (SEQ ID NO:85); |
| RGGCRLCRRRFCVVCGR | (SEQ ID NO:87); |
| RGGRCLYCRRRFCVCVGR | (SEQ ID NO:88); |
| RGGCRLCRRRFCVCVGR | (SEQ ID NO:89); |
| RGGRLCYCRRRFCVVGCR | (SEQ ID NO:90); |
| RGGRLCYCRRRFCVVGCR | (SEQ ID NO:91); |
| RGGRLCYCRRRFCVVGC | (SEQ ID NO:92); |
| RGGCRLYCRRRFCVVCG | (SEQ ID NO:94); |
| RGGRCLYCRRRFCVCVG | (SEQ ID NO:95); |
| RGGCRLYCRRRFCVCVG | (SEQ ID NO:96); |
| RGGRLCYCRRRFCVVCG | (SEQ ID NO:97); |
| RGGRLCYCRRRFCVVGC | (SEQ ID NO:98); |
| RGGGCLYCRRRFCVCVGR | (SEQ ID NO:100); |
| RGGCGLYCRRRFCVCVGR | (SEQ ID NO:101); |
| RGGGLCYCRRRFCVVCGR | (SEQ ID NO:102); |
| RGGGLCYCRRRFCVVGCR | (SEQ ID NO:103) | and the C-terminal amidated and N-terminal acylated forms thereof, wherein X is Har, x is D-Har, Z is MeGly and lower case letters represent D-amino acids.

19. The compound of claim 3 which is selected from the group consisting of:

| | |
|---|---|
| RGGRRCLYCRRRFCVVCGR | (SEQ ID NO:1); |
| RGGRCLYCRRRFCIVCG | (SEQ ID NO:13); |
| RGGGCLYCRRRFCVVCGR | (SEQ ID NO:3); |
| RGGRCLYCRGWICFVCGR | (SEQ ID NO:4); |
| RGGRCLYCRPRFCVVCGR | (SEQ ID NO:5); |
| RGGRCVYCRRRFCVVCG | (SEQ ID NO:21); |
| KGGRCLYCRRRFCVVCG | (SEQ ID NO:23); |

-continued

| | |
|---|---|
| RGGXCLYCRRRFCVVC | (SEQ ID NO:25); |
| RGGXCLYCXRRFCVVCGR | (SEQ ID NO:27); |
| RGGRCVYCRXRFCVVCGR | (SEQ ID NO:29); |
| RGGRCLYCRKKWCVVCGR | (SEQ ID NO:31); |
| RGGRCLCRXRYCVVCGR | (SEQ ID NO:33); |
| RGSGCLYCRRKWCVVCGR | (SEQ ID NO:35); |
| RATRCIFCRRRFCVVCGR | (SEQ ID NO:37); |
| RGGKCVYCRXFCVVCGR | (SEQ ID NO:39); |
| RATRCIFCrRRFCVVCGr | (SEQ ID NO:41); |
| RGGKCVYCRxRFCVVCGR | (SEQ ID NO:43); |
| rggrclycrrrfcvvcgr | (SEQ ID NO:45); |
| rggrclycrrrfcivcg | (SEQ ID NO:47); |
| rgggclycrrrfcvvcgr | (SEQ ID NO:49); |
| rggrclycrgwicfvcgr | (SEQ ID NO:51); |
| RGGRCLYCRRRFCIVCGR | (SEQ ID NO:2); | and the C-terminal amidated forms thereof, wherein X is Har, x is D-Har and lower case letters represent D-amino acids.

20. The compound of claim 4 which is selected from the group consisting of:

| | |
|---|---|
| RGGRCLYCRRRFCVVCGR | (SEQ ID NO:1); |
| RGGRCLYCRRRFCIVCG | (SEQ ID NO:13); |
| RGGGCLYCRRRFCVVCGR | (SEQ ID NO:3); |
| RGGRCLYCRGWICFVCGR | (SEQ ID NO:4); |
| RGGRCLYCRPRFCVVCGR | (SEQ ID NO:5); |
| RGGRCVYCRRRFCVVCG | (SEQ ID NO:21); |
| KGGRCLYCRRRFCVVCG | (SEQ ID NO:23); |
| RGGXCLYCRRRFCVVC | (SEQ ID NO:25); |
| RGGXCLYCXRRFCVVCGR | (SEQ ID NO:27); |
| RGGRCVYCRXRFCVVCGR | (SEQ ID NO:29); |
| RGGRCLYCRKKWCVVCGR | (SEQ ID NO:31); |
| RGGRCLYCRXRYCVVCGR | (SEQ ID NO:33); |
| RGSGCLYCRRKWCVVCGR | (SEQ ID NO:35); |
| RATRCIFCRRRFCVVCGR | (SEQ ID NO:37); |
| RGGKCVYCRXRFCVVCGR | (SEQ ID NO:39); |
| RATRCIFCrRRFCVVCGr | (SEQ ID NO:41); |
| RGGKCVYCRxRFCVVCGR | (SEQ ID NO:43); |
| rggrclycrrrfcvvcgr | (SEQ ID NO:45); |
| rggrclycrrrfcivcg | (SEQ ID NO:47); |
| rgggclycrrrfcvvcgr | (SEQ ID NO:49); |

```
rggrclycrgwicfvcgr    (SEQ ID NO:51);
RGGRCLYCRRRFCIVCGR    (SEQ ID NO:2)
``` and the C-terminal amidated forms thereof, wherein X is Har, x is D-Har and lower case letters represent D-amino acids.

21. The compound of claim 5 which is selected from the group consisting of:

```
RGGCRLYCRRRFCVVGCR    (SEQ ID NO:12);
RGGCRLYCRRRFCIVGCR    (SEQ ID NO:7);
RGGCGLYCRRRFCVVGCR    (SEQ ID NO:16);
RGGCRLYCRGWICFVGCR    (SEQ ID NO:18);
RGGCRLYCRPRFCVVGCR    (SEQ ID NO:20);
RGGCRVYCRRRFCVIGC     (SEQ ID NO:22);
KGGCRIYCRRRFCVIGC     (SEQ ID NO:24);
RGGCXLYCXRRFCVIGCR    (SEQ ID NO:28);
RGGCRVYCRXRFCVVGCR    (SEQ ID NO:30);
RGGCRLYCRKKWCVVGCR    (SEQ ID NO:32);
RGGCRLYCRXRYCVVACR    (SEQ ID NO:34);
RGSCGLYCRRKWCVVGCR    (SEQ ID NO:36);
RATCRIFCRRRFCVIGCR    (SEQ ID NO:38);
RGGCKVYCRXRFCVIGCR    (SEQ ID NO:40);
RATCRIFCrRRFCVVGCr    (SEQ ID NO:42);
RGGCKVYCRxRFCVVGCR    (SEQ ID NO:44);
rggcrlycrrrfcvvgcr    (SEQ ID NO:46);
rggcrlycrrrfcivgc     (SEQ ID NO:48);
rggcrlycrgwicfvgcr    (SEQ ID NO:52);
RGGCLRYCRPRFCVRVCR    (SEQ ID NO:53);
RGVCLRYCRGRFCVRLCR    (SEQ ID NO:55);
RGRVCLRYCRGRFCVRLCFR  (SEQ ID NO:56);
RWRVCLRYGRFCVRLCLR    (SEQ ID NO:57);
RGWRVCLKYCRGRFCVKLCLR (SEQ ID NO:58);
RGGRVCLRYCRGKFCVRLCLR (SEQ ID NO:59);
RGGCRLYCRRRFCVVGC     (SEQ ID NO:92);
RGGCRLYCRRRFCIVGC     (SEQ ID NO:14);
rggcglycrrrfcvvgcr    (SEQ ID NO:50)
``` and the C-terminal amidated forms thereof, wherein X is Har, x is D-Har and lower case letters represent D-amino acids.

22. A pharmaceutical composition comprising a compound according to claim 1 and a pharmaceutically acceptable excipient.

* * * * *

SEQUENCE LISTING

<160> NUMBER OF SEQ ID NOS: 201

<210> SEQ ID NO 1
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: DISULFID
<222> LOCATION: (5)...(8)
<223> OTHER INFORMATION: cis-Parevin 1
<221> NAME/KEY: DISULFID
<222> LOCATION: (13)...(16)
<223> OTHER INFORMATION: cis-Parevin 1
<221> NAME/KEY: DISULFID
<222> LOCATION: (5)...(16)
<223> OTHER INFORMATION: trans-Parevin 1
<221> NAME/KEY: DISULFID
<222> LOCATION: (8)...(13)
<223> OTHER INFORMATION: trans-Parevin 1

<400> SEQUENCE: 1

Arg Gly Gly Arg Cys Leu Tyr Cys Arg Arg Arg Phe Cys Val Val Cys

```
1               5               10              15
Gly Arg

<210> SEQ ID NO 2
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: DISULFID
<222> LOCATION: (5)...(8)
<223> OTHER INFORMATION: cis-Parevin 2
<221> NAME/KEY: DISULFID
<222> LOCATION: (13)...(16)
<223> OTHER INFORMATION: cis-Parevin 2
<221> NAME/KEY: DISULFID
<222> LOCATION: (5)...(16)
<223> OTHER INFORMATION: trans-Parevin 2
<221> NAME/KEY: DISULFID
<222> LOCATION: (8)...(13)
<223> OTHER INFORMATION: trans-Parevin 2

<400> SEQUENCE: 2

Arg Gly Gly Arg Cys Leu Tyr Cys Arg Arg Arg Phe Cys Ile Val Cys
1               5               10              15

Gly Arg

<210> SEQ ID NO 3
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: DISULFID
<222> LOCATION: (5)...(8)
<223> OTHER INFORMATION: cis-Parevin 3
<221> NAME/KEY: DISULFID
<222> LOCATION: (13)...(16)
<223> OTHER INFORMATION: cis-Parevin 3
<221> NAME/KEY: DISULFID
<222> LOCATION: (5)...(16)
<223> OTHER INFORMATION: trans-Parevin 3
<221> NAME/KEY: DISULFID
<222> LOCATION: (8)...(13)
<223> OTHER INFORMATION: trans-Parevin 3

<400> SEQUENCE: 3

Arg Gly Gly Gly Cys Leu Tyr Cys Arg Arg Arg Phe Cys Val Val Cys
1               5               10              15

Gly Arg

<210> SEQ ID NO 4
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: DISULFID
<222> LOCATION: (5)...(8)
<223> OTHER INFORMATION: cis-Parevin 4
<221> NAME/KEY: DISULFID
<222> LOCATION: (13)...(16)
<223> OTHER INFORMATION: cis-Parevin 4
<221> NAME/KEY: DISULFID
<222> LOCATION: (5)...(16)
<223> OTHER INFORMATION: trans-Parevin 4
<221> NAME/KEY: DISULFID
<222> LOCATION: (8)...(13)
<223> OTHER INFORMATION: trans-Parevin 4

<400> SEQUENCE: 4
```

Arg Gly Gly Arg Cys Leu Tyr Cys Arg Pro Arg Phe Cys Val Val Cys
1               5                   10                  15

Gly Arg

<210> SEQ ID NO 5
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: DISULFID
<222> LOCATION: (5)...(8)
<223> OTHER INFORMATION: cis-Parevin 5
<221> NAME/KEY: DISULFID
<222> LOCATION: (13)...(16)
<223> OTHER INFORMATION: cis-Parevin 5
<221> NAME/KEY: DISULFID
<222> LOCATION: (5)...(16)
<223> OTHER INFORMATION: trans-Parevin 5
<221> NAME/KEY: DISULFID
<222> LOCATION: (8)...(13)
<223> OTHER INFORMATION: trans-Parevin 5

<400> SEQUENCE: 5

Arg Gly Gly Arg Cys Leu Tyr Cys Arg Pro Arg Phe Cys Val Val Cys
1               5                   10                  15

Gly Arg

<210> SEQ ID NO 6
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: DISULFID
<222> LOCATION: (4)...(17)
<223> OTHER INFORMATION: trans-Tachytegrin-1
<221> NAME/KEY: DISULFID
<222> LOCATION: (8)...(13)
<223> OTHER INFORMATION: trans-Tachytegrin-1

<400> SEQUENCE: 6

Arg Gly Gly Cys Arg Leu Tyr Cys Arg Arg Arg Phe Cys Val Val Gly
1               5                   10                  15

Cys Arg

<210> SEQ ID NO 7
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: DISULFID
<222> LOCATION: (4)...(17)
<223> OTHER INFORMATION: trans-Tachytegrin-2
<221> NAME/KEY: DISULFID
<222> LOCATION: (8)...(13)
<223> OTHER INFORMATION: trans-Tachytegrin-2

<400> SEQUENCE: 7

Arg Gly Gly Cys Arg Leu Tyr Cys Arg Arg Arg Phe Cys Ile Val Gly
1               5                   10                  15

Cys Arg

<210> SEQ ID NO 8
<211> LENGTH: 18
<212> TYPE: PRT

```
<213> ORGANISM: Artificial Sequence
<220> FEATURE:
<223> OTHER INFORMATION: Synthetic polypeptide
<221> NAME/KEY: DISULFID
<222> LOCATION: (4)...(17)
<223> OTHER INFORMATION: trans-Tachytegrin-3
<221> NAME/KEY: DISULFID
<222> LOCATION: (8)...(13)
<223> OTHER INFORMATION: trans-Tachytegrin-3

<400> SEQUENCE: 8

Arg Gly Gly Cys Gly Leu Tyr Cys Arg Arg Phe Cys Val Val Gly
 1               5                  10                  15

Cys Arg

<210> SEQ ID NO 9
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: DISULFID
<222> LOCATION: (4)...(17)
<223> OTHER INFORMATION: trans-Tachytegrin-4
<221> NAME/KEY: DISULFID
<222> LOCATION: (8)...(13)
<223> OTHER INFORMATION: trans-Tachytegrin-4

<400> SEQUENCE: 9

Arg Gly Gly Cys Arg Leu Tyr Cys Arg Gly Trp Ile Cys Phe Val Gly
 1               5                  10                  15

Cys Arg

<210> SEQ ID NO 10
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: DISULFID
<222> LOCATION: (4)...(17)
<223> OTHER INFORMATION: trans-Tachytegrin-5
<221> NAME/KEY: DISULFID
<222> LOCATION: (8)...(13)
<223> OTHER INFORMATION: trans-Tachytegrin-5

<400> SEQUENCE: 10

Arg Gly Gly Cys Arg Leu Tyr Cys Arg Pro Arg Phe Cys Val Val Gly
 1               5                  10                  15

Cys Arg

<210> SEQ ID NO 11
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 11

Arg Gly Gly Arg Cys Leu Tyr Cys Arg Arg Arg Phe Cys Val Val Cys
 1               5                  10                  15

Gly Arg

<210> SEQ ID NO 12
<211> LENGTH: 18
<212> TYPE: PRT
<213> ORGANISM: Artificial Sequence
```

```
<220> FEATURE:
<223> OTHER INFORMATION: Synthetic polypeptide

<400> SEQUENCE: 12

Arg Gly Gly Cys Arg Leu Tyr Cys Arg Arg Phe Cys Val Val Gly
  1               5                  10                  15

Cys Arg

<210> SEQ ID NO 13
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 13

Arg Gly Gly Arg Cys Leu Tyr Cys Arg Arg Phe Cys Ile Val Cys
  1               5                  10                  15

Gly

<210> SEQ ID NO 14
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 14

Arg Gly Gly Cys Arg Leu Tyr Cys Arg Arg Arg Phe Cys Ile Val Gly
  1               5                  10                  15

Cys

<210> SEQ ID NO 15
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 15

Arg Gly Gly Gly Cys Leu Tyr Cys Arg Arg Phe Cys Val Val Cys
  1               5                  10                  15

Gly Arg

<210> SEQ ID NO 16
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 16

Arg Gly Gly Cys Gly Leu Tyr Cys Arg Arg Phe Cys Val Val Gly
  1               5                  10                  15

Cys Arg

<210> SEQ ID NO 17
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 17
```

Arg Gly Gly Arg Cys Leu Tyr Cys Arg Gly Trp Ile Cys Phe Val Cys
1               5                   10                  15

Gly Arg

<210> SEQ ID NO 18
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 18

Arg Gly Gly Cys Arg Leu Tyr Cys Arg Gly Trp Ile Cys Phe Val Gly
1               5                   10                  15

Cys Arg

<210> SEQ ID NO 19
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 19

Arg Gly Gly Arg Cys Leu Tyr Cys Arg Pro Arg Phe Cys Val Val Cys
1               5                   10                  15

Gly Arg

<210> SEQ ID NO 20
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 20

Arg Gly Gly Cys Arg Leu Tyr Cys Arg Pro Arg Phe Cys Val Val Gly
1               5                   10                  15

Cys Arg

<210> SEQ ID NO 21
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 21

Arg Gly Gly Arg Cys Val Tyr Cys Arg Arg Arg Phe Cys Val Val Cys
1               5                   10                  15

Gly

<210> SEQ ID NO 22
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 22

Arg Gly Gly Cys Arg Val Tyr Cys Arg Arg Arg Phe Cys Val Ile Gly
1               5                   10                  15

Cys

<210> SEQ ID NO 23
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 23

Lys Gly Gly Arg Cys Leu Tyr Cys Arg Arg Arg Phe Cys Val Val Cys
 1               5                  10                  15

Gly

<210> SEQ ID NO 24
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 24

Lys Gly Gly Cys Arg Ile Tyr Cys Arg Arg Arg Phe Cys Val Ile Gly
 1               5                  10                  15

Cys

<210> SEQ ID NO 25
<211> LENGTH: 16
<212> TYPE: PRT
<213> ORGANISM: Artificial Sequence
<220> FEATURE:
<223> OTHER INFORMATION: Synthetic polypeptide
<221> NAME/KEY: MOD_RES
<222> LOCATION: 4
<223> OTHER INFORMATION: Xaa = Homoarginine

<400> SEQUENCE: 25

Arg Gly Gly Xaa Cys Leu Tyr Cys Arg Arg Arg Phe Cys Val Val Cys
 1               5                  10                  15

<210> SEQ ID NO 26
<211> LENGTH: 16
<212> TYPE: PRT
<213> ORGANISM: Artificial Sequence
<220> FEATURE:
<223> OTHER INFORMATION: Synthetic polypeptide
<221> NAME/KEY: MOD_RES
<222> LOCATION: 5
<223> OTHER INFORMATION: Xaa = Homoarginine

<400> SEQUENCE: 26

Arg Gly Gly Cys Xaa Leu Tyr Cys Arg Arg Arg Phe Cys Val Ile Cys
 1               5                  10                  15

<210> SEQ ID NO 27
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: MOD_RES
<222> LOCATION: 4,9
<223> OTHER INFORMATION: Xaa = Homoarginine

<400> SEQUENCE: 27

Arg Gly Gly Xaa Cys Leu Tyr Cys Xaa Arg Arg Phe Cys Val Val Cys
 1               5                  10                  15

Gly Arg

```
<210> SEQ ID NO 28
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: MOD_RES
<222> LOCATION: 5,9
<223> OTHER INFORMATION: Xaa = Homoarginine

<400> SEQUENCE: 28
```

Arg Gly Gly Cys Xaa Leu Tyr Cys Xaa Arg Arg Phe Cys Val Ile Gly
 1               5                  10                  15

Cys Arg

```
<210> SEQ ID NO 29
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: MOD_RES
<222> LOCATION: 10
<223> OTHER INFORMATION: Xaa = Homoarginine

<400> SEQUENCE: 29
```

Arg Gly Gly Arg Cys Val Tyr Cys Arg Xaa Arg Phe Cys Val Val Cys
 1               5                  10                  15

Gly Arg

```
<210> SEQ ID NO 30
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: MOD_RES
<222> LOCATION: 10
<223> OTHER INFORMATION: Xaa = Homoarginine

<400> SEQUENCE: 30
```

Arg Gly Gly Cys Arg Val Tyr Cys Arg Xaa Arg Phe Cys Val Val Gly
 1               5                  10                  15

Cys Arg

```
<210> SEQ ID NO 31
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 31
```

Arg Gly Gly Arg Cys Leu Tyr Cys Arg Lys Lys Trp Cys Val Val Cys
 1               5                  10                  15

Gly Arg

```
<210> SEQ ID NO 32
<211> LENGTH: 18
<212> TYPE: PRT
<213> ORGANISM: Artificial Sequence
<220> FEATURE:
<223> OTHER INFORMATION: Synthetic polypeptide
```

<400> SEQUENCE: 32

Arg Gly Gly Cys Arg Leu Tyr Cys Arg Lys Lys Trp Cys Val Val Gly
 1               5                  10                  15

Cys Arg

<210> SEQ ID NO 33
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: MOD_RES
<222> LOCATION: 10
<223> OTHER INFORMATION: Xaa = Homoarginine

<400> SEQUENCE: 33

Arg Gly Gly Arg Cys Leu Tyr Cys Arg Xaa Arg Tyr Cys Val Val Cys
 1               5                  10                  15

Gly Arg

<210> SEQ ID NO 34
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: MOD_RES
<222> LOCATION: 10
<223> OTHER INFORMATION: Xaa = Homoarginine

<400> SEQUENCE: 34

Arg Gly Gly Cys Arg Leu Tyr Cys Arg Xaa Arg Tyr Cys Val Val Ala
 1               5                  10                  15

Cys Arg

<210> SEQ ID NO 35
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 35

Arg Gly Ser Gly Cys Leu Tyr Cys Arg Arg Lys Trp Cys Val Val Cys
 1               5                  10                  15

Gly Arg

<210> SEQ ID NO 36
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 36

Arg Gly Ser Cys Gly Leu Tyr Cys Arg Arg Lys Trp Cys Val Val Gly
 1               5                  10                  15

Cys Arg

<210> SEQ ID NO 37
<211> LENGTH: 18
<212> TYPE: PRT
<213> ORGANISM: Artificial Sequence

```
<220> FEATURE:
<223> OTHER INFORMATION: Synthetic polypeptide

<400> SEQUENCE: 37

Arg Ala Thr Arg Cys Ile Phe Cys Arg Arg Phe Cys Val Val Cys
 1               5                  10                  15

Gly Arg

<210> SEQ ID NO 38
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 38

Arg Ala Thr Cys Arg Ile Phe Cys Arg Arg Phe Cys Val Ile Gly
 1               5                  10                  15

Cys Arg

<210> SEQ ID NO 39
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: MOD_RES
<222> LOCATION: 10
<223> OTHER INFORMATION: Xaa = Homoarginine

<400> SEQUENCE: 39

Arg Gly Gly Lys Cys Val Tyr Cys Arg Xaa Arg Phe Cys Val Val Cys
 1               5                  10                  15

Gly Arg

<210> SEQ ID NO 40
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: MOD_RES
<222> LOCATION: 10
<223> OTHER INFORMATION: Xaa = Homoarginine

<400> SEQUENCE: 40

Arg Gly Gly Cys Lys Val Tyr Cys Arg Xaa Arg Phe Cys Val Ile Gly
 1               5                  10                  15

Cys Arg

<210> SEQ ID NO 41
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: MOD_RES
<222> LOCATION: 9,18
<223> OTHER INFORMATION: Xaa = D-Arginine

<400> SEQUENCE: 41

Arg Ala Thr Arg Cys Ile Phe Cys Xaa Arg Phe Cys Val Val Cys
 1               5                  10                  15

Gly Xaa
```

```
<210> SEQ ID NO 42
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: MOD_RES
<222> LOCATION: 9,18
<223> OTHER INFORMATION: Xaa = D-Arginine

<400> SEQUENCE: 42

Arg Ala Thr Cys Arg Ile Phe Cys Xaa Arg Arg Phe Cys Val Val Gly
 1               5                  10                  15

Cys Xaa

<210> SEQ ID NO 43
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: MOD_RES
<222> LOCATION: 10
<223> OTHER INFORMATION: Xaa = D-Homoarginine

<400> SEQUENCE: 43

Arg Gly Gly Lys Cys Val Tyr Cys Arg Xaa Arg Phe Cys Val Val Cys
 1               5                  10                  15

Gly Arg

<210> SEQ ID NO 44
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: MOD_RES
<222> LOCATION: 10
<223> OTHER INFORMATION: Xaa = D-Homoarginine

<400> SEQUENCE: 44

Arg Gly Gly Cys Lys Val Tyr Cys Arg Xaa Arg Phe Cys Val Val Gly
 1               5                  10                  15

Cys Arg

<210> SEQ ID NO 45
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: MOD_RES
<222> LOCATION: (1)...(18)
<223> OTHER INFORMATION: All genetically encoded amino acids are in the
      D-configuration

<400> SEQUENCE: 45

Arg Gly Gly Arg Cys Leu Tyr Cys Arg Arg Arg Phe Cys Val Val Cys
 1               5                  10                  15

Gly Arg

<210> SEQ ID NO 46
<211> LENGTH: 18
<212> TYPE: PRT
<213> ORGANISM: Artificial Sequence
<220> FEATURE:
```

<223> OTHER INFORMATION: Synthetic polypeptide
<221> NAME/KEY: MOD_RES
<222> LOCATION: (1)...(18)
<223> OTHER INFORMATION: All genetically encoded amino acids are in the
      D-configuration

<400> SEQUENCE: 46

Arg Gly Gly Cys Arg Leu Tyr Cys Arg Arg Arg Phe Cys Val Val Gly
 1               5                  10                  15

Cys Arg

<210> SEQ ID NO 47
<211> LENGTH: 17
<212> TYPE: PRT
<213> ORGANISM: Artificial Sequence
<220> FEATURE:
<223> OTHER INFORMATION: Synthetic polypeptide
<221> NAME/KEY: MOD_RES
<222> LOCATION: (1)...(17)
<223> OTHER INFORMATION: All genetically encoded amino acids are in the
      D-configuration

<400> SEQUENCE: 47

Arg Gly Gly Arg Cys Leu Tyr Cys Arg Arg Arg Phe Cys Ile Val Cys
 1               5                  10                  15

Gly

<210> SEQ ID NO 48
<211> LENGTH: 17
<212> TYPE: PRT
<213> ORGANISM: Artificial Sequence
<220> FEATURE:
<223> OTHER INFORMATION: Synthetic polypeptide
<221> NAME/KEY: MOD_RES
<222> LOCATION: (1)...(17)
<223> OTHER INFORMATION: All genetically encoded amino acids are in the
      D-configuration

<400> SEQUENCE: 48

Arg Gly Gly Cys Arg Leu Tyr Cys Arg Arg Arg Phe Cys Ile Val Gly
 1               5                  10                  15

Cys

<210> SEQ ID NO 49
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: MOD_RES
<222> LOCATION: (1)...(18)
<223> OTHER INFORMATION: All genetically encoded amino acids are in the
      D-configuration

<400> SEQUENCE: 49

Arg Gly Gly Gly Cys Leu Tyr Cys Arg Arg Arg Phe Cys Val Val Cys
 1               5                  10                  15

Gly Arg

<210> SEQ ID NO 50
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: MOD_RES
<222> LOCATION: (1)...(18)

```
<223> OTHER INFORMATION: All genetically encoded amino acids are in the
      D-configuration

<400> SEQUENCE: 50

Arg Gly Gly Cys Gly Leu Tyr Cys Arg Arg Arg Phe Cys Val Val Gly
 1               5                  10                  15

Cys Arg

<210> SEQ ID NO 51
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: MOD_RES
<222> LOCATION: (1)...(18)
<223> OTHER INFORMATION: All genetically encoded amino acids are in the
      D-configuration

<400> SEQUENCE: 51

Arg Gly Gly Arg Cys Leu Tyr Cys Arg Gly Trp Ile Cys Phe Val Cys
 1               5                  10                  15

Gly Arg

<210> SEQ ID NO 52
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: MOD_RES
<222> LOCATION: (1)...(18)
<223> OTHER INFORMATION: All genetically encoded amino acids are in the
      D-configuration

<400> SEQUENCE: 52

Arg Gly Gly Cys Arg Leu Tyr Cys Arg Gly Trp Ile Cys Phe Val Gly
 1               5                  10                  15

Cys Arg

<210> SEQ ID NO 53
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 53

Arg Gly Gly Cys Leu Arg Tyr Cys Arg Pro Arg Phe Cys Val Arg Val
 1               5                  10                  15

Cys Arg

<210> SEQ ID NO 54
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 54

Arg Gly Gly Cys Arg Leu Tyr Cys Arg Arg Arg Phe Cys Val Val Gly
 1               5                  10                  15

Cys Arg
```

```
<210> SEQ ID NO 55
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 55

Arg Gly Val Cys Leu Arg Tyr Cys Arg Gly Arg Phe Cys Val Arg Leu
 1               5                  10                  15

Cys Arg

<210> SEQ ID NO 56
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 56

Arg Gly Arg Val Cys Leu Arg Tyr Cys Arg Gly Arg Phe Cys Val Arg
 1               5                  10                  15

Leu Cys Phe Arg
            20

<210> SEQ ID NO 57
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 57

Arg Trp Arg Val Cys Leu Arg Tyr Cys Arg Gly Arg Phe Cys Val Arg
 1               5                  10                  15

Leu Cys Leu Arg
            20

<210> SEQ ID NO 58
<211> LENGTH: 21
<212> TYPE: PRT
<213> ORGANISM: Artificial Sequence
<220> FEATURE:
<223> OTHER INFORMATION: Synthetic polypeptide

<400> SEQUENCE: 58

Arg Gly Trp Arg Val Cys Leu Lys Tyr Cys Arg Gly Arg Phe Cys Val
 1               5                  10                  15

Lys Leu Cys Leu Arg
            20

<210> SEQ ID NO 59
<211> LENGTH: 21
<212> TYPE: PRT
<213> ORGANISM: Artificial Sequence
<220> FEATURE:
<223> OTHER INFORMATION: Synthetic polypeptide

<400> SEQUENCE: 59

Arg Gly Gly Arg Val Cys Leu Arg Tyr Cys Arg Gly Lys Phe Cys Val
 1               5                  10                  15

Arg Leu Cys Leu Arg
            20
```

```
<210> SEQ ID NO 60
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 60

Arg Gly Gly Arg Cys Leu Tyr Ala Arg Arg Phe Ala Val Val Cys
 1               5                  10                  15

Gly Arg

<210> SEQ ID NO 61
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 61

Arg Gly Gly Arg Cys Leu Tyr Ala Arg Arg Phe Ser Ile Val Cys
 1               5                  10                  15

<210> SEQ ID NO 62
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 62

Arg Gly Gly Gly Cys Leu Tyr Ser Arg Arg Phe Ala Val Val Cys
 1               5                  10                  15

Gly Arg

<210> SEQ ID NO 63
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 63

Arg Gly Gly Arg Cys Leu Tyr Ala Arg Arg Phe Gly Val Val Cys
 1               5                  10                  15

<210> SEQ ID NO 64
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 64

Lys Gly Gly Arg Cys Leu Tyr Val Arg Arg Phe Ile Val Val Cys
 1               5                  10                  15

<210> SEQ ID NO 65
<211> LENGTH: 16
<212> TYPE: PRT
<213> ORGANISM: Artificial Sequence
<220> FEATURE:
<223> OTHER INFORMATION: Synthetic polypeptide
<221> NAME/KEY: MOD_RES
<222> LOCATION: 4
<223> OTHER INFORMATION: Xaa = Homoarginine
```

-continued

```
<400> SEQUENCE: 65

Arg Gly Gly Xaa Cys Leu Tyr Ala Arg Arg Arg Phe Val Gly Cys Val
 1               5                  10                  15

<210> SEQ ID NO 66
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: MOD_RES
<222> LOCATION: 4,9
<223> OTHER INFORMATION: Xaa = Homoarginine

<400> SEQUENCE: 66

Arg Gly Gly Xaa Cys Leu Tyr Ala Xaa Arg Arg Phe Ser Val Val Cys
 1               5                  10                  15

Gly Arg

<210> SEQ ID NO 67
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: MOD_RES
<222> LOCATION: 5,9
<223> OTHER INFORMATION: Xaa = Homoarginine

<400> SEQUENCE: 67

Arg Gly Gly Cys Xaa Leu Tyr Ala Xaa Arg Arg Phe Ser Val Val Gly
 1               5                  10                  15

Cys Arg

<210> SEQ ID NO 68
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: MOD_RES
<222> LOCATION: 10
<223> OTHER INFORMATION: Xaa = Homoarginine

<400> SEQUENCE: 68

Arg Gly Gly Arg Cys Val Tyr Val Arg Xaa Arg Phe Leu Val Cys Val
 1               5                  10                  15

Gly Arg

<210> SEQ ID NO 69
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 69

Arg Gly Gly Arg Cys Leu Tyr Ser Arg Lys Lys Trp Ala Val Ser Cys
 1               5                  10                  15

Gly Arg

<210> SEQ ID NO 70
<211> LENGTH: 18
<212> TYPE: PRT
<213> ORGANISM: Artificial Sequence
```

```
<220> FEATURE:
<223> OTHER INFORMATION: Synthetic polypeptide
<221> NAME/KEY: MOD_RES
<222> LOCATION: 10
<223> OTHER INFORMATION: Xaa = Homoarginine

<400> SEQUENCE: 70

Arg Gly Gly Arg Cys Leu Tyr Ser Arg Xaa Arg Tyr Ser Val Ile Cys
 1               5                  10                  15

Gly Arg

<210> SEQ ID NO 71
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 71

Arg Gly Ser Gly Cys Ile Tyr Cys Arg Arg Lys Trp Gly Val Val Gly
 1               5                  10                  15

Cys Arg

<210> SEQ ID NO 72
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 72

Arg Ala Thr Arg Cys Ile Phe Ser Arg Arg Arg Phe Ser Val Val Cys
 1               5                  10                  15

Gly Arg

<210> SEQ ID NO 73
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: MOD_RES
<222> LOCATION: 10
<223> OTHER INFORMATION: Xaa = Homoarginine

<400> SEQUENCE: 73

Arg Gly Gly Lys Cys Val Tyr Gly Arg Xaa Arg Phe Ser Val Val Cys
 1               5                  10                  15

Gly Arg

<210> SEQ ID NO 74
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: MOD_RES
<222> LOCATION: 9,18
<223> OTHER INFORMATION: Xaa = D-arginine

<400> SEQUENCE: 74

Arg Ala Thr Arg Cys Ile Phe Gly Xaa Arg Arg Phe Gly Val Val Cys
 1               5                  10                  15

Gly Xaa
```

```
<210> SEQ ID NO 75
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: MOD_RES
<222> LOCATION: 10
<223> OTHER INFORMATION: Xaa = D-homoarginine

<400> SEQUENCE: 75

Arg Gly Gly Lys Cys Val Tyr Leu Arg Xaa Arg Phe Leu Val Val Cys
 1               5                  10                  15

Gly Arg

<210> SEQ ID NO 76
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 76

Arg Gly Gly Arg Cys Val Phe Leu Arg Pro Arg Ile Gly Val Val Cys
 1               5                  10                  15

Gly Arg

<210> SEQ ID NO 77
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 77

Arg Gly Gly Cys Leu Arg Tyr Ala Val Pro Arg Phe Ala Val Arg Val
 1               5                  10                  15

Cys Arg

<210> SEQ ID NO 78
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 78

Arg Gly Gly Cys Leu Arg Tyr Thr Lys Pro Lys Phe Thr Val Arg Val
 1               5                  10                  15

Cys Arg

<210> SEQ ID NO 79
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 79

Arg Gly Gly Cys Leu Arg Tyr Ala Val Gly Arg Phe Ala Val Arg Val
 1               5                  10                  15

Cys Arg
```

```
<210> SEQ ID NO 80
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: MOD_RES
<222> LOCATION: 10
<223> OTHER INFORMATION: Xaa = MeGly

<400> SEQUENCE: 80

Arg Gly Gly Cys Leu Arg Tyr Ala Arg Xaa Arg Phe Ala Val Arg Val
 1               5                  10                  15

Cys Arg

<210> SEQ ID NO 81
<211> LENGTH: 19
<212> TYPE: PRT
<213> ORGANISM: Artificial Sequence
<220> FEATURE:
<223> OTHER INFORMATION: Synthetic polypeptide

<400> SEQUENCE: 81

Arg Gly Phe Cys Leu Arg Tyr Thr Val Pro Arg Phe Thr Val Arg Phe
 1               5                  10                  15

Cys Val Arg

<210> SEQ ID NO 82
<211> LENGTH: 19
<212> TYPE: PRT
<213> ORGANISM: Artificial Sequence
<220> FEATURE:
<223> OTHER INFORMATION: Synthetic polypeptide

<400> SEQUENCE: 82

Arg Gly Phe Cys Leu Arg Tyr Lys Val Gly Arg Phe Lys Val Arg Phe
 1               5                  10                  15

Cys Val Arg

<210> SEQ ID NO 83
<211> LENGTH: 19
<212> TYPE: PRT
<213> ORGANISM: Artificial Sequence
<220> FEATURE:
<223> OTHER INFORMATION: Synthetic polypeptide
<221> NAME/KEY: MOD_RES
<222> LOCATION: 8,13
<223> OTHER INFORMATION: Xaa = MeGly

<400> SEQUENCE: 83

Arg Gly Phe Cys Leu Arg Tyr Xaa Val Gly Arg Phe Xaa Val Arg Phe
 1               5                  10                  15

Cys Val Arg

<210> SEQ ID NO 84
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: MOD_RES
<222> LOCATION: 10
<223> OTHER INFORMATION: Xaa = MeGly

<400> SEQUENCE: 84

Arg Gly Gly Cys Leu Arg Tyr Ala Arg Xaa Arg Phe Ala Val Arg Val
```

```
                    1               5                  10                 15

Cys Arg

<210> SEQ ID NO 85
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 85

Arg Gly Gly Cys Leu Arg Tyr Ala Val Gly Arg Phe Ala Val Arg Val
  1               5                  10                 15

Cys Arg

<210> SEQ ID NO 86
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 86

Arg Gly Gly Arg Cys Leu Tyr Cys Arg Arg Phe Cys Val Val Gly
  1               5                  10                 15

Cys Arg

<210> SEQ ID NO 87
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 87

Arg Gly Gly Cys Arg Leu Tyr Cys Arg Arg Phe Cys Val Val Cys
  1               5                  10                 15

Gly Arg

<210> SEQ ID NO 88
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 88

Arg Gly Gly Arg Cys Leu Tyr Cys Arg Arg Phe Cys Val Cys Val
  1               5                  10                 15

Gly Arg

<210> SEQ ID NO 89
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 89

Arg Gly Gly Cys Arg Leu Tyr Cys Arg Arg Phe Cys Val Cys Val
  1               5                  10                 15

Gly Arg
```

```
<210> SEQ ID NO 90
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 90

Arg Gly Gly Arg Leu Cys Tyr Cys Arg Arg Arg Phe Cys Val Val Cys
 1               5                  10                  15

Gly Arg

<210> SEQ ID NO 91
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 91

Arg Gly Gly Arg Leu Cys Tyr Cys Arg Arg Arg Phe Cys Val Val Gly
 1               5                  10                  15

Cys Arg

<210> SEQ ID NO 92
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 92

Arg Gly Gly Cys Arg Leu Tyr Cys Arg Arg Arg Phe Cys Val Val Gly
 1               5                  10                  15

Cys

<210> SEQ ID NO 93
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 93

Arg Gly Gly Arg Cys Leu Tyr Cys Arg Arg Arg Phe Cys Val Val Gly
 1               5                  10                  15

Cys

<210> SEQ ID NO 94
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 94

Arg Gly Gly Cys Arg Leu Tyr Cys Arg Arg Arg Phe Cys Val Val Cys
 1               5                  10                  15

Gly

<210> SEQ ID NO 95
<211> LENGTH: 17
<212> TYPE: PRT
```

```
<213> ORGANISM: Artificial Sequence
<220> FEATURE:
<223> OTHER INFORMATION: Synthetic polypeptide

<400> SEQUENCE: 95

Arg Gly Gly Arg Cys Leu Tyr Cys Arg Arg Phe Cys Val Cys Val
 1               5                  10                  15

Gly

<210> SEQ ID NO 96
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 96

Arg Gly Gly Cys Arg Leu Tyr Cys Arg Arg Phe Cys Val Cys Val
 1               5                  10                  15

Gly

<210> SEQ ID NO 97
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 97

Arg Gly Gly Arg Leu Cys Tyr Cys Arg Arg Phe Cys Val Val Cys
 1               5                  10                  15

Gly

<210> SEQ ID NO 98
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 98

Arg Gly Gly Arg Leu Cys Tyr Cys Arg Arg Phe Cys Val Val Gly
 1               5                  10                  15

Cys

<210> SEQ ID NO 99
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 99

Arg Gly Gly Gly Cys Leu Tyr Cys Arg Arg Phe Cys Val Val Gly
 1               5                  10                  15

Cys Arg

<210> SEQ ID NO 100
<211> LENGTH: 18
<212> TYPE: PRT
<213> ORGANISM: Artificial Sequence
<220> FEATURE:
<223> OTHER INFORMATION: Synthetic polypeptide
```

```
<400> SEQUENCE: 100

Arg Gly Gly Gly Cys Leu Tyr Cys Arg Arg Phe Cys Val Cys Val
 1               5                  10                  15
Gly Arg

<210> SEQ ID NO 101
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 101

Arg Gly Gly Cys Gly Leu Tyr Cys Arg Arg Phe Cys Val Cys Val
 1               5                  10                  15
Gly Arg

<210> SEQ ID NO 102
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 102

Arg Gly Gly Gly Leu Cys Tyr Cys Arg Arg Phe Cys Val Val Cys
 1               5                  10                  15
Gly Arg

<210> SEQ ID NO 103
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 103

Arg Gly Gly Gly Leu Cys Tyr Cys Arg Arg Phe Cys Val Val Gly
 1               5                  10                  15
Cys Arg

<210> SEQ ID NO 104
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: DISULFID
<222> LOCATION: (5)...(16)
<221> NAME/KEY: DISULFID
<222> LOCATION: (8)...(13)

<400> SEQUENCE: 104

Arg Gly Gly Arg Cys Leu Tyr Cys Arg Arg Phe Cys Val Val Cys
 1               5                  10                  15
Gly Arg

<210> SEQ ID NO 105
<211> LENGTH: 17
<212> TYPE: PRT
<213> ORGANISM: Artificial Sequence
<220> FEATURE:
<223> OTHER INFORMATION: Synthetic polypeptide
<221> NAME/KEY: DISULFID
```

```
<222> LOCATION: (5)...(16)
<221> NAME/KEY: DISULFID
<222> LOCATION: (8)...(13)

<400> SEQUENCE: 105

Arg Gly Gly Arg Cys Leu Tyr Cys Arg Arg Arg Phe Cys Ile Val Cys
 1               5                  10                  15
Gly

<210> SEQ ID NO 106
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: DISULFID
<222> LOCATION: (5)...(16)
<221> NAME/KEY: DISULFID
<222> LOCATION: (8)...(13)

<400> SEQUENCE: 106

Arg Gly Gly Gly Cys Leu Tyr Cys Arg Arg Arg Phe Cys Val Val Cys
 1               5                  10                  15
Gly Arg

<210> SEQ ID NO 107
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: DISULFID
<222> LOCATION: (5)...(16)
<221> NAME/KEY: DISULFID
<222> LOCATION: (8)...(13)

<400> SEQUENCE: 107

Arg Gly Gly Arg Cys Leu Tyr Cys Arg Gly Trp Ile Cys Phe Val Cys
 1               5                  10                  15
Gly Arg

<210> SEQ ID NO 108
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: DISULFID
<222> LOCATION: (5)...(16)
<221> NAME/KEY: DISULFID
<222> LOCATION: (8)...(13)

<400> SEQUENCE: 108

Arg Gly Gly Arg Cys Leu Tyr Cys Arg Pro Arg Phe Cys Val Val Cys
 1               5                  10                  15
Gly Arg

<210> SEQ ID NO 109
<211> LENGTH: 17
<212> TYPE: PRT
<213> ORGANISM: Artificial Sequence
<220> FEATURE:
<223> OTHER INFORMATION: Synthetic polypeptide
<221> NAME/KEY: DISULFID
<222> LOCATION: (5)...(16)
<221> NAME/KEY: DISULFID
<222> LOCATION: (8)...(13)
```

<400> SEQUENCE: 109

Arg Gly Gly Arg Cys Val Tyr Cys Arg Arg Phe Cys Val Val Gly
 1               5                  10                  15

Cys

<210> SEQ ID NO 110
<211> LENGTH: 17
<212> TYPE: PRT
<213> ORGANISM: Artificial Sequence
<220> FEATURE:
<223> OTHER INFORMATION: Synthetic polypeptide
<221> NAME/KEY: DISULFID
<222> LOCATION: (5)...(16)
<221> NAME/KEY: DISULFID
<222> LOCATION: (8)...(13)

<400> SEQUENCE: 110

Lys Gly Gly Arg Cys Leu Tyr Cys Arg Arg Arg Phe Cys Val Val Cys
 1               5                  10                  15

Gly

<210> SEQ ID NO 111
<211> LENGTH: 16
<212> TYPE: PRT
<213> ORGANISM: Artificial Sequence
<220> FEATURE:
<223> OTHER INFORMATION: Synthetic polypeptide
<221> NAME/KEY: MOD_RES
<222> LOCATION: 4
<223> OTHER INFORMATION: Xaa = Homoarginine
<221> NAME/KEY: DISULFID
<222> LOCATION: (5)...(16)
<221> NAME/KEY: DISULFID
<222> LOCATION: (8)...(13)

<400> SEQUENCE: 111

Arg Gly Gly Xaa Cys Leu Tyr Cys Arg Arg Arg Phe Cys Val Val Cys
 1               5                  10                  15

<210> SEQ ID NO 112
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: MOD_RES
<222> LOCATION: 4,9
<223> OTHER INFORMATION: Xaa = Homoarginine
<221> NAME/KEY: DISULFID
<222> LOCATION: (5)...(16)
<221> NAME/KEY: DISULFID
<222> LOCATION: (8)...(13)

<400> SEQUENCE: 112

Arg Gly Gly Xaa Cys Leu Tyr Cys Xaa Arg Arg Phe Cys Val Val Cys
 1               5                  10                  15

Gly Arg

<210> SEQ ID NO 113
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: MOD_RES
<222> LOCATION: 10
<223> OTHER INFORMATION: Xaa = Homoarginine
<221> NAME/KEY: DISULFID
<222> LOCATION: (5)...(16)
<221> NAME/KEY: DISULFID
<222> LOCATION: (8)...(13)

<400> SEQUENCE: 113

Arg Gly Gly Arg Cys Val Tyr Cys Arg Xaa Arg Phe Cys Val Val Cys
1               5                   10                  15

Gly Arg

<210> SEQ ID NO 114
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: DISULFID
<222> LOCATION: (5)...(16)
<221> NAME/KEY: DISULFID
<222> LOCATION: (8)...(13)

<400> SEQUENCE: 114

Arg Gly Gly Arg Cys Leu Tyr Cys Arg Lys Lys Trp Cys Val Val Cys
1               5                   10                  15

Gly Arg

<210> SEQ ID NO 115
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: MOD_RES
<222> LOCATION: 10
<223> OTHER INFORMATION: Xaa = Homoarginine
<221> NAME/KEY: DISULFID
<222> LOCATION: (5)...(16)
<221> NAME/KEY: DISULFID
<222> LOCATION: (8)...(13)

<400> SEQUENCE: 115

Arg Gly Gly Arg Cys Leu Tyr Cys Arg Xaa Arg Tyr Cys Val Val Cys
1               5                   10                  15

Gly Arg

<210> SEQ ID NO 116
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: DISULFID
<222> LOCATION: (5)...(16)
<221> NAME/KEY: DISULFID
<222> LOCATION: (8)...(13)

<400> SEQUENCE: 116

Arg Gly Ser Gly Cys Leu Tyr Cys Arg Arg Lys Trp Cys Val Val Cys
1               5                   10                  15

Gly Arg

<210> SEQ ID NO 117
<211> LENGTH: 18
<212> TYPE: PRT
<213> ORGANISM: Artificial Sequence
<220> FEATURE:
<223> OTHER INFORMATION: Synthetic polypeptide

```
<221> NAME/KEY: DISULFID
<222> LOCATION: (5)...(16)
<221> NAME/KEY: DISULFID
<222> LOCATION: (8)...(13)

<400> SEQUENCE: 117

Arg Ala Thr Arg Cys Ile Phe Cys Arg Arg Arg Phe Cys Val Val Cys
 1               5                  10                  15

Gly Arg

<210> SEQ ID NO 118
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: MOD_RES
<222> LOCATION: 10
<223> OTHER INFORMATION: Xaa = Homoarginine
<221> NAME/KEY: DISULFID
<222> LOCATION: (5)...(16)
<221> NAME/KEY: DISULFID
<222> LOCATION: (8)...(13)

<400> SEQUENCE: 118

Arg Gly Gly Lys Cys Val Tyr Cys Arg Xaa Arg Phe Cys Val Val Cys
 1               5                  10                  15

Gly Arg

<210> SEQ ID NO 119
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: MOD_RES
<222> LOCATION: 9,18
<223> OTHER INFORMATION: Xaa = D-arginine
<221> NAME/KEY: DISULFID
<222> LOCATION: (5)...(16)
<221> NAME/KEY: DISULFID
<222> LOCATION: (8)...(13)

<400> SEQUENCE: 119

Arg Ala Thr Arg Cys Ile Phe Cys Xaa Arg Arg Phe Cys Val Val Cys
 1               5                  10                  15

Gly Xaa

<210> SEQ ID NO 120
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: MOD_RES
<222> LOCATION: 10
<223> OTHER INFORMATION: Xaa = D-homoarginine
<221> NAME/KEY: DISULFID
<222> LOCATION: (5)...(16)
<221> NAME/KEY: DISULFID
<222> LOCATION: (8)...(13)

<400> SEQUENCE: 120

Arg Gly Gly Lys Cys Val Tyr Cys Arg Xaa Arg Phe Cys Val Val Cys
 1               5                  10                  15

Gly Arg
```

```
<210> SEQ ID NO 121
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: MOD_RES
<222> LOCATION: (1)...(18)
<223> OTHER INFORMATION: All genetically encoded amino acids are in the
      D-configuration
<221> NAME/KEY: DISULFID
<222> LOCATION: (5)...(16)
<221> NAME/KEY: DISULFID
<222> LOCATION: (8)...(13)

<400> SEQUENCE: 121

Arg Gly Gly Arg Cys Leu Tyr Cys Arg Arg Arg Phe Cys Val Val Cys
 1               5                  10                  15

Gly Arg

<210> SEQ ID NO 122
<211> LENGTH: 17
<212> TYPE: PRT
<213> ORGANISM: Artificial Sequence
<220> FEATURE:
<223> OTHER INFORMATION: Synthetic polypeptide
<221> NAME/KEY: MOD_RES
<222> LOCATION: (1)...(16)
<223> OTHER INFORMATION: All genetically encoded amino acids are in the
      D-configuration
<221> NAME/KEY: DISULFID
<222> LOCATION: (5)...(16)
<221> NAME/KEY: DISULFID
<222> LOCATION: (8)...(13)

<400> SEQUENCE: 122

Arg Gly Gly Arg Cys Leu Tyr Cys Arg Arg Arg Phe Cys Ile Val Cys
 1               5                  10                  15

Gly

<210> SEQ ID NO 123
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: MOD_RES
<222> LOCATION: (1)...(18)
<223> OTHER INFORMATION: All genetically encoded amino acids are in the
      D-configuration
<221> NAME/KEY: DISULFID
<222> LOCATION: (5)...(16)
<221> NAME/KEY: DISULFID
<222> LOCATION: (8)...(13)

<400> SEQUENCE: 123

Arg Gly Gly Gly Cys Leu Tyr Cys Arg Arg Arg Phe Cys Val Val Cys
 1               5                  10                  15

Gly Arg

<210> SEQ ID NO 124
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: MOD_RES
<222> LOCATION: (1)...(18)
<223> OTHER INFORMATION: All genetically encoded amino acids are in the
      D-configuration
```

```
<221> NAME/KEY: DISULFID
<222> LOCATION: (5)...(16)
<221> NAME/KEY: DISULFID
<222> LOCATION: (8)...(13)

<400> SEQUENCE: 124

Arg Gly Gly Arg Cys Leu Tyr Cys Arg Gly Trp Ile Cys Phe Val Cys
 1               5                  10                  15
Gly Arg

<210> SEQ ID NO 125
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: DISULFID
<222> LOCATION: (5)...(8)
<221> NAME/KEY: DISULFID
<222> LOCATION: (13)...(16)

<400> SEQUENCE: 125

Arg Gly Gly Arg Cys Leu Tyr Cys Arg Arg Arg Phe Cys Val Val Cys
 1               5                  10                  15
Gly Arg

<210> SEQ ID NO 126
<211> LENGTH: 17
<212> TYPE: PRT
<213> ORGANISM: Artificial Sequence
<220> FEATURE:
<223> OTHER INFORMATION: Synthetic polypeptide
<221> NAME/KEY: DISULFID
<222> LOCATION: (5)...(8)
<221> NAME/KEY: DISULFID
<222> LOCATION: (13)...(16)

<400> SEQUENCE: 126

Arg Gly Gly Arg Cys Leu Tyr Cys Arg Arg Arg Phe Cys Ile Val Cys
 1               5                  10                  15
Gly

<210> SEQ ID NO 127
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: DISULFID
<222> LOCATION: (5)...(8)
<221> NAME/KEY: DISULFID
<222> LOCATION: (13)...(16)

<400> SEQUENCE: 127

Arg Gly Gly Gly Cys Leu Tyr Cys Arg Arg Arg Phe Cys Val Val Cys
 1               5                  10                  15
Gly Arg

<210> SEQ ID NO 128
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: DISULFID
<222> LOCATION: (5)...(8)
<221> NAME/KEY: DISULFID
<222> LOCATION: (13)...(16)
```

<400> SEQUENCE: 128

Arg Gly Gly Arg Cys Leu Tyr Cys Arg Gly Trp Ile Cys Phe Val Cys
 1               5                  10                  15
Gly Arg

<210> SEQ ID NO 129
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: DISULFID
<222> LOCATION: (5)...(8)
<221> NAME/KEY: DISULFID
<222> LOCATION: (13)...(16)

<400> SEQUENCE: 129

Arg Gly Gly Arg Cys Leu Tyr Cys Arg Pro Arg Phe Cys Val Val Cys
 1               5                  10                  15
Gly Arg

<210> SEQ ID NO 130
<211> LENGTH: 17
<212> TYPE: PRT
<213> ORGANISM: Artificial Sequence
<220> FEATURE:
<223> OTHER INFORMATION: Synthetic polypeptide
<221> NAME/KEY: DISULFID
<222> LOCATION: (5)...(8)
<221> NAME/KEY: DISULFID
<222> LOCATION: (13)...(16)

<400> SEQUENCE: 130

Arg Gly Gly Arg Cys Val Tyr Cys Arg Arg Arg Phe Cys Val Val Cys
 1               5                  10                  15
Gly

<210> SEQ ID NO 131
<211> LENGTH: 17
<212> TYPE: PRT
<213> ORGANISM: Artificial Sequence
<220> FEATURE:
<223> OTHER INFORMATION: Synthetic polypeptide
<221> NAME/KEY: DISULFID
<222> LOCATION: (5)...(8)
<221> NAME/KEY: DISULFID
<222> LOCATION: (13)...(16)

<400> SEQUENCE: 131

Lys Gly Gly Arg Cys Leu Tyr Cys Arg Arg Arg Phe Cys Val Val Cys
 1               5                  10                  15
Gly

<210> SEQ ID NO 132
<211> LENGTH: 16
<212> TYPE: PRT
<213> ORGANISM: Artificial Sequence
<220> FEATURE:
<223> OTHER INFORMATION: Synthetic polypeptide
<221> NAME/KEY: MOD_RES
<222> LOCATION: 4
<223> OTHER INFORMATION: Xaa = Homoarginine
<221> NAME/KEY: DISULFID
<222> LOCATION: (5)...(8)
<221> NAME/KEY: DISULFID
<222> LOCATION: (13)...(16)

-continued

```
<400> SEQUENCE: 132

Arg Gly Gly Xaa Cys Leu Tyr Cys Arg Arg Arg Phe Cys Val Val Cys
 1               5                  10                  15

<210> SEQ ID NO 133
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: MOD_RES
<222> LOCATION: 4,9
<223> OTHER INFORMATION: Xaa = Homoarginine
<221> NAME/KEY: DISULFID
<222> LOCATION: (5)...(8)
<221> NAME/KEY: DISULFID
<222> LOCATION: (13)...(16)

<400> SEQUENCE: 133

Arg Gly Gly Xaa Cys Leu Tyr Cys Xaa Arg Arg Phe Cys Val Val Cys
 1               5                  10                  15

Gly Arg

<210> SEQ ID NO 134
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: MOD_RES
<222> LOCATION: 10
<223> OTHER INFORMATION: Xaa = Homoarginine
<221> NAME/KEY: DISULFID
<222> LOCATION: (5)...(8)
<221> NAME/KEY: DISULFID
<222> LOCATION: (13)...(16)

<400> SEQUENCE: 134

Arg Gly Gly Arg Cys Val Tyr Cys Arg Xaa Arg Phe Cys Val Val Cys
 1               5                  10                  15

Gly Arg

<210> SEQ ID NO 135
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: DISULFID
<222> LOCATION: (5)...(8)
<221> NAME/KEY: DISULFID
<222> LOCATION: (13)...(16)

<400> SEQUENCE: 135

Arg Gly Gly Arg Cys Leu Tyr Cys Arg Lys Lys Trp Cys Val Val Cys
 1               5                  10                  15

Gly Arg

<210> SEQ ID NO 136
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: MOD_RES
<222> LOCATION: 10
<223> OTHER INFORMATION: Xaa = Homoarginine
```

```
<221> NAME/KEY: DISULFID
<222> LOCATION: (5)...(8)
<221> NAME/KEY: DISULFID
<222> LOCATION: (13)...(16)

<400> SEQUENCE: 136

Arg Gly Gly Arg Cys Leu Tyr Cys Arg Xaa Arg Tyr Cys Val Val Cys
 1               5                  10                  15
Gly Arg

<210> SEQ ID NO 137
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: DISULFID
<222> LOCATION: (5)...(8)
<221> NAME/KEY: DISULFID
<222> LOCATION: (13)...(16)

<400> SEQUENCE: 137

Arg Gly Ser Gly Cys Leu Tyr Cys Arg Arg Lys Trp Cys Val Val Cys
 1               5                  10                  15
Gly Arg

<210> SEQ ID NO 138
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: DISULFID
<222> LOCATION: (5)...(8)
<221> NAME/KEY: DISULFID
<222> LOCATION: (13)...(16)

<400> SEQUENCE: 138

Arg Ala Thr Arg Cys Ile Phe Cys Arg Arg Arg Phe Cys Val Val Cys
 1               5                  10                  15
Gly Arg

<210> SEQ ID NO 139
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: MOD_RES
<222> LOCATION: 10
<223> OTHER INFORMATION: Xaa = Homoarginine
<221> NAME/KEY: DISULFID
<222> LOCATION: (5)...(8)
<221> NAME/KEY: DISULFID
<222> LOCATION: (13)...(16)

<400> SEQUENCE: 139

Arg Gly Gly Lys Cys Val Tyr Cys Arg Xaa Arg Phe Cys Val Val Cys
 1               5                  10                  15
Gly Arg

<210> SEQ ID NO 140
<211> LENGTH: 18
<212> TYPE: PRT
<213> ORGANISM: Artificial Sequence
<220> FEATURE:
<223> OTHER INFORMATION: Synthetic polypeptide
```

```
<221> NAME/KEY: MOD_RES
<222> LOCATION: 9,18
<223> OTHER INFORMATION: Xaa = D-arginine
<221> NAME/KEY: DISULFID
<222> LOCATION: (5)...(8)
<221> NAME/KEY: DISULFID
<222> LOCATION: (13)...(16)

<400> SEQUENCE: 140

Arg Ala Thr Arg Cys Ile Phe Cys Xaa Arg Arg Phe Cys Val Val Cys
 1               5                  10                  15

Gly Xaa

<210> SEQ ID NO 141
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: MOD_RES
<222> LOCATION: 10
<223> OTHER INFORMATION: Xaa = D-homoarginine
<221> NAME/KEY: DISULFID
<222> LOCATION: (5)...(8)
<221> NAME/KEY: DISULFID
<222> LOCATION: (13)...(16)

<400> SEQUENCE: 141

Arg Gly Gly Lys Cys Val Tyr Cys Arg Xaa Arg Phe Cys Val Val Cys
 1               5                  10                  15

Gly Arg

<210> SEQ ID NO 142
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: MOD_RES
<222> LOCATION: (1)...(18)
<223> OTHER INFORMATION: All genetically encoded amino acids are in the
      D-configuration
<221> NAME/KEY: DISULFID
<222> LOCATION: (5)...(8)
<221> NAME/KEY: DISULFID
<222> LOCATION: (13)...(16)

<400> SEQUENCE: 142

Arg Gly Gly Arg Cys Leu Tyr Cys Arg Arg Arg Phe Cys Val Val Cys
 1               5                  10                  15

Gly Arg

<210> SEQ ID NO 143
<211> LENGTH: 17
<212> TYPE: PRT
<213> ORGANISM: Artificial Sequence
<220> FEATURE:
<223> OTHER INFORMATION: Synthetic polypeptide
<221> NAME/KEY: MOD_RES
<222> LOCATION: (1)...(17)
<223> OTHER INFORMATION: All genetically encoded amino acids are in the
      D-configuration
<221> NAME/KEY: DISULFID
<222> LOCATION: (5)...(8)
<221> NAME/KEY: DISULFID
<222> LOCATION: (13)...(16)

<400> SEQUENCE: 143

Arg Gly Gly Arg Cys Leu Tyr Cys Arg Arg Arg Phe Cys Ile Val Cys
```

```
1               5                  10                 15
Gly

<210> SEQ ID NO 144
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: MOD_RES
<222> LOCATION: (1)...(18)
<223> OTHER INFORMATION: All genetically encoded amino acids are in the
      D-configuration
<221> NAME/KEY: DISULFID
<222> LOCATION: (5)...(8)
<221> NAME/KEY: DISULFID
<222> LOCATION: (13)...(16)

<400> SEQUENCE: 144

Arg Gly Gly Gly Cys Leu Tyr Cys Arg Arg Arg Phe Cys Val Val Cys
1               5                  10                 15

Gly Arg

<210> SEQ ID NO 145
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: DISULFID
<222> LOCATION: (5)...(8)
<221> NAME/KEY: DISULFID
<222> LOCATION: (13)...(16)
<221> NAME/KEY: MOD_RES
<222> LOCATION: (1)...(18)
<223> OTHER INFORMATION: All genetically encoded amino acids are in the
      D-configuration

<400> SEQUENCE: 145

Arg Gly Gly Arg Cys Leu Tyr Cys Arg Gly Trp Ile Cys Phe Val Cys
1               5                  10                 15

Gly Arg

<210> SEQ ID NO 146
<211> LENGTH: 17
<212> TYPE: PRT
<213> ORGANISM: Artificial Sequence
<220> FEATURE:
<223> OTHER INFORMATION: Synthetic polypeptide
<221> NAME/KEY: DISULFID
<222> LOCATION: (4)...(17)
<221> NAME/KEY: DISULFID
<222> LOCATION: (8)...(13)

<400> SEQUENCE: 146

Arg Gly Gly Cys Arg Val Tyr Cys Arg Arg Arg Phe Cys Val Ile Gly
1               5                  10                 15

Cys

<210> SEQ ID NO 147
<211> LENGTH: 17
<212> TYPE: PRT
<213> ORGANISM: Artificial Sequence
<220> FEATURE:
<223> OTHER INFORMATION: Synthetic polypeptide
<221> NAME/KEY: DISULFID
<222> LOCATION: (4)...(17)
<221> NAME/KEY: DISULFID
```

<222> LOCATION: (8)...(13)

<400> SEQUENCE: 147

Lys Gly Gly Cys Arg Ile Tyr Cys Arg Arg Phe Cys Val Ile Gly
 1               5                  10                  15

Cys

<210> SEQ ID NO 148
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: MOD_RES
<222> LOCATION: 5,9
<223> OTHER INFORMATION: Xaa = Homoarginine
<221> NAME/KEY: DISULFID
<222> LOCATION: (4)...(17)
<221> NAME/KEY: DISULFID
<222> LOCATION: (8)...(13)

<400> SEQUENCE: 148

Arg Gly Gly Cys Xaa Leu Tyr Cys Xaa Arg Arg Phe Cys Val Ile Gly
 1               5                  10                  15

Cys Arg

<210> SEQ ID NO 149
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: MOD_RES
<222> LOCATION: 10
<223> OTHER INFORMATION: Xaa = Homoarginine
<221> NAME/KEY: DISULFID
<222> LOCATION: (4)...(17)
<221> NAME/KEY: DISULFID
<222> LOCATION: (8)...(13)

<400> SEQUENCE: 149

Arg Gly Gly Cys Arg Val Tyr Cys Arg Xaa Arg Phe Cys Val Val Gly
 1               5                  10                  15

Cys Arg

<210> SEQ ID NO 150
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: DISULFID
<222> LOCATION: (4)...(17)
<221> NAME/KEY: DISULFID
<222> LOCATION: (8)...(13)

<400> SEQUENCE: 150

Arg Gly Gly Cys Arg Leu Tyr Cys Arg Lys Lys Trp Cys Val Val Gly
 1               5                  10                  15

Cys Arg

<210> SEQ ID NO 151
<211> LENGTH: 18
<212> TYPE: PRT
<213> ORGANISM: Artificial Sequence
<220> FEATURE:
<223> OTHER INFORMATION: Synthetic polypeptide

```
<221> NAME/KEY: MOD_RES
<222> LOCATION: 10
<223> OTHER INFORMATION: Xaa = Homoarginine
<221> NAME/KEY: DISULFID
<222> LOCATION: (4)...(17)
<221> NAME/KEY: DISULFID
<222> LOCATION: (8)...(13)

<400> SEQUENCE: 151

Arg Gly Gly Cys Arg Leu Tyr Cys Arg Xaa Arg Tyr Cys Val Val Ala
 1               5                  10                  15

Cys Arg

<210> SEQ ID NO 152
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: DISULFID
<222> LOCATION: (4)...(17)
<221> NAME/KEY: DISULFID
<222> LOCATION: (8)...(13)

<400> SEQUENCE: 152

Arg Gly Ser Cys Gly Leu Tyr Cys Arg Arg Lys Trp Cys Val Val Gly
 1               5                  10                  15

Cys Arg

<210> SEQ ID NO 153
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: DISULFID
<222> LOCATION: (4)...(17)
<221> NAME/KEY: DISULFID
<222> LOCATION: (8)...(13)

<400> SEQUENCE: 153

Arg Ala Thr Cys Arg Ile Phe Cys Arg Arg Arg Phe Cys Val Ile Gly
 1               5                  10                  15

Cys Arg

<210> SEQ ID NO 154
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: MOD_RES
<222> LOCATION: 10
<223> OTHER INFORMATION: Xaa = Homoarginine
<221> NAME/KEY: DISULFID
<222> LOCATION: (4)...(17)
<221> NAME/KEY: DISULFID
<222> LOCATION: (8)...(13)

<400> SEQUENCE: 154

Arg Gly Gly Cys Lys Val Tyr Cys Arg Xaa Arg Phe Cys Val Ile Gly
 1               5                  10                  15

Cys Arg

<210> SEQ ID NO 155
<211> LENGTH: 18
<212> TYPE: PRT
```

```
<213> ORGANISM: Artificial Sequence
<220> FEATURE:
<223> OTHER INFORMATION: Synthetic polypeptide
<221> NAME/KEY: MOD_RES
<222> LOCATION: 9,18
<223> OTHER INFORMATION: Xaa = D-arginine
<221> NAME/KEY: DISULFID
<222> LOCATION: (4)...(17)
<221> NAME/KEY: DISULFID
<222> LOCATION: (8)...(13)

<400> SEQUENCE: 155

Arg Ala Thr Cys Arg Ile Phe Cys Xaa Arg Arg Phe Cys Val Val Gly
  1               5                  10                  15

Cys Xaa

<210> SEQ ID NO 156
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: MOD_RES
<222> LOCATION: 10
<223> OTHER INFORMATION: Xaa = D-homoarginine
<221> NAME/KEY: DISULFID
<222> LOCATION: (4)...(17)
<221> NAME/KEY: DISULFID
<222> LOCATION: (8)...(13)

<400> SEQUENCE: 156

Arg Gly Gly Cys Lys Val Tyr Cys Arg Xaa Arg Phe Cys Val Val Gly
  1               5                  10                  15

Cys Arg

<210> SEQ ID NO 157
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: MOD_RES
<222> LOCATION: (1)...(18)
<223> OTHER INFORMATION: All genetically encoded amino acids are in the
      D-configuration
<221> NAME/KEY: DISULFID
<222> LOCATION: (4)...(17)
<221> NAME/KEY: DISULFID
<222> LOCATION: (8)...(13)

<400> SEQUENCE: 157

Arg Gly Gly Cys Arg Leu Tyr Cys Arg Arg Arg Phe Cys Val Val Gly
  1               5                  10                  15

Cys Arg

<210> SEQ ID NO 158
<211> LENGTH: 17
<212> TYPE: PRT
<213> ORGANISM: Artificial Sequence
<220> FEATURE:
<223> OTHER INFORMATION: Synthetic polypeptide
<221> NAME/KEY: MOD_RES
<222> LOCATION: (1)...(17)
<223> OTHER INFORMATION: All genetically encoded amino acids are in the
      D-configuration
<221> NAME/KEY: DISULFID
<222> LOCATION: (4)...(17)
<221> NAME/KEY: DISULFID
<222> LOCATION: (8)...(13)
```

```
<400> SEQUENCE: 158

Arg Gly Gly Cys Arg Leu Tyr Cys Arg Arg Arg Phe Cys Ile Val Gly
 1               5                  10                  15

Cys

<210> SEQ ID NO 159
<211> LENGTH: 17
<212> TYPE: PRT
<213> ORGANISM: Artificial Sequence
<220> FEATURE:
<223> OTHER INFORMATION: Synthetic polypeptide
<221> NAME/KEY: MOD_RES
<222> LOCATION: (1)...(17)
<223> OTHER INFORMATION: All genetically encoded amino acids are in the
      D-configuration
<221> NAME/KEY: DISULFID
<222> LOCATION: (4)...(17)
<221> NAME/KEY: DISULFID
<222> LOCATION: (8)...(13)

<400> SEQUENCE: 159

Arg Gly Gly Cys Arg Leu Tyr Cys Arg Arg Phe Cys Ile Val Gly
 1               5                  10                  15

Cys

<210> SEQ ID NO 160
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: MOD_RES
<222> LOCATION: (1)...(18)
<223> OTHER INFORMATION: All genetically encoded amino acids are in the
      D-configuration
<221> NAME/KEY: DISULFID
<222> LOCATION: (4)...(17)
<221> NAME/KEY: DISULFID
<222> LOCATION: (8)...(13)

<400> SEQUENCE: 160

Arg Gly Gly Cys Arg Leu Tyr Cys Arg Gly Trp Ile Cys Phe Val Gly
 1               5                  10                  15

Cys Arg

<210> SEQ ID NO 161
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: DISULFID
<222> LOCATION: (4)...(17)
<221> NAME/KEY: DISULFID
<222> LOCATION: (8)...(13)

<400> SEQUENCE: 161

Arg Gly Gly Cys Leu Arg Tyr Cys Arg Pro Arg Phe Cys Val Arg Val
 1               5                  10                  15

Cys Arg

<210> SEQ ID NO 162
<211> LENGTH: 18
<212> TYPE: PRT
<213> ORGANISM: Artificial Sequence
<220> FEATURE:
<223> OTHER INFORMATION: Synthetic polypeptide
```

```
<221> NAME/KEY: DISULFID
<222> LOCATION: (4)...(17)
<221> NAME/KEY: DISULFID
<222> LOCATION: (8)...(13)

<400> SEQUENCE: 162

Arg Gly Val Cys Leu Arg Tyr Cys Arg Gly Arg Phe Cys Val Arg Leu
 1               5                  10                  15

Cys Arg

<210> SEQ ID NO 163
<211> LENGTH: 20
<212> TYPE: PRT
<213> ORGANISM: Artificial Sequence
<220> FEATURE:
<223> OTHER INFORMATION: Synthetic polypeptide
<221> NAME/KEY: DISULFID
<222> LOCATION: (5)...(18)
<221> NAME/KEY: DISULFID
<222> LOCATION: (9)...(14)

<400> SEQUENCE: 163

Arg Gly Arg Val Cys Leu Arg Tyr Cys Arg Gly Arg Phe Cys Val Arg
 1               5                  10                  15

Leu Cys Phe Arg
             20

<210> SEQ ID NO 164
<211> LENGTH: 20
<212> TYPE: PRT
<213> ORGANISM: Artificial Sequence
<220> FEATURE:
<223> OTHER INFORMATION: Synthetic polypeptide
<221> NAME/KEY: DISULFID
<222> LOCATION: (5)...(18)
<221> NAME/KEY: DISULFID
<222> LOCATION: (9)...(14)

<400> SEQUENCE: 164

Arg Trp Arg Val Cys Leu Arg Tyr Cys Arg Gly Arg Phe Cys Val Arg
 1               5                  10                  15

Leu Cys Leu Arg
             20

<210> SEQ ID NO 165
<211> LENGTH: 21
<212> TYPE: PRT
<213> ORGANISM: Artificial Sequence
<220> FEATURE:
<223> OTHER INFORMATION: Synthetic polypeptide
<221> NAME/KEY: DISULFID
<222> LOCATION: (6)...(19)
<221> NAME/KEY: DISULFID
<222> LOCATION: (10)...(15)

<400> SEQUENCE: 165

Arg Gly Trp Arg Val Cys Leu Lys Tyr Cys Arg Gly Arg Phe Cys Val
 1               5                  10                  15

Lys Leu Cys Leu Arg
             20

<210> SEQ ID NO 166
<211> LENGTH: 21
<212> TYPE: PRT
<213> ORGANISM: Artificial Sequence
<220> FEATURE:
<223> OTHER INFORMATION: Synthetic polypeptide
```

```
<221> NAME/KEY: DISULFID
<222> LOCATION: (6)...(19)
<221> NAME/KEY: DISULFID
<222> LOCATION: (10)...(15)

<400> SEQUENCE: 166

Arg Gly Gly Arg Val Cys Leu Arg Tyr Cys Arg Gly Lys Phe Cys Val
 1               5                  10                  15

Arg Leu Cys Leu Arg
            20

<210> SEQ ID NO 167
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: DISULFID
<222> LOCATION: (4)...(17)
<221> NAME/KEY: DISULFID
<222> LOCATION: (8)...(13)

<400> SEQUENCE: 167

Arg Gly Gly Cys Leu Arg Tyr Cys Arg Pro Arg Phe Cys Arg Val Cys
 1               5                  10                  15

Cys Arg

<210> SEQ ID NO 168
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: DISULFID
<222> LOCATION: (4)...(17)
<221> NAME/KEY: DISULFID
<222> LOCATION: (8)...(13)

<400> SEQUENCE: 168

Arg Gly Gly Cys Arg Leu Tyr Cys Arg Arg Arg Phe Cys Val Val Gly
 1               5                  10                  15

Cys Arg

<210> SEQ ID NO 169
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: DISULFID
<222> LOCATION: (4)...(17)
<221> NAME/KEY: DISULFID
<222> LOCATION: (8)...(13)

<400> SEQUENCE: 169

Arg Gly Val Cys Leu Arg Tyr Cys Arg Gly Arg Phe Cys Val Arg Leu
 1               5                  10                  15

Cys Arg

<210> SEQ ID NO 170
<211> LENGTH: 20
<212> TYPE: PRT
<213> ORGANISM: Artificial Sequence
<220> FEATURE:
<223> OTHER INFORMATION: Synthetic polypeptide
<221> NAME/KEY: DISULFID
<222> LOCATION: (5)...(18)
```

```
<221> NAME/KEY: DISULFID
<222> LOCATION: (9)...(14)

<400> SEQUENCE: 170

Arg Gly Arg Val Cys Leu Arg Tyr Cys Arg Gly Arg Phe Cys Val Arg
 1               5                  10                  15

Leu Cys Phe Arg
            20

<210> SEQ ID NO 171
<211> LENGTH: 20
<212> TYPE: PRT
<213> ORGANISM: Artificial Sequence
<220> FEATURE:
<223> OTHER INFORMATION: Synthetic polypeptide
<221> NAME/KEY: DISULFID
<222> LOCATION: (5)...(18)
<221> NAME/KEY: DISULFID
<222> LOCATION: (9)...(14)

<400> SEQUENCE: 171

Arg Trp Arg Val Cys Leu Arg Tyr Cys Arg Gly Arg Phe Cys Val Arg
 1               5                  10                  15

Leu Cys Leu Arg
            20

<210> SEQ ID NO 172
<211> LENGTH: 21
<212> TYPE: PRT
<213> ORGANISM: Artificial Sequence
<220> FEATURE:
<223> OTHER INFORMATION: Synthetic polypeptide
<221> NAME/KEY: DISULFID
<222> LOCATION: (6)...(19)
<221> NAME/KEY: DISULFID
<222> LOCATION: (10)...(15)

<400> SEQUENCE: 172

Arg Gly Trp Arg Val Cys Leu Lys Tyr Cys Arg Gly Arg Phe Cys Val
 1               5                  10                  15

Lys Leu Cys Leu Arg
            20

<210> SEQ ID NO 173
<211> LENGTH: 21
<212> TYPE: PRT
<213> ORGANISM: Artificial Sequence
<220> FEATURE:
<223> OTHER INFORMATION: Synthetic polypeptide
<221> NAME/KEY: DISULFID
<222> LOCATION: (6)...(19)
<221> NAME/KEY: DISULFID
<222> LOCATION: (10)...(15)

<400> SEQUENCE: 173

Arg Gly Gly Arg Val Cys Leu Arg Tyr Cys Arg Gly Arg Phe Cys Val
 1               5                  10                  15

Arg Leu Cys Leu Arg
            20

<210> SEQ ID NO 174
<211> LENGTH: 17
<212> TYPE: PRT
<213> ORGANISM: Artificial Sequence
<220> FEATURE:
<223> OTHER INFORMATION: Synthetic polypeptide
<221> NAME/KEY: DISULFID
```

```
<222> LOCATION: (4)...(17)
<221> NAME/KEY: DISULFID
<222> LOCATION: (8)...(13)

<400> SEQUENCE: 174

Arg Gly Gly Cys Arg Leu Tyr Cys Arg Arg Arg Phe Cys Val Val Gly
 1               5                  10                  15
Cys

<210> SEQ ID NO 175
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: DISULFID
<222> LOCATION: (4)...(17)

<400> SEQUENCE: 175

Arg Gly Gly Cys Leu Arg Tyr Ala Val Pro Arg Phe Ala Val Arg Val
 1               5                  10                  15
Cys Arg

<210> SEQ ID NO 176
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: DISULFID
<222> LOCATION: (4)...(7)

<400> SEQUENCE: 176

Arg Gly Gly Cys Leu Arg Tyr Thr Lys Pro Lys Phe Thr Val Arg Val
 1               5                  10                  15
Cys Arg

<210> SEQ ID NO 177
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: DISULFID
<222> LOCATION: (4)...(17)

<400> SEQUENCE: 177

Arg Gly Gly Cys Leu Arg Tyr Ala Val Gly Arg Phe Ala Val Arg Val
 1               5                  10                  15
Cys Arg

<210> SEQ ID NO 178
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: MOD_RES
<222> LOCATION: 5,9
<223> OTHER INFORMATION: Xaa = Homoarginine
<221> NAME/KEY: DISULFID
<222> LOCATION: (4)...(17)

<400> SEQUENCE: 178

Arg Gly Gly Cys Xaa Leu Tyr Ala Xaa Arg Arg Phe Ser Val Val Gly
 1               5                  10                  15
```

Cys Arg

```
<210> SEQ ID NO 179
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: MOD_RES
<222> LOCATION: 10
<223> OTHER INFORMATION: Xaa = MeGly
<221> NAME/KEY: DISULFID
<222> LOCATION: (4)...(17)

<400> SEQUENCE: 179
```

Arg Gly Gly Cys Leu Arg Tyr Ala Arg Xaa Arg Phe Ala Val Arg Val
 1               5                  10                  15

Cys Arg

```
<210> SEQ ID NO 180
<211> LENGTH: 19
<212> TYPE: PRT
<213> ORGANISM: Artificial Sequence
<220> FEATURE:
<223> OTHER INFORMATION: Synthetic polypeptide
<221> NAME/KEY: DISULFID
<222> LOCATION: (4)...(17)

<400> SEQUENCE: 180
```

Arg Gly Phe Cys Leu Arg Tyr Thr Val Pro Arg Phe Thr Val Arg Phe
 1               5                  10                  15

Cys Val Arg

```
<210> SEQ ID NO 181
<211> LENGTH: 19
<212> TYPE: PRT
<213> ORGANISM: Artificial Sequence
<220> FEATURE:
<223> OTHER INFORMATION: Synthetic polypeptide
<221> NAME/KEY: DISULFID
<222> LOCATION: (4)...(17)

<400> SEQUENCE: 181
```

Arg Gly Phe Cys Leu Arg Tyr Lys Val Gly Arg Phe Lys Val Arg Phe
 1               5                  10                  15

Cys Val Arg

```
<210> SEQ ID NO 182
<211> LENGTH: 19
<212> TYPE: PRT
<213> ORGANISM: Artificial Sequence
<220> FEATURE:
<223> OTHER INFORMATION: Synthetic polypeptide
<221> NAME/KEY: MOD_RES
<222> LOCATION: 8,13
<223> OTHER INFORMATION: Xaa = MeGly
<221> NAME/KEY: DISULFID
<222> LOCATION: (4)...(17)

<400> SEQUENCE: 182
```

Arg Gly Phe Cys Leu Arg Tyr Xaa Val Gly Arg Phe Xaa Val Arg Phe
 1               5                  10                  15

Cys Val Arg

```
<210> SEQ ID NO 183
```

```
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: MOD_RES
<222> LOCATION: 10
<223> OTHER INFORMATION: Xaa = MeGly
<221> NAME/KEY: DISULFID
<222> LOCATION: (4)...(17)

<400> SEQUENCE: 183

Arg Gly Gly Cys Leu Arg Tyr Ala Arg Xaa Arg Phe Ala Val Arg Val
 1               5                  10                  15

Cys Arg

<210> SEQ ID NO 184
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: DISULFID
<222> LOCATION: (4)...(17)

<400> SEQUENCE: 184

Arg Gly Gly Cys Leu Arg Tyr Ala Val Gly Arg Phe Ala Val Arg Val
 1               5                  10                  15

Cys Arg

<210> SEQ ID NO 185
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: DISULFID
<222> LOCATION: (5)...(16)

<400> SEQUENCE: 185

Arg Gly Gly Arg Cys Leu Tyr Ala Arg Arg Arg Phe Ala Val Val Cys
 1               5                  10                  15

Gly Arg

<210> SEQ ID NO 186
<211> LENGTH: 16
<212> TYPE: PRT
<213> ORGANISM: Artificial Sequence
<220> FEATURE:
<223> OTHER INFORMATION: Synthetic polypeptide
<221> NAME/KEY: DISULFID
<222> LOCATION: (5)...(16)

<400> SEQUENCE: 186

Arg Gly Gly Arg Cys Leu Tyr Ala Arg Arg Arg Phe Ser Ile Val Cys
 1               5                  10                  15

<210> SEQ ID NO 187
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: DISULFID
<222> LOCATION: (5)...(16)

<400> SEQUENCE: 187
```

```
Arg Gly Gly Cys Leu Tyr Ser Arg Arg Phe Ala Val Val Cys
1               5                   10                  15

Gly Arg

<210> SEQ ID NO 188
<211> LENGTH: 16
<212> TYPE: PRT
<213> ORGANISM: Artificial Sequence
<220> FEATURE:
<223> OTHER INFORMATION: Synthetic polypeptide
<221> NAME/KEY: DISULFID
<222> LOCATION: (5)...(16)

<400> SEQUENCE: 188

Arg Gly Gly Arg Cys Leu Tyr Ala Arg Arg Phe Gly Val Val Cys
1               5                   10                  15

<210> SEQ ID NO 189
<211> LENGTH: 16
<212> TYPE: PRT
<213> ORGANISM: Artificial Sequence
<220> FEATURE:
<223> OTHER INFORMATION: Synthetic polypeptide
<221> NAME/KEY: DISULFID
<222> LOCATION: (5)...(16)

<400> SEQUENCE: 189

Lys Gly Gly Arg Cys Leu Tyr Val Arg Arg Phe Ile Val Val Cys
1               5                   10                  15

<210> SEQ ID NO 190
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: MOD_RES
<222> LOCATION: 4,9
<223> OTHER INFORMATION: Xaa = Homoarginine
<221> NAME/KEY: DISULFID
<222> LOCATION: (5)...(16)

<400> SEQUENCE: 190

Arg Gly Gly Xaa Cys Leu Tyr Ala Xaa Arg Phe Ser Val Val Cys
1               5                   10                  15

Gly Arg

<210> SEQ ID NO 191
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: DISULFID
<222> LOCATION: (5)...(16)

<400> SEQUENCE: 191

Arg Gly Gly Arg Cys Leu Tyr Ser Arg Lys Lys Trp Ala Val Ser Cys
1               5                   10                  15

Gly Arg

<210> SEQ ID NO 192
<211> LENGTH: 18
<212> TYPE: PRT
<213> ORGANISM: Artificial Sequence
<220> FEATURE:
<223> OTHER INFORMATION: Synthetic polypeptide
```

```
<221> NAME/KEY: MOD_RES
<222> LOCATION: 10
<223> OTHER INFORMATION: Xaa = Homoarginine
<221> NAME/KEY: DISULFID
<222> LOCATION: (5)...(16)

<400> SEQUENCE: 192

Arg Gly Gly Arg Cys Leu Tyr Ser Arg Xaa Arg Tyr Ser Val Ile Cys
 1               5                  10                  15

Gly Arg

<210> SEQ ID NO 193
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: DISULFID
<222> LOCATION: (5)...(16)

<400> SEQUENCE: 193

Arg Ala Thr Arg Cys Ile Phe Ser Arg Arg Arg Phe Ser Val Val Cys
 1               5                  10                  15

Gly Arg

<210> SEQ ID NO 194
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: MOD_RES
<222> LOCATION: 10
<223> OTHER INFORMATION: Xaa = Homoarginine
<221> NAME/KEY: DISULFID
<222> LOCATION: (5)...(16)

<400> SEQUENCE: 194

Arg Gly Gly Lys Cys Val Tyr Gly Arg Xaa Arg Phe Ser Val Val Cys
 1               5                  10                  15

Gly Arg

<210> SEQ ID NO 195
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: MOD_RES
<222> LOCATION: 9,18
<223> OTHER INFORMATION: Xaa = D-arginine
<221> NAME/KEY: DISULFID
<222> LOCATION: (5)...(16)

<400> SEQUENCE: 195

Arg Ala Thr Arg Cys Ile Phe Gly Xaa Arg Arg Phe Gly Val Val Cys
 1               5                  10                  15

Gly Xaa

<210> SEQ ID NO 196
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: MOD_RES
<222> LOCATION: 10
```

<223> OTHER INFORMATION: Xaa = D-homoarginine
<221> NAME/KEY: DISULFID
<222> LOCATION: (5)...(16)

<400> SEQUENCE: 196

Arg Gly Gly Lys Cys Val Tyr Leu Arg Xaa Arg Phe Leu Val Val Cys
 1               5                  10                  15

Gly Arg

<210> SEQ ID NO 197
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: DISULFID
<222> LOCATION: (5)...(16)

<400> SEQUENCE: 197

Arg Gly Gly Arg Cys Val Phe Leu Arg Pro Arg Ile Gly Val Val Cys
 1               5                  10                  15

Gly Arg

<210> SEQ ID NO 198
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: DISULFID
<222> LOCATION: (5)...(16)
<221> NAME/KEY: DISULFID
<222> LOCATION: (8)...(13)

<400> SEQUENCE: 198

Arg Gly Gly Arg Cys Leu Tyr Cys Arg Arg Arg Phe Cys Ile Val Cys
 1               5                  10                  15

Gly Arg

<210> SEQ ID NO 199
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: DISULFID
<222> LOCATION: (5)...(8)
<221> NAME/KEY: DISULFID
<222> LOCATION: (13)...(16)

<400> SEQUENCE: 199

Arg Gly Gly Arg Cys Leu Tyr Cys Arg Arg Arg Phe Cys Ile Val Cys
 1               5                  10                  15

Gly Arg

<210> SEQ ID NO 200
<211> LENGTH: 17
<212> TYPE: PRT
<213> ORGANISM: Artificial Sequence
<220> FEATURE:
<223> OTHER INFORMATION: Synthetic polypeptide
<221> NAME/KEY: DISULFID
<222> LOCATION: (4)...(17)
<221> NAME/KEY: DISULFID
<222> LOCATION: (8)...(13)

<400> SEQUENCE: 200

```
Arg Gly Gly Cys Arg Leu Tyr Cys Arg Arg Arg Phe Cys Ile Val Gly
 1               5                  10                  15
Cys

<210> SEQ ID NO 201
<211> LENGTH: 18
<212> TYPE: PRT
<213> ORGANISM: Artificial Sequence
<220> FEATURE:
<223> OTHER INFORMATION: Synthetic polypeptide
<221> NAME/KEY: MOD_RES
<222> LOCATION: (1)...(18)
<223> OTHER INFORMATION: All genetically encoded amino acids are in the
      D-configuration
<221> NAME/KEY: DISULFID
<222> LOCATION: (4)...(17)
<221> NAME/KEY: DISULFID
<222> LOCATION: (8)...(13)

<400> SEQUENCE: 201

Arg Gly Gly Cys Gly Leu Tyr Cys Arg Arg Arg Phe Cys Val Val Gly
 1               5                  10                  15
Cys Arg
```